United States Patent
Wu et al.

(10) Patent No.: US 9,475,812 B2
(45) Date of Patent: Oct. 25, 2016

(54) PYRIDONAPHTHYRIDINE TYPE DUAL PI3K AND MTOR INHIBITOR AND ITS PREPARATION AND USE

(75) Inventors: Frank Wu, Jinan (CN); Yan Zhang, Jinan (CN)

(73) Assignee: Xuanzhu Pharma Co., Ltd., Jinan (CN)

(*) Notice: Subject to any disclaimer, the term of this patent is extended or adjusted under 35 U.S.C. 154(b) by 108 days.

(21) Appl. No.: 14/123,934

(22) PCT Filed: Jun. 4, 2012

(86) PCT No.: PCT/CN2012/000761
§ 371 (c)(1),
(2), (4) Date: Dec. 4, 2013

(87) PCT Pub. No.: WO2012/167606
PCT Pub. Date: Dec. 13, 2012

(65) Prior Publication Data
US 2014/0093505 A1  Apr. 3, 2014

(30) Foreign Application Priority Data

Jun. 4, 2011 (CN) .......... 2011 1 0159903
Nov. 4, 2011 (CN) .......... 2011 1 0365829

(51) Int. Cl.

| | |
|---|---|
| *C07D 471/14* | (2006.01) |
| *A61K 31/496* | (2006.01) |
| *A61K 31/4545* | (2006.01) |
| *A61K 31/4375* | (2006.01) |
| *C07D 519/00* | (2006.01) |
| *A61K 9/00* | (2006.01) |
| *A61K 31/444* | (2006.01) |
| *A61K 31/4709* | (2006.01) |
| *A61K 31/506* | (2006.01) |
| *A61K 31/5377* | (2006.01) |
| *A61K 45/06* | (2006.01) |

(52) U.S. Cl.
CPC .......... *C07D 471/14* (2013.01); *A61K 9/00* (2013.01); *A61K 31/4375* (2013.01); *A61K 31/444* (2013.01); *A61K 31/4545* (2013.01); *A61K 31/4709* (2013.01); *A61K 31/496* (2013.01); *A61K 31/506* (2013.01); *A61K 31/5377* (2013.01); *A61K 45/06* (2013.01); *C07D 519/00* (2013.01)

(58) Field of Classification Search
CPC .......... C07D 471/14; C07D 519/00; A61K 31/5377

USPC .......... 546/82; 544/126; 514/110, 293
See application file for complete search history.

(56) References Cited

U.S. PATENT DOCUMENTS

| | | |
|---|---|---|
| 2010/0056558 A1 | 3/2010 | Garcia-Echeverria et al. |
| 2011/0190326 A1 | 8/2011 | Cheng et al. |
| 2011/0288091 A1 | 11/2011 | Gray et al. |

FOREIGN PATENT DOCUMENTS

| | | |
|---|---|---|
| CN | 103373997 A | 10/2013 |
| WO | WO-2006122806 A2 | 11/2006 |
| WO | WO-2009125809 A1 | 10/2009 |
| WO | WO-2010038165 A1 | 4/2010 |
| WO | WO-2010044885 A2 | 4/2010 |

OTHER PUBLICATIONS

Liu et al., Discovery of 9-(6-aminopyridin-3-yl)-1-(3-(trifluoromethyl)phenyl)benzo[h][1,6]naphthyridin-2(1H)-one (Torin2) as a potent, selective, and orally available mammalian target of rapamycin (mTOR) inhibitor for treatment of cancer. Journal of Medical Chemistry, 54:1473-1480 (2011).

*Primary Examiner* — Rita Desai
(74) *Attorney, Agent, or Firm* — Mintz Levin Cohn Ferris Glovsky and Popeo, P.C.; Ingrid A. Beattie

(57) ABSTRACT

The present invention relates to a pyridonaphthyridine compound as represented by general formula (I), which has a dual PI3K and mTOR inhibition effect, and its pharmaceutically acceptable salt, stereoisomer and deuteride thereof, wherein $R^1$, $R^2$, $R^3$, $R^4$, $R^5$, $R^6$, $R^7$ and X are as defined in the specification; the present invention also relates to a method for preparing said compound, a pharmaceutical composition and a pharmaceutical formulation containing said compound, and uses of said compound in treating and/or preventing a proliferative disease and in the manufacture of a medicament for treating and/or preventing a proliferative disease.

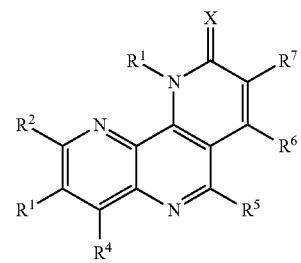

(I)

11 Claims, No Drawings

PYRIDONAPHTHYRIDINE TYPE DUAL PI3K AND MTOR INHIBITOR AND ITS PREPARATION AND USE

RELATED APPLICATIONS

This application is a national stage application, filed under 35 U.S.C. §371, of International Application No. PCT/CN2012/000761, filed on Jun. 4, 2012, which claims the benefit of Chinese Application No. 201110365829.8, filed Nov. 4, 2011 and Chinese Application No. 201110159903.0, filed Jun. 4, 2011 the contents which are each herein incorporated by reference in their entirety.

TECHNICAL FIELD

The present invention relates to a pyridonaphthyridine compound, which has a dual PI3K and mTOR inhibition effect, and its pharmaceutically acceptable salt, stereoisomer and deuteride thereof; a preparation method of said compound, a pharmaceutical composition and a pharmaceutical formulation containing said compound, and uses of said compound in treating and/or preventing a proliferative disease and in the manufacture of a medicament for treating and/or preventing a proliferative disease.

BACKGROUND

Tumor is a neoplasma formed in the organism under various oncogenic factors, bringing about the change in the cell genetic material, and leading to the abnormal gene expression and the cell abnormal proliferation. Tumor cells lose the normal growth regulation function, has an autonomic or a relative autonomic growth capability. Even if the oncogenic factor disappears, the tumor cells can continue to grow and consume a large amount of nutrient substances in the human body. If finding and treating the tumor is not prompt, the tumor cells may also transfer to various places in the whole body to grow and propagate, and release many toxins, leading to maransis, anaemia, organ function impairment and even the death of the human being.

The therapy for treating tumor mainly comprises the following three aspects: medicament therapy, surgical therapy and radiation therapy. Since it is difficult for the surgical therapy and the radiation therapy to eradicate the tumor thoroughly, and the surgical therapy and the radiation therapy have little function to the patients in the middle-late stage, therefore the medicament therapy becomes more and more important in the tumor treatment. Traditional antineoplastic drug cannot distinguish the tumor cells from the normal tissue cells, leading to a severe side effect. The targeted drug aims at the cancer cells as the specific target, can accurately target to the tumor, and accordingly improves the therapeutic level greatly and decreases the adverse effect ratio. For example, it can increase the median live time for the late-stage large intestine carcinoma by 66.7%, and the treatment effective rate for the late-stage mammary cancer by 71.3%.

Because many pharmaceuticals company has accelerated the research and development in the targeted antineoplastic drug, plus because there is a strong requirement on this kind of the antineoplastic drug in the commercial market, the molecular targeted drug has became a fastest growth unit in the global antineoplastic drug market. PI3K pathway is a place where the human tumor cells are subjected to variation most frequently, which may lead to the cell proliferation, activation, and amplification of signal. Phosphatidylinositol-3-kinase (PI3K) and mammalian target of rapamycin (mTOR) are the most important kinases for the PI3K signaling pathway.

Phosphatidylinositol-3-kinase (PI3K) refers to a member of the lipid kinase family, which can produce the phosphatidylinositol 3-phosphate (PIP3) through the 3-position phosphorylation of phosphatidylinositol to regulate the cell metabolism and growth. The second messenger PIP3 of this kind may cause the PI3K and the downstream effector (in particular AKt) to combine in pair, leading to membrane recruitment and phosphorylation, cell proliferation and activation. Therefore, the inhibition of Phosphatidylinositol-3-kinase may have an influence on the PI3K pathway, and accordingly inhibit the cancer cell proliferation and activation.

The mTOR is a serine/threonine protein kinase present in kytoplasm, belongs to phosphoinositide kinase dependent protein kinase family, and present in the organism in a form of two complexes, i.e. mTORC1 (the target point for rapamycin) and mTORC2 (not inhibited by rapamycin). The mTOR is a cell signal transducer. It regulates the response of the tumor cells to the nutrients and growth factors, and controls the blood supply to the tumor through the effect on vascular endothelial growth factor. The mTOR inhibitor can make the tumor cells starve and inhibit the mTOR, leading to the decrease in the tumor volume.

Currently, there is some drug development in the dual PI3K and mTOR inhibitor. However, most of such compounds have poor druggability, and this kind of compounds has not entered the pharmaceutical market. Journal of Medicinal Chemistry (2011), 54(5), 1473-1480, "Discovery of 9-(6-Aminopyridin-3-yl)-1-(3-(trifluoromethyl)phenyl)benzo[h][1,6]naphthyridin-2(1H)-one (Torin2) as a potent, selective, and orally available mammalian target of rapamycin (mTOR) inhibitor for treatment of cancer" discloses a compound named Torin2 and reports the research results on its in vivo pharmacokinetics.

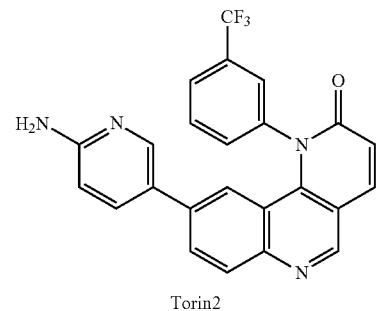 [SMILES: Nc1ccc(-c2ccc3ncc4ccc(=O)n(-c5cccc(C(F)(F)F)c5)c4c3c2)cn1]

Torin2

In summary, it has became hot in the current research for the antineoplastic drug to seek a compound having a dual PI3K and mTOR inhibition, a good activity, a high selectivity, and a good pharmacokinetic characteristics.

The present inventors, upon developing the drug with the good antineoplastic effect, have found a class of pyridonaphthyridine compound having a dual PI3K and mTOR inhibition.

SUMMARY OF THE INVENTION

Thus, the present invention provides a compound represented by general formula (I), and its pharmaceutically acceptable salt, stereoisomer and deuteride thereof:

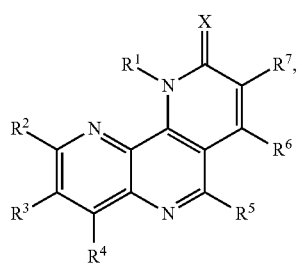

wherein:

X is O;

R¹ is hydrogen or the following group that is unsubstituted or substituted by 1-3 R⁸: $C_{1-6}$alkyl, $C_{2-6}$alkenyl, $C_{2-6}$alkynyl, 3-14-membered cycloalkyl, 6-14-membered aryl, 3-14-membered heterocyclyl, 7-12-membered spiro ring group or 7-12-membered bridged ring group;

R² is hydrogen or the following group that is unsubstituted or substituted by 1-3 R⁸': $C_{1-6}$alkyl, $C_{2-6}$alkenyl, $C_{2-6}$alkynyl, 3-14-membered cycloalkyl, 6-14-membered aryl, 3-14-membered heterocyclyl, 7-12-membered spiro ring group or 7-12-membered bridged ring group;

each of R³ and R⁴ is independently selected from the group consisting of hydrogen, halogen, cyano, amino, hydroxy, sulfonyl, —$SO_2C_{1-6}$alkyl, and $C_{1-6}$alkyl and $C_{1-6}$alkoxyl that are unsubstituted or substituted with 1-3 substituents selected from halogen, hydroxy and/or carboxyl;

R⁵ is selected from the group consisting of hydrogen, cyano, amino, sulfonyl, —$SO_2C_{1-6}$alkyl, and $C_{1-6}$alkyl and $C_{1-6}$alkoxyl that are unsubstituted or substituted with 1-3 substituents selected from halogen, hydroxy and/or carboxyl;

each of R⁶ and R⁷ is independently selected from the group consisting of hydrogen, hydroxy, halogen, amino, and $C_{1-6}$alkyl and $C_{1-6}$alkoxyl that are unsubstituted or substituted with 1-3 substituents selected from halogen, hydroxy and/or carboxyl;

each of R⁸ and R⁸' are independently selected from the group consisting of (1) hydroxy, halogen, amino, cyano, —$(CH_2)_nNR^aR^b$, —$(CH_2)_nC(O)R^c$, —$(CH_2)_nS(O)_mR^c$, —$(CH_2)_nS(O)_mNR^aR^b$, —$(CH_2)_nNR^aS(O)_mR^c$, —$(CH_2)_nC(O)(CH_2)_nNR^aR^b$, —$(CH_2)_nOC(O)R^c$, —$(CH_2)_nNR^aC(O)R^c$, and —$(CH_2)_nNR^aC(O)NR^aR^b$, (2) $C_{1-6}$alkyl, $C_{2-6}$alkenyl, $C_{2-6}$alkynyl and $C_{1-6}$alkoxyl, which are unsubstituted or substituted by 1-3 substituents selected from cyano, halogen and/or hydroxy, and (3) 3-14-membered cycloalkyl, 6-14-membered aryl and 3-14-membered heterocyclyl, which are unsubstituted or substituted by 1-3 substituents selected from cyano, trifluoromethyl, halogen, $C_{1-6}$alkyl, $C_{2-8}$alkenyl, $C_{2-8}$alkynyl, $C_{1-6}$alkoxyl, —$(CH_2)_nNR^aR^b$, —$(CH_2)_nC(O)R^{c'}$, —$(CH_2)_nC(O)(CH_2)_nNR^aR^b$, —$(CH_2)_nS(O)_mR^{c'}$, —$(CH_2)_nS(O)_mNR^aR^b$, —$(CH_2)_nNR^aS(O)_mR^{c'}$, —$(CH_2)_nOC(O)R^{c'}$, —$(CH_2)_nNR^aC(O)R^{c'}$ and/or —$(CH_2)_nNR^aC(O)NR^aR^b$;

wherein each of $R^a$ and $R^b$ is independently selected from the group consisting of hydrogen, or $C_{1-6}$alkyl that is unsubstituted or substituted by 1-3 substituents selected from hydroxy, halogen and/or cyano;

$R^c$ is $C_{1-6}$alkyl or $C_{1-6}$alkoxyl, both of which are unsubstituted or substituted by 1-3 substitutents selected from hydroxy, halogen, cyano and/or trifluoromethyl;

$R^{c'}$ is $C_{1-6}$alkyl, $C_{1-6}$alkoxyl, 3-8-membered monocyclic cycloalkyl or 3-8-membered monocyclic heterocyclyl, all of which are unsubstituted or substituted by 1-3 substitutents selected from hydroxy, halogen and/or cyano;

m is 0, 1 or 2; and n is 0-4.

The present invention also provides a pharmaceutical composition containing the compound of general formula (I), and its pharmaceutically acceptable salt, stereoisomer or deuteride thereof.

The present invention also provides a pharmaceutical formulation containing the compound of general formula (I), and its pharmaceutically acceptable salt, stereoisomer or deuteride thereof, and a pharmaceutically acceptable carrier.

The present invention also provides the compound of general formula (I), and its pharmaceutically acceptable salt, stereoisomer or deuteride thereof, and a pharmaceutical composition containing the compound of general formula (I), and pharmaceutically acceptable salt, stereoisomer or deuteride thereof, as a medicament for treating a proliferative disease.

The present invention also provides a use of the compound of general formula (I), and its pharmaceutically acceptable salt, stereoisomer or deuteride thereof, and a pharmaceutical composition containing the compound of general formula (I), and pharmaceutically acceptable salt, stereoisomer or deuteride thereof in the manufacture of a medicament for treating a proliferative disease.

The present invention also provides a method of treating a proliferative disease, comprising the step of administrating a subject in need thereof an effective amount of the compound of general formula (I), and its pharmaceutically acceptable salt, stereoisomer or deuteride thereof, or a pharmaceutical composition containing the compound of general formula (I), and its pharmaceutically acceptable salt, stereoisomer or deuteride thereof.

The present invention also provides a preparation method of the compound of general formula (I), i.e.

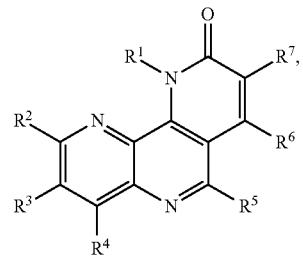

comprising the following steps:

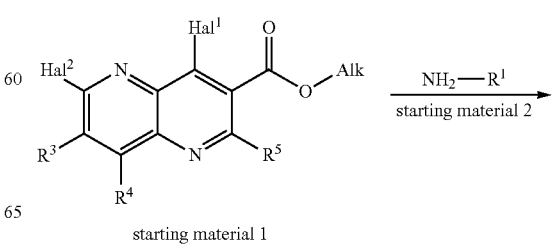

starting material 1

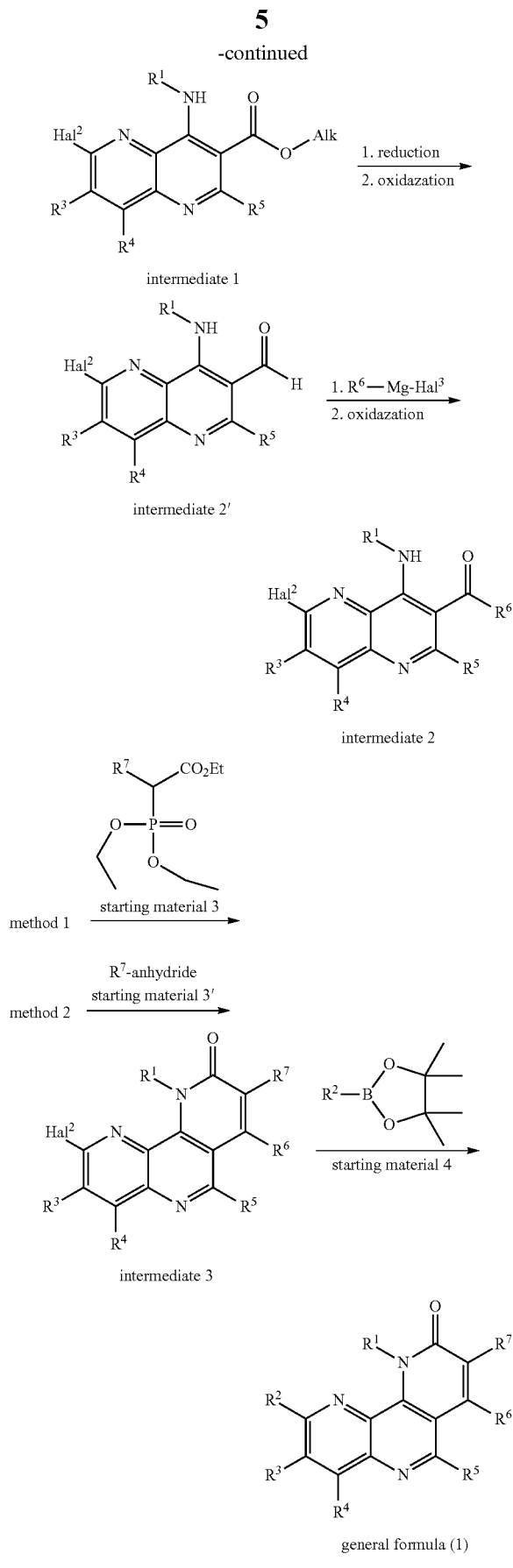

wherein $R^1$, $R^2$, $R^3$, $R^4$, $R^5$, $R^6$ and $R^7$ are defined as hereinbefore, $Hal^1$, $Hal^2$ and $Hal^3$ represent halogen, which is each independently selected from the group consisting of F, Cl, Br and I, and $Hal^1$, $Hal^2$ and $Hal^3$ can be identical or different; Alk represents a lower alkyl, e.g. "$C_{1-6}$alkyl", preferably "$C_{1-4}$alkyl" and more preferably ethyl; "anhydride" is preferably an organic acid anhydride, for example, selected from but not limited to acetic anhydride, propionic anhydride, preferably acetic anhydride;

1. Preparation of Intermediate 1

Starting Material 1 and Starting Material 2 are reacted under heating to reflux in an alcohol organic solvent in presence of a base until the starting material disappears to produce Intermediate 1;

2. Preparation of Intermediate 2'

Intermediate 1 is reacted with an reductant in an alcohol organic solvent; the solvent is removed under a reduced pressure; water is added to the reaction mixture; the resulting mixture is extracted with a halogenated hydrocarbon organic solvent; the organic phase is concentrated, to which is added an oxidant; the resulting mixture is reacted under stirring to produce Intermediate 2';

3. Preparation of Intermediate 2

In the nitrogen protection, Intermediate 2' and a Grignard reagent $R^6$—Mg-$Hal^3$ are reacted and then oxidized to produce Intermediate 2;

4. Preparation of Intermediate 3

Method 1: In a sealed vessel, Intermediate 2 and Starting Material 3 are reacted in an alcohol organic solvent in the presence of an inorganic base at 110-180° C. to produce Intermediate 3; or Method 2: Intermediate 2 is dissolved in a non-protonic polar organic solvent and Starting Material 3'; the reaction is conducted in a microwave reactor until the starting material disappears to produce Intermediate 3;

and

5. Preparation of Compound of Formula (I)

Intermediate 3 and Starting Material 4 are dissolved in an organic solvent; the resulting mixture was reacted in the presence of a catalyst and a base under reflux in a nitrogen-protecting atmosphere to produce the compound of formula (I);

If necessary, a functional group that needs to be protected, such as hydroxy, amino and the like, can be protected; and afterwards can be deprotected according to the conventional method.

In the above preparation method,

Said "alcohol organic solvent" is selected from, for example, but not limited to, methanol, ethanol, isopropanol, t-butanol and the like, preferably ethanol, t-butanol;

Said "organic solvent" is selected from said "alcohol organic solvent", an "aromatic hydrocarbon organic solvent" or a mixture thereof, said "aromatic hydrocarbon organic solvent" includes but is not limited to, for example, benzene, toluene, xylene and the like, preferably toluene;

Said "halogenating hydrocarbon organic solvent" is selected from, for example, but not limited to, chlorobenzene, dichlorobenzene, chloromethane, dichlormethane and the like, preferably dichlormethane;

Said "base" includes an organic base and an inorganic base, preferably an inorganic base. Said inorganic base is selected from, for example, but not limited to potassium hydroxide, sodium hydroxide, zinc hydroxide, calcium hydroxide, potassium carbonate, potassium bicarbonate, sodium carbonate, sodium bicarbonate and the like, preferably potassium carbonate and sodium carbonate; said organic base includes but is not limited to, for example, triethylamine, ethylene diamine, ethanolamine, diethanolamine, triethanolamine, sodium ethoxide, pyridine, dimethylaminopyridine, sodium methoxide, potassium ethoxide, potassium tertbutoxide, butyl lithium, phenyl lithium, lithium diisopropylamide, lithium hexamethyldisilazide and the like;

Said "non protonic polar organic solvent" is selected from, for example, but not limited to, N,N-dimethylacetamide, N,N-dimethyl formamide, dimethyl sulfoxide, acetonitrile and the like, preferably N,N-dimethylacetamide;

Said "reductant" is preferably metal hydrides, is selected from, for example, but not limited to sodium borohydride, lithium aluminum hydride, diborane and the like, preferably sodium borohydride;

Said "oxidant" preferably is a high valency oxidant which comprises a varying valency element, and selected from, for example, but not limited to potassium permanganate, potassium chlorate, manganese dioxide, ferric chloride and the like, preferably manganese dioxide; and Said "catalyst" is selected from, for example, but not limited to, nickel catalyst, palladium catalyst, platinum catalyst, metal hydride catalyst and the like, preferably palladium catalyst, such as Pd/C, palladium chloride, palladium tetrakis(triphenylphosphine) and the like.

In a preferable embodiment of the present compound of general formula (I), $R^1$ is 3-14-membered cycloalkyl, 6-14-membered aryl, 3-14-membered heterocyclyl, 7-12-membered spiro ring group or 7-12-membered bridged ring group, all of which are unsubstituted or substituted by 1-3 $R^8$, wherein $R^8$ is selected from the group consisting of
(1) hydroxy, halogen, amino, cyano, —$(CH_2)_nNR^aR^b$, —$(CH_2)_nC(O)R^c$, —$(CH_2)_n S(O)_mR^{c'}$, —$(CH_2)_nS(O)_mNR^aR^b$, —$(CH_2)_nNR^aS(O)_mR^{c'}$, —$(CH_2)_nC(O)(CH_2)_nNR^aR^b$, —$(CH_2)_nOC(O)R^{c'}$, —$(CH_2)_nNR^aC(O)R^{c'}$ and —$(CH_2)_nNR^aC(O)NR^aR^b$,
(2) $C_{1-6}$alkyl and $C_{1-6}$alkoxyl, both of which are unsubstituted or substituted by 1-3 substitutents selected from cyano, halogen and/or hydroxy, and
(3) 3-8-membered monocyclic cycloalkyl, 6-14-membered aryl and 3-8-membered monocyclic heterocyclyl, all of which are unsubstituted or substituted by 1-3 substitutents selected from cyano, trifluoromethyl, halogen, $C_{1-6}$alkoxyl, —$(CH_2)_nNR^aR^b$, —$(CH_2)_nC(O)R^{c'}$, —$(CH_2)_nC(O)(CH_2)_nNR^aR^b$, —$(CH_2)_nS(O)_mR^{c'}$, —$(CH_2)_nS(O)_mNR^aR^b$, —$(CH_2)_nNR^aS(O)_mR^{c'}$, —$(CH_2)_nOC(O)R^{c'}$, —$(CH_2)_nNR^aC(O)R^{c'}$ and/or —$(CH_2)_nNR^aC(O)NR^aR^b$,
wherein
each of $R^a$ and $R^b$ is independently selected from the group consisting of hydrogen, or $C_{1-6}$alkyl that is unsubstituted or substituted by 1-3 substitutents selected from hydroxy, halogen and/or cyano,
$R^c$ is $C_{1-6}$alkyl or $C_{1-6}$alkoxyl, both of which are unsubstituted or substituted by 1-3 substitutents selected from hydroxy, halogen, cyano and/or trifluoromethyl,
$R^{c'}$ is $C_{1-6}$alkyl and $C_{1-6}$alkoxyl, both of which are unsubstituted or substituted by 1-3 substitutents selected from hydroxy, halogen and/or cyano,
m is 0, 1 or 2, and
n is 0, 1, 2 or 3.

In a further preferable embodiment of the present compound of general formula (I), $R^1$ is 3-8-membered monocyclic cycloalkyl, 6-14-membered aryl or 3-8-membered monocyclic heterocyclyl that are unsubstituted or substituted by 1-3 $R^8$, wherein $R^8$ is selected from the group consisting of
(1) hydroxy, halogen, amino, cyano, —$(CH_2)_nC(O)R^c$ and —$(CH_2)_nS(O)_mR^c$, wherein $R^c$ is $C_{1-4}$alkyl or $C_{1-4}$alkoxyl, both of which are unsubstituted or substituted by hydroxy, halogen, cyano or trifluoromethyl,
(2) $C_{1-4}$alkyl and $C_{1-4}$alkoxyl, which are unsubstituted or substituted by cyano, hydroxy or 1-3 halogens, and
(3) 5-8-membered monocyclic heterocyclyl that is unsubstituted or substituted by 1-3 substitutents selected from cyano, trifluoromethyl, halogen, $C_{1-4}$alkoxyl, —$(CH_2)_nNR^aR^b$, —$(CH_2)_nC(O)R^{c'}$, —$(CH_2)_nC(O)(CH_2)_nNR^aR^b$ and/or —$(CH_2)_nS(O)_mR^c$, wherein each of $R^a$ and $R^b$ is independently selected from the group consisting of hydrogen, or $C_{1-4}$alkyl that is unsubstituted or substituted by 1-3 substitutents selected from hydroxy, halogen and/or cyano, $R^{c'}$ is $C_{1-4}$alkyl or $C_{1-4}$alkoxyl, both of which are unsubstituted or substituted by 1-3 substitutents selected from hydroxy, halogen and/or cyano,
m is 0, 1 or 2, and
n is 0, 1, 2 or 3.

In a further preferable embodiment of the present compound of general formula (I), $R^1$ is 6-10-membered aryl or 3-8-membered saturated monocyclic heterocyclyl or 5-6-membered aromatic monocyclic heterocyclyl, all of which are unsubstituted or substituted by 1-3 $R^8$, wherein $R^8$ is selected from the group consisting of
(1) hydroxy, halogen, amino, cyano and —$C(O)R^c$, wherein $R^c$ is $C_{1-4}$alkyl or $C_{1-4}$alkoxyl, both of which are unsubstituted or substituted by hydroxy, halogen, cyano or trifluoromethyl,
(2) $C_{1-4}$alkyl and $C_{1-4}$alkoxyl, which are unsubstituted or substituted by cyano, hydroxy or 1-3 halogens, and
(3) 5-6-membered monocyclic heterocyclyl, which is unsubstituted or substituted by 1-3 substitutents selected from cyano, trifluoromethyl, halogen, $C(O)R^{c'}$ and/or —$S(O)_2R^{c'}$, wherein $R^{c'}$ is $C_{1-4}$alkyl or $C_{1-4}$alkoxyl, which are unsubstituted or substituted by 1-3 substitutents selected from hydroxy, halogen and/or cyano.

In a further preferable embodiment of the present compound of general formula (I), $R^1$ is 6-10-membered aryl or 5-6-membered monocyclic heterocyclyl that are unsubstituted or substituted by 1-3 $R^8$, wherein $R^8$ is (1) amino or —$C(O)R^c$, $R^c$ is $C_{1-4}$alkyl that is unsubstituted or substituted by hydroxy or halogen, (2) $C_{1-4}$alkyl or $C_{1-4}$alkoxyl that are unsubstituted or substituted by cyano or 1-3 halogens, or (3) 5-6-membered monocyclic heterocyclyl that is unsubstituted or substituted by cyano or trifluoromethyl.

In a further preferable embodiment of the present compound of general formula (I), $R^1$ is phenyl, naphthyl or 5-6-membered saturated monocyclic heterocyclyl, all of which are unsubstituted or substituted by 1-3 $R^8$, wherein $R^8$ is
(1) amino or —$C(O)R^c$, $R^c$ is $C_{1-4}$alkyl that is unsubstituted or substituted by hydroxy or halogen,
(2) $C_{1-4}$alkyl or $C_{1-4}$alkoxyl, both of which are unsubstituted or substituted by cyano or 1-3 fluoro, or
(3) piperazinyl or piperidinyl, both of which are unsubstituted or substituted by cyano or trifluoromethyl.

In a further preferable embodiment of the present compound of general formula (I), $R^1$ is phenyl, piperidinyl or piperazinyl, all of which are unsubstituted or substituted by 1-2 $R^8$, $R^8$ is:
(1) amino or —$C(O)R^c$, $R^c$ is $C_{1-2}$alkyl that is unsubstituted or substituted by hydroxy,
(2) $C_{1-2}$alkyl, which is unsubstituted or substituted by cyano or three fluoro, or
(3) piperazinyl or piperidinyl, both of which are unsubstituted or substituted by cyano or trifluoromethyl.

In a preferable embodiment of the present compound of general formula (I), $R^2$ is 3-14-membered cycloalkyl, 6-14- membered aryl or 3-14-membered heterocyclyl, all of which are unsubstituted or substituted by 1-3 $R^{8'}$, wherein $R^{8'}$ is selected from the group consisting of (1) hydroxy, halogen, amino, cyano, —$(CH_2)_nNR^aR^b$, —$(CH_2)_nC(O)R^c$, —$(CH_2)_nS(O)_mR^c$, —$(CH_2)_nS(O)_mNR^aR^b$, —$(CH_2)_nNR^aS(O)_mR^c$, —$(CH_2)_nC(O)(CH_2)_nNR^aR^b$, —$(CH_2)_nOC(O)R^c$, —$(CH_2)_nNR^aC(O)R^c$, and —$(CH_2)_nNR^aC(O)NR^aR^b$, (2) $C_{1-6}$alkyl and $C_{1-6}$alkoxyl, both of which are unsubstituted or substituted by 1-3 substituents selected from cyano, halogen and/or hydroxy, and (3) 3-8-membered monocyclic cycloalkyl, 6-14-membered aryl and 3-8-membered monocyclic heterocyclyl, which are unsubstituted or substituted by 1-3 substituents selected from cyano, trifluoromethyl, halogen, $C_{1-6}$alkyl, $C_{1-6}$alkoxyl, —$(CH_2)_nNR^aR^b$, —$(CH_2)_nC(O)R^{c'}$, —$(CH_2)_nC(O)(CH_2)_nNR^aR^b$, —$(CH_2)_nS(O)_mR^{c'}$, —$(CH_2)_nS(O)_mNR^aR^b$, —$(CH_2)_nNR^aS(O)_mR^{c'}$, —$(CH_2)_nOC(O)R^{c'}$, —$(CH_2)_nNR^aC(O)R^{c'}$ and/or —$(CH_2)_nNR^aC(O)NR^aR^b$;

wherein each of $R^a$ and $R^b$ is independently selected from the group consisting of hydrogen, or $C_{1-6}$alkyl that is unsubstituted or substituted by 1-3 substituents selected from hydroxy, halogen and/or cyano;

$R^c$ is $C_{1-6}$alkyl or $C_{1-6}$alkoxyl, both of which are unsubstituted or substituted by 1-3 substituents selected from hydroxy, halogen, cyano and/or trifluoromethyl;

$R^{c'}$ is $C_{1-6}$alkyl or $C_{1-6}$alkoxyl, both of which are unsubstituted or substituted by 1-3 substituents selected from hydroxy, halogen and/or cyano;

m is 0, 1 or 2; and n is 0, 1, 2 or 3.

In a further preferable embodiment of the present compound of general formula (I), $R^2$ is 6-14-membered aryl or 5-10-membered heterocyclyl, both of which are unsubstituted or substituted by 1-3 $R^{8'}$s, wherein $R^{8'}$ is selected from the group consisting of (1) hydroxy, halogen, cyano, amino, —$(CH_2)_nC(O)R^c$, —$(CH_2)_nNR^aR^b$, —$(CH_2)_nS(O)_mR^c$, —$(CH_2)_nS(O)_mNR^aR^b$, —$(CH_2)_nNR^aS(O)_mR^c$, —$(CH_2)_nC(O)(CH_2)_nNR^aR^b$, —$(CH_2)_nOC(O)R^c$, —$(CH_2)_nNR^aC(O)R^c$ and —$(CH_2)_nNR^aC(O)NR^aR^b$, (2) $C_{1-4}$alkyl and $C_{1-4}$alkoxyl, which are unsubstituted or substituted by 1-3 substituents selected from cyano, halogen and/or hydroxy, and (3) 5-8-membered monocyclic heterocyclyl, which is unsubstituted or substituted by 1-3 substituents selected from cyano, trifluoromethyl, halogen, $C_{1-4}$alkyl, $C_{1-4}$alkoxyl, —$(CH_2)_nNR^aR^b$, —$(CH_2)_nC(O)R^{c'}$, —$(CH_2)_nC(O)(CH_2)_nNR^aR^b$, —$(CH_2)_nS(O)_mR^{c'}$, —$(CH_2)_nS(O)_mNR^aR^b$, —$(CH_2)_nNR^aS(O)_mR^{c'}$, —$(CH_2)_nOC(O)R^{c'}$, —$(CH_2)_nNR^aC(O)R^{c'}$ and/or —$(CH_2)_nNR^aC(O)NR^aR^b$;

each of $R^a$ and $R^b$ is independently hydrogen, or $C_{1-4}$alkyl that is unsubstituted or substituted by 1-3 substituents selected from hydroxy and/or halogen;

$R^c$ is $C_{1-4}$alkyl or $C_{1-4}$alkoxyl, both of which are unsubstituted or substituted by 1-3 substituents selected from hydroxy, halogen and/or cyano;

$R^{c'}$ is $C_{1-4}$alkyl or $C_{1-4}$alkoxyl, both of which are unsubstituted or substituted by 1-3 substituents selected from hydroxy and/or halogen;

m is 0, 1 or 2; and n is 0, 1, 2 or 3.

In a further preferable embodiment of the present compound of general formula (I), $R^2$ is 6-10-membered aryl, 5-6-membered partially saturated monocyclic heterocyclyl, 5-6-membered aromatic monocyclic heterocyclyl or 9-10-membered fused heterocyclyl, all of which are unsubstituted or substituted by 1-3 $R^{8'}$, wherein $R^8$ is:

(1) hydroxy, halogen, cyano, amino, —$(CH_2)_nNR^aC(O)R^c$ or —$(CH_2)_nS(O)_mR^c$, wherein $R^a$ is hydrogen or $C_{1-4}$alkyl that is unsubstituted or substituted by 1-3 substituents selected from hydroxy and/or halogen, $R^c$ is $C_{1-4}$alkyl or $C_{1-4}$alkoxyl, both of which are unsubstituted or substituted by 1-3 substituents selected from hydroxy, halogen and/or cyano, m is 0, 1 or 2; and n is 0, 1, 2 or 3;

(2) $C_{1-4}$alkyl or $C_{1-4}$alkoxyl, both of which are unsubstituted or substituted by 1-3 substituents selected from cyano, halogen and/or hydroxy; or (3) 5-6-membered monocyclic heterocyclyl, which is unsubstituted or substituted by cyano, trifluoromethyl, halogen, $C_{1-4}$alkyl or $C_{1-4}$alkoxyl.

In a further preferable embodiment of the present compound of general formula (I), $R^2$ is 6-10-membered aryl or 5-10-membered heterocyclyl, each of which are unsubstituted or substituted by 1-3 $R^{8'}$, wherein $R^{8'}$ is (1) hydroxy, halogen, amino, cyano, —NHC(O)$R^c$ or —S(O)$_m R^c$, wherein m is 0, 1 or 2, $R^c$ is $C_{1-4}$alkyl, (2) $C_{1-4}$alkyl or $C_{1-4}$alkoxyl, both of which are unsubstituted or substituted by hydroxy or 1-3 halogens, or (3) 5-6-membered monocyclic heterocyclyl, which is unsubstituted or substituted by cyano, trifluoromethyl, halogen, $C_{1-4}$alkyl or $C_{1-4}$alkoxyl.

In a further preferable embodiment of the present compound of general formula (I), $R^2$ is 6-10-membered aryl, 5-6-membered partially saturated monocyclic heterocyclyl, 5-6-membered aromatic monocyclic heterocyclyl or 9-10-membered fused heterocyclyl, all of which are unsubstituted or substituted by 1-3 $R^{8'}$, wherein $R^{8'}$ is (1) hydroxy, halogen, amino, cyano, —NHC(O)$R^c$ or —S(O)$_m R^c$, wherein m is 0, 1 or 2, $R^c$ is $C_{1-4}$alkyl, (2) $C_{1-4}$alkyl or $C_{1-4}$alkoxyl, both of which are unsubstituted or substituted by hydroxy or 1-3 halogens, or (3) 5-6-membered monocyclic heterocyclyl, which is unsubstituted or substituted by cyano, trifluoromethyl, halogen, $C_{1-4}$alkyl or $C_{1-4}$alkoxyl.

In a further preferable embodiment of the present compound of general formula (I), $R^2$ is phenyl, pyridinyl, pyrimidinyl, pyridazinyl, pyrazinyl, pyrazolyl, imidazolyl, pyrrolyl, oxazolyl, isoxazolyl, thiazolyl, isothiazolyl, indazolyl, quinolinyl, isoquinolinyl, indolyl, pyrrolopyridine, dihydropyrrolopyridine or pyrazolopyridinyl, all of which are unsubstituted or substituted by 1-3 $R^{8'}$, wherein $R^{8'}$ is:

(1) hydroxy, halogen, amino, cyano, —NHC(O)$R^c$ or —S(O)$_m R^c$, wherein m is 0 or 2, $R^c$ is $C_{1-4}$alkyl, (2) $C_{1-4}$alkyl or $C_{1-4}$alkoxyl, both of which are unsubstituted or substituted by hydroxy or 1-3 fluoro, or (3) pyridinyl, piperidinyl, pyrimidinyl, pyridazinyl, pyrazinyl, piperazinyl, pyrazolyl, imidazolyl, pyrrolyl, pyrrolidinyl or morpholinyl, all of which are unsubstituted or substituted by cyano, trifluoromethyl, halogen, $C_{1-4}$alkyl or $C_{1-4}$alkoxyl.

In a further preferable embodiment of the present compound of general formula (I), $R^2$ is phenyl, pyridinyl, pyrimidinyl, pyridazinyl, pyrazinyl, pyrazolyl, imidazolyl, pyrrolyl, oxazolyl, isoxazolyl, thiazolyl, isothiazolyl, quinolinyl, isoquinolinyl, pyrrolopyridine, dihydropyrrolopyridine or indolyl, all of which are unsubstituted or substituted by 1-2 $R^{8'}$, wherein $R^8$ is:

(1) halogen, amino, cyano, —NHC(O)$R^c$ or —S(O)$_m R^c$, wherein m is 0 or 2, $R^c$ is $C_{1-4}$alkyl, (2) $C_{1-4}$alkyl or $C_{1-4}$alkoxyl, both of which are unsubstituted or substituted by hydroxy or three fluoro, or (3) piperazinyl, pyrazolyl, piperidinyl, morpholinyl, pyrimidinyl, pyridazinyl, pyrazinyl, pyrrolyl or pyrrolidinyl, all of which are unsubstituted or substituted by $C_{1-4}$alkyl.

In a preferable embodiment of the present compound of general formula (I), each of $R^3$ and $R^4$ is independently selected from the group consisting of hydrogen, halogen, cyano, amino, hydroxy, and $C_{1-6}$alkyl and $C_{1-6}$alkoxyl that are unsubstituted or substituted by hydroxy or 1-3 halogens.

In a further preferable embodiment of the present compound of general formula (I), each of $R^3$ and $R^4$ are independently selected from the group consisting of hydrogen, halogen, cyano, amino, hydroxy, trifluoromethyl and trifluoromethoxy.

In a further preferable embodiment of the present compound of general formula (I), each of $R^3$ and $R^4$ is hydrogen.

In a preferable embodiment of the present compound of general formula (I), $R^5$ is hydrogen, cyano, amino, or $C_{1-6}$alkyl or $C_{1-6}$alkoxyl, each of which are unsubstituted or substituted by hydroxy, carboxyl or 1-3 halogens.

In a further preferable embodiment of the present compound of general formula (I), $R^5$ is hydrogen.

In a preferable embodiment of the present compound of general formula (I), each of $R^6$ and $R^7$ is independently selected from the group consisting of hydrogen, hydroxy, halogen, amino, and $C_{1-6}$alkyl and $C_{1-6}$alkoxyl that are unsubstituted or substituted by hydroxy or 1-3 halogens.

In a further preferable embodiment of the present compound of general formula (I), each of $R^6$ and $R^7$ is independently hydrogen or $C_{1-4}$alkyl.

In another preferable embodiment of the present compound of general formula (I),
$R^1$ is 3-14-membered cycloalkyl, 6-14-membered aryl, 3-14-membered heterocyclyl, 7-12-membered spiro ring group or 7-12-membered bridged ring group, all of which are unsubstituted or substituted by 1-3 $R^8$;
$R^2$ is 3-14-membered cycloalkyl, 6-14-membered aryl or 3-14-membered heterocyclyl, all of which are unsubstituted or substituted by 1-3 $R^8$;
each of $R^3$ and $R^4$ is independently selected from the group consisting of hydrogen, halogen, cyano, amino, hydroxy, trifluoromethyl and trifluoromethoxy;
$R^5$ is hydrogen, cyano or amino;
each of $R^6$ and $R^7$ is independently selected from the group consisting of hydrogen, hydroxy, halogen, amino, and $C_{1-6}$alkyl;
each of $R^8$ and $R^{8'}$ is independently selected from the group consisting of
(1) hydroxy, halogen, amino, cyano, —$(CH_2)_nC(O)R^c$, —$(CH_2)_nNR^aR^b$, —$(CH_2)_nS(O)_mR^c$, —$(CH_2)_nS(O)_mNR^aR^b$, —$(CH_2)_nNR^aS(O)_mR^c$, —$(CH_2)_nC(O)(CH_2)_nNR^aR^b$, —$(CH_2)_nOC(O)R^c$, —$(CH_2)_nNR^aC(O)R^c$ and —$(CH_2)_nNR^aC(O)NR^aR^b$,
(2) $C_{1-6}$alkyl and $C_{1-6}$alkoxyl, both of which are unsubstituted or substituted by 1-3 substitutents selected from cyano, halogen and/or hydroxy, and
(3) 3-8-membered monocyclic cycloalkyl, 6-14-membered aryl and 3-8-membered monocyclic heterocyclyl, which are unsubstituted or substituted by 1-3 substitutents selected from cyano, trifluoromethyl, halogen, $C_{1-6}$alkyl, $C_{1-6}$alkoxyl, —$(CH_2)_nNR^aR^b$, —$(CH_2)_nC(O)R^{c'}$, —$(CH_2)_nC(O)(CH_2)_nNR^aR^b$, —$(CH_2)_nS(O)_mR^{c'}$, —$(CH_2)_nS(O)_mNR^aR^b$, —$(CH_2)_nNR^aS(O)_mR^{c'}$, —$(CH_2)_nOC(O)R^{c'}$, —$(CH_2)_nNR^aC(O)R^{c'}$ and/or —$(CH_2)_nNR^aC(O)NR^aR^b$;
wherein
each of $R^a$ and $R^b$ is independently selected from the group consisting of hydrogen, or $C_{1-6}$alkyl that is unsubstituted or substituted by 1-3 substitutents selected from hydroxy, halogen and/or cyano;
$R^c$ is $C_{1-6}$alkyl and $C_{1-6}$alkoxyl, each of which are unsubstituted or substituted by 1-3 substitutents selected from hydroxy, halogen, cyano and/or trifluoromethyl;

$R^{c'}$ is $C_{1-6}$alkyl or $C_{1-6}$alkoxyl, both of which are unsubstituted or substituted by 1-3 substitutents selected from hydroxy, halogen and/or cyano;
m is 0, 1 or 2; and
n is 0, 1, 2 or 3.

In another preferable embodiment of the present compound of general formula (I),
$R^1$ is 3-8-membered monocyclic cycloalkyl, 6-14-membered aryl or 3-8-membered monocyclic heterocyclyl, each of which are unsubstituted or substituted by 1-3 $R^8$;
$R^2$ is 3-8-membered monocyclic cycloalkyl, 6-14-membered aryl or 5-10-membered heterocyclyl, all of which are unsubstituted or substituted by 1-3 $R^8$;
each of $R^3$, $R^4$ and $R^5$ is hydrogen;
each of $R^6$ and $R^7$ is independently hydrogen or $C_{1-4}$alkyl;
$R^8$ is selected from the group consisting of
(1) hydroxy, halogen, cyano, amino, and —$(CH_2)_nC(O)R^c$,
(2) $C_{1-4}$alkyl and $C_{1-4}$alkoxyl, which are unsubstituted or substituted by 1-3 substitutents selected from cyano, halogen and/or hydroxy, and
(3) 5-8-membered saturated monocyclic heterocyclyl, which is unsubstituted or substituted by 1-3 substitutents selected from cyano, trifluoromethyl, halogen, —$(CH_2)_nC(O)R^{c'}$, —$(CH_2)_nC(O)(CH_2)_nNR^aR^b$ and/or —$(CH_2)_nS(O)_mR^{c'}$;
$R^{8'}$ is selected from the group consisting of
(1) hydroxy, halogen, cyano, amino, —$(CH_2)_nC(O)R^c$, —$(CH_2)_nNR^aR^b$, —$(CH_2)_nS(O)_mR^c$, —$(CH_2)_nS(O)_mNR^aR^b$, —$(CH_2)_nNR^aS(O)_mR^c$, —$(CH_2)_nC(O)(CH_2)_nNR^aR^b$, —$(CH_2)_nOC(O)R^c$, —$(CH_2)_nNR^aC(O)R^c$ and —$(CH_2)_nNR^aC(O)NR^aR^b$,
(2) $C_{1-4}$alkyl and $C_{1-4}$alkoxyl, which are unsubstituted or substituted by 1-3 substitutents selected from cyano, halogen and/or hydroxy, and
(3) 5-8-membered monocyclic heterocyclyl, which is unsubstituted or substituted by 1-3 substitutents selected from cyano, trifluoromethyl, halogen, $C_{1-4}$alkyl, $C_{1-4}$alkoxyl, —$(CH_2)_nNR^aR^b$, —$(CH_2)_nC(O)R^{c'}$, —$(CH_2)_nC(O)(CH_2)_nNR^aR^b$, —$(CH_2)_nS(O)_mR^{c'}$, —$(CH_2)_nS(O)_mNR^aR^b$, —$(CH_2)_nNR^aS(O)_mR^{c'}$, —$(CH_2)_nOC(O)R^{c'}$, —$(CH_2)_nNR^aC(O)R^{c'}$ and/or —$(CH_2)_nNR^aC(O)NR^aR^b$;
each of $R^a$ and $R^b$ is independently hydrogen, or $C_{1-4}$alkyl that is unsubstituted or substituted by 1-3 substitutents selected from hydroxy and/or halogen;
$R^c$ is $C_{1-4}$alkyl or $C_{1-4}$alkoxyl, both of which are unsubstituted or substituted by 1-3 substitutents selected from hydroxy, halogen and/or cyano;
$R^{c'}$ is $C_{1-4}$alkyl or $C_{1-4}$alkoxyl, both of which are unsubstituted or substituted by 1-3 substitutents selected from hydroxy and/or halogen;
m is 0, 1 or 2; and
n is 0, 1, 2 or 3.

In a further preferable embodiment of the present compound of general formula (I):
$R^1$ is 6-10-membered aryl, 3-8-membered saturated monocyclic heterocyclyl or 5-6-membered aromatic monocyclic heterocyclyl, all of which are unsubstituted or substituted by 1-3 $R^8$;
$R^2$ is 6-10-membered aryl, 5-6-membered partially saturated monocyclic heterocyclyl, 5-6-membered aromatic monocyclic heterocyclyl or 9-10-membered fused heterocyclyl, all of which are unsubstituted or substituted by 1-3 $R^{8'}$;
each of $R^3$, $R^4$ and $R^5$ is hydrogen;
each of $R^6$ and $R^7$ is independently hydrogen or $C_{1-4}$alkyl;
$R^8$ is
(1) hydroxy, halogen, cyano, amino or —$C(O)R^c$,
(2) $C_{1-4}$alkyl or $C_{1-4}$alkoxyl, both of which are unsubstituted or substituted by 1-3 substitutents selected from cyano, halogen and/or hydroxy, or
(3) 5-6-membered saturated monocyclic heterocyclyl, which is unsubstituted or substituted by 1-3 substitutents selected from cyano, trifluoromethyl, halogen, —C(O)R$^{c'}$, —C(O)(CH$_2$)$_n$NR$^a$R$^b$ and/or —S(O)$_2$R$^{c'}$;
R$^{8'}$ is
(1) hydroxy, halogen, cyano, amino, —(CH$_2$)$_n$NR$^a$C(O)R$^c$ or —(CH$_2$)$_n$S(O)$_m$R$^c$,
(2) C$_{1-4}$alkyl or C$_{1-4}$alkoxyl, both of which are unsubstituted or substituted by 1-3 substitutents selected from cyano, halogen and/or hydroxy, or
(3) 5-6-membered monocyclic heterocyclyl, which is unsubstituted or substituted by cyano, trifluoromethyl, halogen, C$_{1-4}$alkyl or C$_{1-4}$alkoxyl; each of R$^a$ and R$^b$ is independently hydrogen, or C$_{1-4}$alkyl that is unsubstituted or substituted by 1-3 substitutents selected from hydroxy and/or halogen;
R$^c$ is C$_{1-4}$alkyl or C$_{1-4}$alkoxyl, both of which are unsubstituted or substituted by 1-3 substitutents selected from hydroxy, halogen and/or cyano;
R$^{c'}$ is C$_{1-4}$alkyl or C$_{1-4}$alkoxyl, both of which are unsubstituted or substituted by 1-3 substitutents selected from hydroxy and/or halogen;
m is 0, 1 or 2; and
n is 0, 1, 2 or 3.

In a further preferable embodiment of the present compound of general formula (I):
R$^1$ is phenyl, naphthyl or 5-8-membered saturated monocyclic heterocyclyl that are unsubstituted or substituted by 1-3 R$^8$;
R$^2$ is phenyl, pyridinyl, pyrimidinyl, pyridazinyl, pyrazinyl, pyrazolyl, imidazolyl, pyrrolyl, oxazolyl, isoxazolyl, thiazolyl, isothiazolyl, indazolyl, quinolinyl, isoquinolinyl, indolyl, pyrrolopyridine, dihydropyrrolopyridine or pyrazolopyridinyl, all of which are unsubstituted or substituted by 1-3 R$^8$; each of R$^3$, R$^4$ and R$^5$ is hydrogen;
each of R$^6$ and R$^7$ is independently hydrogen or methyl;
R$^8$ is
(1) amino or —C(O)R$^c$, R$^c$ is C$_{1-4}$alkyl that is unsubstituted or substituted by hydroxy or halogen,
(2) C$_{1-4}$alkyl or C$_{1-4}$alkoxyl, both of which are unsubstituted or substituted by cyano or 1-3 fluoro, or
(3) piperazinyl or piperidinyl, both of which are unsubstituted or substituted by cyano or trifluoromethyl;
R$^{8'}$ is
(1) hydroxy, halogen, amino, cyano, —NHC(O)R$^c$ or —S(O)$_m$R$^c$, wherein m is 0 or 2, R$^c$ is C$_{1-4}$alkyl,
(2) C$_{1-4}$alkyl or C$_{1-4}$alkoxyl, both of which are unsubstituted or substituted by hydroxy or 1-3 fluoro, or
(3) pyridinyl, piperidinyl, pyrimidinyl, pyridazinyl, pyrazinyl, piperazinyl, pyrazolyl, imidazolyl, pyrrolyl, pyrrolidinyl or morpholinyl, all of which are unsubstituted or substituted by cyano, trifluoromethyl, halogen, C$_{1-4}$alkyl or C$_{1-4}$alkoxyl.

In a further preferable embodiment of the present compound of general formula (I),
R$^1$ is phenyl, piperidinyl or piperazinyl, all of which are unsubstituted or substituted by 1-2 R$^8$;
R$^2$ is phenyl, pyridinyl, pyrimidinyl, pyridazinyl, pyrazinyl, pyrazolyl, imidazolyl, pyrrolyl, oxazolyl, isoxazolyl, thiazolyl, isothiazolyl, quinolinyl, isoquinolinyl, pyrrolopyridine, dihydropyrrolopyridine or indolyl, all of which are unsubstituted or substituted by 1-2 R$^8$;
each of R$^3$, R$^4$ and R$^5$ is hydrogen;
each of R$^6$ and R$^7$ is independently hydrogen or methyl;
R$^8$ is
(1) amino or —C(O)R$^c$, R$^c$ is C$_{1-4}$alkyl that is unsubstituted or substituted by hydroxy,
(2) C$_{1-4}$alkyl, which is unsubstituted or substituted by cyano or three fluoro, or
(3) piperazinyl or piperidinyl, both of which are unsubstituted or substituted by cyano or trifluoromethyl;
R$^{8'}$ is
(1) halogen, amino, cyano, —NHC(O)R$^c$ or —S(O)$_m$R$^c$, wherein m is 0 or 2, R$^c$ is C$_{1-4}$alkyl,
(2) C$_{1-4}$alkyl or C$_{1-4}$alkoxyl, both of which are unsubstituted or substituted by hydroxy or three fluoro, or
(3) piperazinyl, pyrazolyl, piperidinyl, morpholinyl, pyrimidinyl, pyridazinyl, pyrazinyl, pyrrolyl or pyrrolidinyl, all of which are unsubstituted or substituted by C$_{1-4}$alkyl.

The preferable compounds of the present invention comprise the following compounds and its pharmaceutically acceptable salt, stereoisomer and deuteride thereof:

| No. | Structure | Name |
|---|---|---|
| 1 | 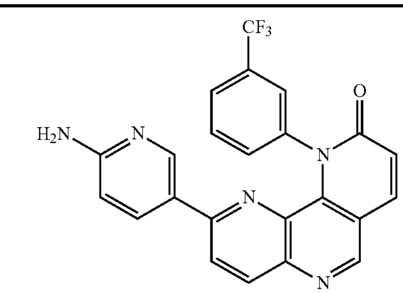 | 2-(6-aminopyridin-3-yl)-10-(3-(trifluoromethyl)phenyl)pyrido[3,2-c][1,5]naphthyridin-9(10H)-one |
| 2 | 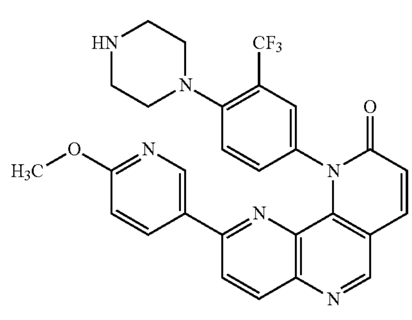 [SMILES: COc1ccc(-c2ccc3ncc4ccc(=O)n(-c5ccc(N6CCNCC6)c(C(F)(F)F)c5)c4c3n2)cn1] | 2-(6-methoxypyridin-3-yl)-10-(4-(piperazin-1-yl)-3-(trifluoromethyl)phenyl)pyrido[3,2-c][1,5]naphthyridin-9(10H)-one |

-continued

| No. | Structure | Name |
|---|---|---|
| 3 | 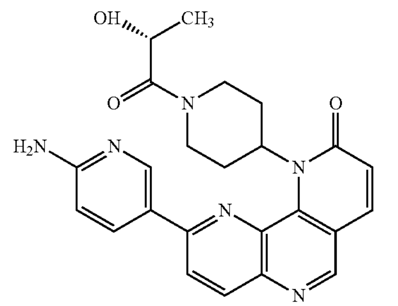 [SMILES: C[C@@H](O)C(=O)N1CCC(n2c(=O)ccc3cnc4ccc(-c5ccc(N)nc5)nc4c32)CC1] | (R)-2-(6-aminopyridin-3-yl)-10-(1-(2-hydroxypropanoyl)piperidin-4-yl)pyrido[3,2-c][1,5]naphthyridin-9(10H)-one |
| 4 | 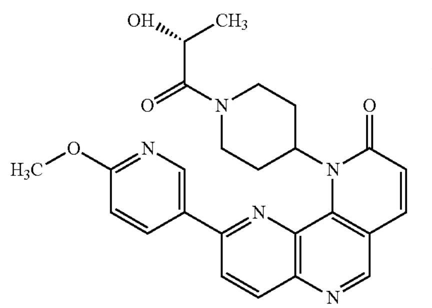 [SMILES: COc1ccc(-c2ccc3ncc4ccc(=O)n(C5CCN(C(=O)[C@@H](C)O)CC5)c4c3n2)cn1] | (R)-10-(1-(2-hydroxypropanoyl)piperidin-4-yl)-2-(6-methoxypyridin-3-yl)pyrido[3,2-c][1,5]naphthyridin-9(10H)-one |
| 5 | 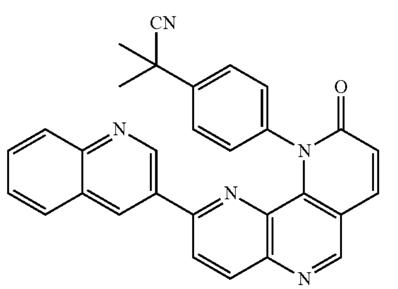 [SMILES: CC(C)(C#N)c1ccc(-n2c(=O)ccc3cnc4ccc(-c5cnc6ccccc6c5)nc4c32)cc1] | 2-methyl-2-(4-(9-oxo-2-(quinolin-3-yl)pyrido[3,2-c][1,5]naphthyridin-10(9H)-yl)phenyl)propanenitrile |
| 6 | 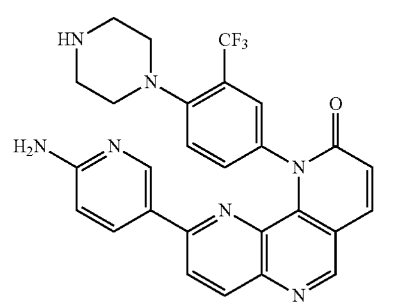 [SMILES: Nc1ccc(-c2ccc3ncc4ccc(=O)n(-c5ccc(N6CCNCC6)c(C(F)(F)F)c5)c4c3n2)cn1] | 2-(6-aminopyridin-3-yl)-10-(4-(piperazin-1-yl)-3-(trifluoromethyl)phenyl)pyrido[3,2-c][1,5]naphthyridin-9(10H)-one |
| 7 | 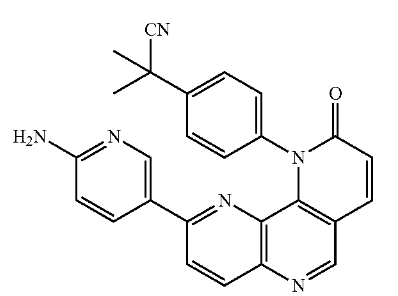 [SMILES: CC(C)(C#N)c1ccc(-n2c(=O)ccc3cnc4ccc(-c5ccc(N)nc5)nc4c32)cc1] | 2-(4-(2-(6-aminopyridin-3-yl)-9-oxopyrido[3,2-c][1,5]naphthyridin-10(9H)-yl)phenyl)-2-methylpropanenitrile |

-continued

| No. | Structure | Name |
|---|---|---|
| 8 | 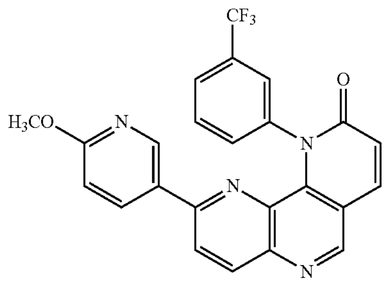 [SMILES: COc1ccc(-c2ccc3ncc4ccc(=O)n(-c5cccc(C(F)(F)F)c5)c4c3n2)cn1] | 2-(6-methoxypyridin-3-yl)-10-(3-(trifluoromethyl)phenyl)pyrido[3,2-c][1,5]naphthyridin-9(10H)-one |
| 9 | 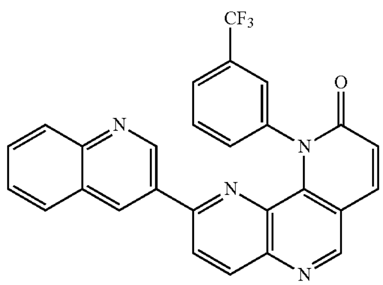 [SMILES: O=c1ccc2cnc3ccc(-c4cnc5ccccc5c4)nc3c2n1-c1cccc(C(F)(F)F)c1] | 2-(quinolin-3-yl)-10-(3-(trifluoromethyl)phenyl)pyrido[3,2-c][1,5]naphthyridin-9(10H)-one |
| 10 | 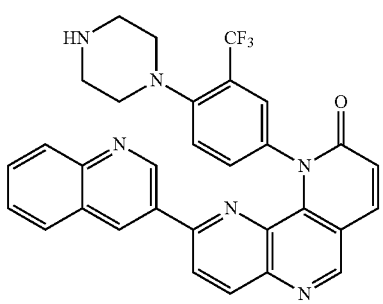 [SMILES: O=c1ccc2cnc3ccc(-c4cnc5ccccc5c4)nc3c2n1-c1ccc(N2CCNCC2)c(C(F)(F)F)c1] | 10-(4-(piperazin-1-yl)-3-(trifluoromethyl)phenyl)-2-(quinolin-3-yl)pyrido[3,2-c][1,5]naphthyridin-9(10H)-one |
| 11 | 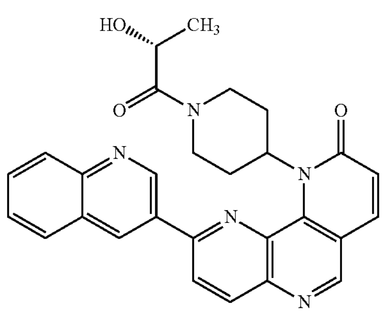 [SMILES: C[C@@H](O)C(=O)N1CCC(n2c(=O)ccc3cnc4ccc(-c5cnc6ccccc6c5)nc4c32)CC1] | (R)-10-(1-(2-hydroxypropanoyl)piperidin-4-yl)-2-(quinolin-3-yl)pyrido[3,2-c][1,5]naphthyridin-9(10H)-one |
| 12 | 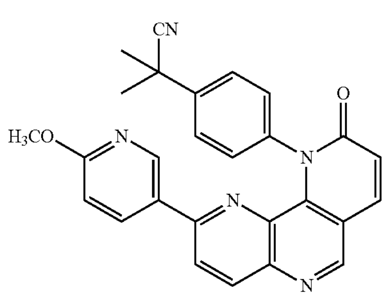 [SMILES: COc1ccc(-c2ccc3ncc4ccc(=O)n(-c5ccc(C(C)(C)C#N)cc5)c4c3n2)cn1] | 2-(4-(2-(6-methoxypyridin-3-yl)-9-oxopyrido[3,2-c][1,5]naphthyridin-10(9H)-yl)phenyl)-2-methylpropanenitrile |

-continued

| No. | Structure | Name |
|---|---|---|
| 13 | 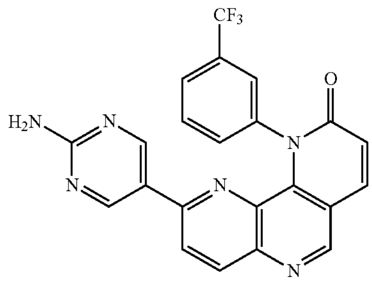 | 2-(2-aminopyrimidin-5-yl)-10-(3-(trifluoromethyl)phenyl)pyrido[3,2-c][1,5]naphthyridin-9(10H)-one |
| 14 | 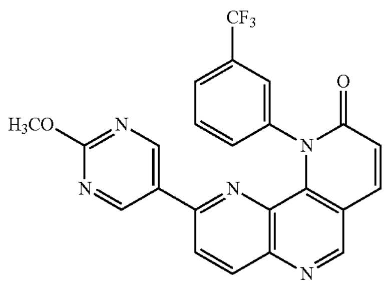 [SMILES: COc1ncc(-c2ccc3ncc4ccc(=O)n(-c5cccc(C(F)(F)F)c5)c4c3n2)cn1] | 2-(2-methoxypyrimidin-5-yl)-10-(3-(trifluoromethyl)phenyl)pyrido[3,2-c][1,5]naphthyridin-9(10H)-one |
| 15 | 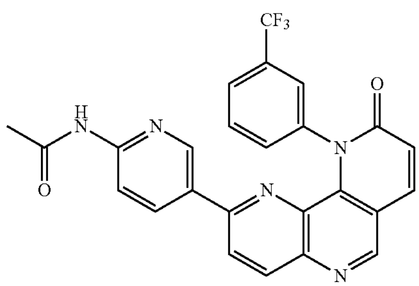 [SMILES: CC(=O)Nc1ccc(-c2ccc3ncc4ccc(=O)n(-c5cccc(C(F)(F)F)c5)c4c3n2)cn1] | N-(5-(9-oxo-10-(3-(trifluoromethyl)phenyl)-9,10-dihydropyrido[3,2-c][1,5]naphthyridin-2-yl)pyridin-2-yl)acetamide |
| 16 | 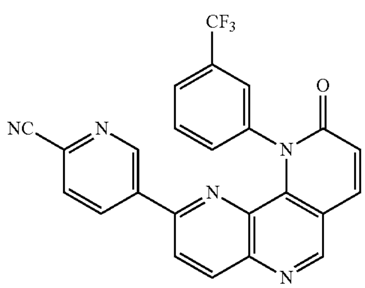 [SMILES: N#Cc1ccc(-c2ccc3ncc4ccc(=O)n(-c5cccc(C(F)(F)F)c5)c4c3n2)cn1] | 5-(9-oxo-10-(3-(trifluoromethyl)phenyl)-9,10-dihydropyrido[3,2-c][1,5]naphthyridin-2-yl)-2-cyanopyridine |
| 17 | 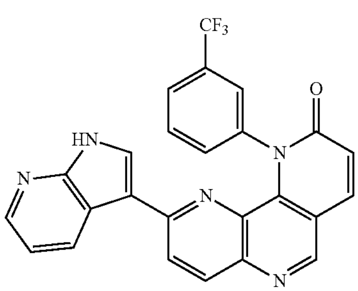 [SMILES: O=c1ccc2cnc3ccc(-c4c[nH]c5ncccc45)nc3c2n1-c1cccc(C(F)(F)F)c1] | 2-(1H-pyrrolo[2,3-b]pyridin-3-yl)-10-(3-(trifluoromethyl)phenyl)pyrido[3,2-c][1,5]naphthyridin-9(10H)-one |

| No. | Structure | Name |
|---|---|---|
| 18 | 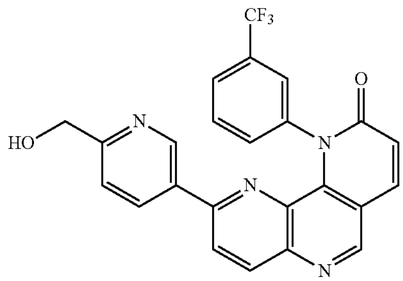 [SMILES: O=c1ccc2cnc3ccc(-c4ccc(CO)nc4)nc3c2n1-c1cccc(C(F)(F)F)c1] | 2-(6-(hydroxymethyl)pyridin-3-yl)-10-(3-(trifluoromethyl)phenyl)pyrido[3,2-c][1,5]naphthyridin-9(10H)-one |
| 19 | 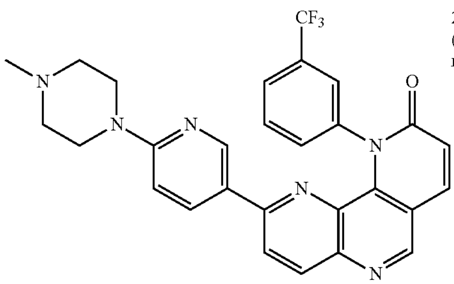 | 2-(6-(4-methylpiperazin-1-yl)pyridin-3-yl)-10-(3-(trifluoromethyl)phenyl)pyrido[3,2-c][1,5]naphthyridin-9(10H)-one |
| 20 | 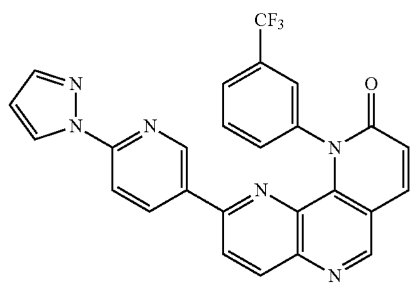 [SMILES: O=c1ccc2cnc3ccc(-c4ccc(-n5cccn5)nc4)nc3c2n1-c1cccc(C(F)(F)F)c1] | 2-(6-(1H-pyrazol-1-yl)pyridin-3-yl)-10-(3-(trifluoromethyl)phenyl)pyrido[3,2-c][1,5]naphthyridin-9(10H)-one |
| 21 | 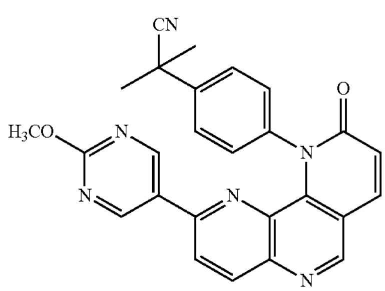 [SMILES: COc1ncc(-c2ccc3ncc4ccc(=O)n(-c5ccc(C(C)(C)C#N)cc5)c4c3n2)cn1] | 2-(4-(2-(2-methoxypyrimidin-5-yl)-9-oxopyrido[3,2-c][1,5]naphthyridin-10(9H)-yl)phenyl)-2-methylpropanenitrile |
| 22 | 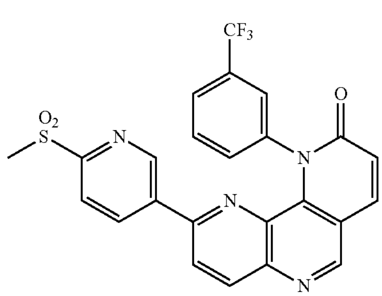 [SMILES: CS(=O)(=O)c1ccc(-c2ccc3ncc4ccc(=O)n(-c5cccc(C(F)(F)F)c5)c4c3n2)cn1] | 2-(6-(methylsulfonyl)pyridin-3-yl)-10-(3-(trifluoromethyl)phenyl)pyrido[3,2-c][1,5]naphthyridin-9(10H)-one |

-continued

| No. | Structure | Name |
|---|---|---|
| 23 | 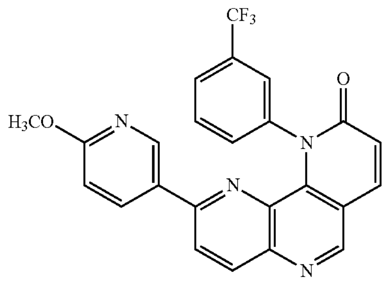 [SMILES: COc1ccc(-c2ccc3ncc4ccc(=O)n(-c5cccc(C(F)(F)F)c5)c4c3n2)cn1] | 2-(6-methoxypyridin-3-yl)-10-(3-(trifluoromethyl)phenyl)pyrido[3,2-c][1,5]naphthyridin-9(10H)-one |
| 24 | 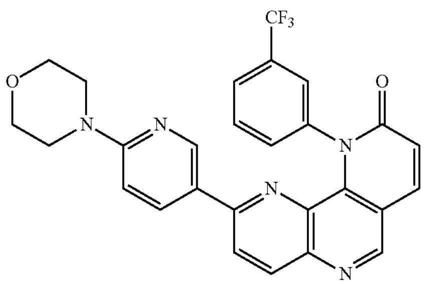 [SMILES: O=c1ccc2cnc3ccc(-c4ccc(N5CCOCC5)nc4)nc3c2n1-c1cccc(C(F)(F)F)c1] | 2-(6-morpholinopyridin-3-yl)-10-(3-(trifluoromethyl)phenyl)pyrido[3,2-c][1,5]naphthyridin-9(10H)-one |
| 25 | 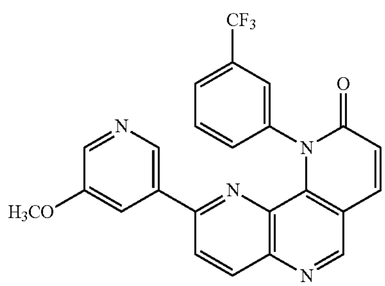 [SMILES: COc1cncc(-c2ccc3ncc4ccc(=O)n(-c5cccc(C(F)(F)F)c5)c4c3n2)c1] | 2-(5-methoxypyridin-3-yl)-10-(3-(trifluoromethyl)phenyl)pyrido[3,2-c][1,5]naphthyridin-9(10H)-one |
| 26 | 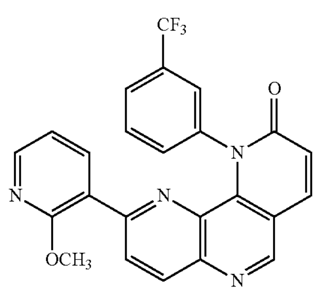 [SMILES: COc1ncccc1-c1ccc2ncc3ccc(=O)n(-c4cccc(C(F)(F)F)c4)c3c2n1] | 2-(2-methoxypyridin-3-yl)-10-(3-(trifluoromethyl)phenyl)pyrido[3,2-c][1,5]naphthyridin-9(10H)-one |
| 27 | 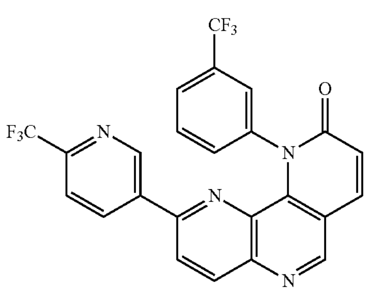 [SMILES: O=c1ccc2cnc3ccc(-c4ccc(C(F)(F)F)nc4)nc3c2n1-c1cccc(C(F)(F)F)c1] | 10-(3-(trifluoromethyl)phenyl)-2-(6-(trifluoromethyl)pyridin-3-yl)pyrido[3,2-c][1,5]naphthyridin-9(10H)-one |

| No. | Structure | Name |
|---|---|---|
| 28 | 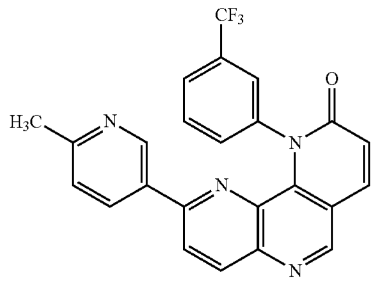 | 2-(6-methylpyridin-3-yl)-10-(3-(trifluoromethyl)phenyl)pyrido[3,2-c][1,5]naphthyridin-9(10H)-one |
| 29 | 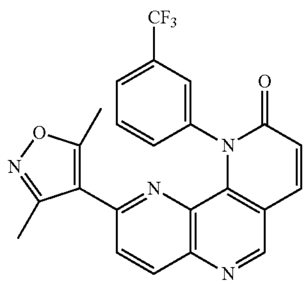 [SMILES: Cc1noc(C)c1-c1ccc2ncc3ccc(=O)n(-c4cccc(C(F)(F)F)c4)c3c2n1] | 2-(3,5-dimethylisoxazol-4-yl)-10-(3-(trifluoromethyl)phenyl)pyrido[3,2-c][1,5]naphthyridin-9(10H)-one |
| 30 | 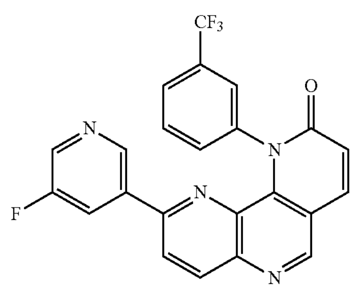 [SMILES: O=c1ccc2cnc3ccc(-c4cncc(F)c4)nc3c2n1-c1cccc(C(F)(F)F)c1] | 2-(5-fluoropyridin-3-yl)-10-(3-(trifluoromethyl)phenyl)pyrido[3,2-c][1,5]naphthyridin-9(10H)-one |
| 31 | 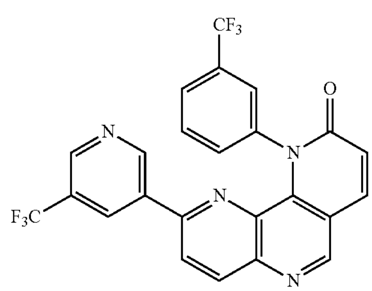 [SMILES: O=c1ccc2cnc3ccc(-c4cncc(C(F)(F)F)c4)nc3c2n1-c1cccc(C(F)(F)F)c1] | 10-(3-(trifluoromethyl)phenyl-2-(5-(trifluoromethyl)pyridin-3-yl)pyrido[3,2-c][1,5]naphthyridin-9(10H)-one |
| 32 | 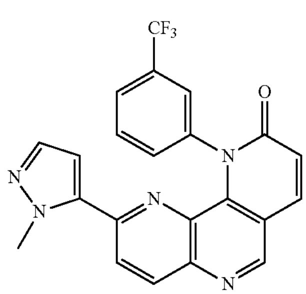 [SMILES: Cn1nccc1-c1ccc2ncc3ccc(=O)n(-c4cccc(C(F)(F)F)c4)c3c2n1] | 2-(1-methyl-1H-pyrazol-5-yl)-10-(3-(trifluoromethyl)phenyl)pyrido[3,2-c][1,5]naphthyridin-9(10H)-one |

| No. | Structure | Name |
|---|---|---|
| 33 | 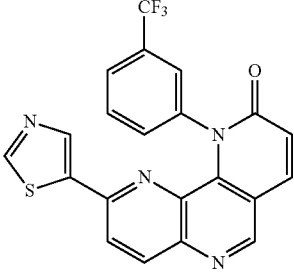 [SMILES: O=c1ccc2cnc3ccc(-c4cncs4)nc3c2n1-c1cccc(C(F)(F)F)c1] | 2-(thiazol-5-yl)-10-(3-(trifluoromethyl)phenyl)pyrido[3,2-c][1,5]naphthyridin-9(10H)-one |
| 34 | 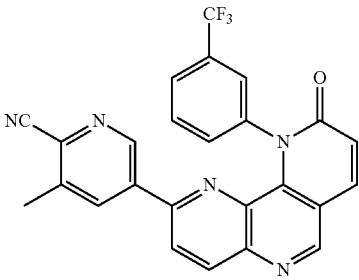 [SMILES: Cc1cc(-c2ccc3ncc4ccc(=O)n(-c5cccc(C(F)(F)F)c5)c4c3n2)cnc1C#N] | 3-methyl-5-(9-oxo-10-(3-(trifluoromethyl)phenyl)-9,10-dihydropyrido[3,2-c][1,5]naphthyridin-2-yl)-2-cyanopyridine |
| 35 | 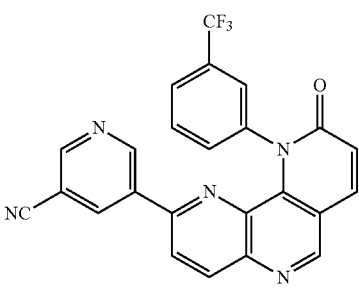 [SMILES: N#Cc1cncc(-c2ccc3ncc4ccc(=O)n(-c5cccc(C(F)(F)F)c5)c4c3n2)c1] | 5-(9-oxo-10-(3-(trifluoromethyl)phenyl)-9,10-dihydropyrido[3,2-c][1,5]naphthyridin-2-yl)-3-cyanopyridine |
| 36 | 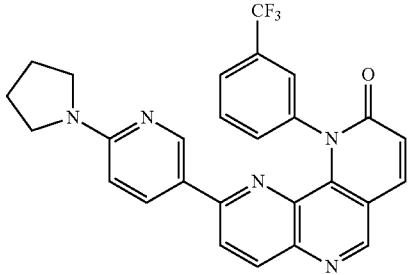 [SMILES: O=c1ccc2cnc3ccc(-c4ccc(N5CCCC5)nc4)nc3c2n1-c1cccc(C(F)(F)F)c1] | 2-(6-(pyrrolidin-1-yl)pyridin-3-yl)-10-(3-(trifluoromethyl)phenyl)pyrido[3,2-c][1,5]naphthyridin-9(10H)-one |
| 37 | 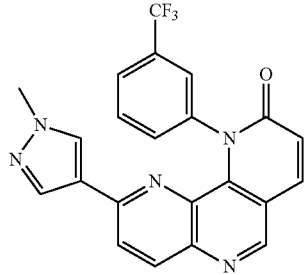 [SMILES: Cn1cc(-c2ccc3ncc4ccc(=O)n(-c5cccc(C(F)(F)F)c5)c4c3n2)cn1] | 2-(1-methyl-1H-pyrazol-4-yl)-10-(3-(trifluoromethyl)phenyl)pyrido[3,2-c][1,5]naphthyridin-9(10H)-one |

-continued

| No. | Structure | Name |
|---|---|---|
| 38 | 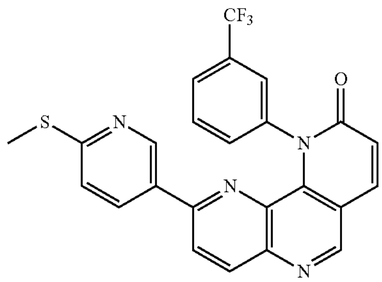 [SMILES: CSc1ccc(-c2ccc3ncc4ccc(=O)n(-c5cccc(C(F)(F)F)c5)c4c3n2)cn1] | 2-(6-(methylthio)pyridin-3-yl)-10-(3-(trifluoromethyl)phenyl)pyrido[3,2-c][1,5]naphthyridin-9(10H)-one |
| 39 | 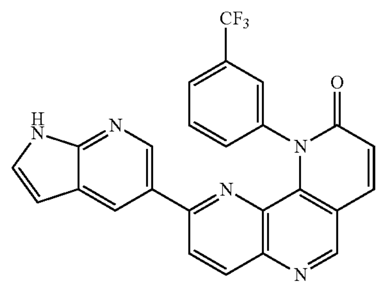 [SMILES: O=c1ccc2cnc3ccc(-c4cnc5[nH]ccc5c4)nc3c2n1-c1cccc(C(F)(F)F)c1] | 2-(1H-pyrrolo[2,3-b]pyridin-5-yl)-10-(3-(trifluoromethyl)phenyl)pyrido[3,2-c][1,5]naphthyridin-9(10H)-one |
| 40 | 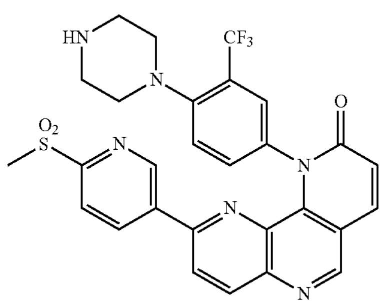 [SMILES: CS(=O)(=O)c1ccc(-c2ccc3ncc4ccc(=O)n(-c5ccc(N6CCNCC6)c(C(F)(F)F)c5)c4c3n2)cn1] | 2-(6-(methylsulfonyl)pyridin-3-yl)-10-(4-(piperazin-1-yl)-3-(trifluoromethyl)phenyl)pyrido[3,2-c][1,5]naphthyridin-9(10H)-one |
| 41 | 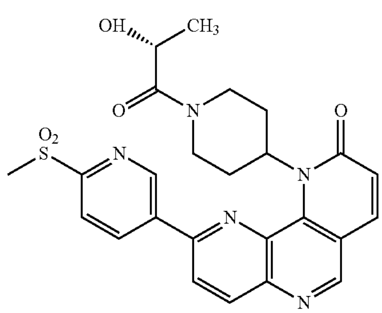 [SMILES: C[C@@H](O)C(=O)N1CCC(n2c(=O)ccc3cnc4ccc(-c5ccc(S(C)(=O)=O)nc5)nc4c32)CC1] | (R)-10-(1-(2-hydroxypropanoyl)piperidin-4-yl)-2-(6-(methylsulfonyl)pyridin-3-yl)pyrido[3,2-c][1,5]naphthyridin-9(10H)-one |
| 42 | 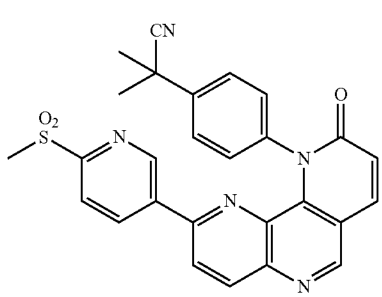 [SMILES: CC(C)(C#N)c1ccc(-n2c(=O)ccc3cnc4ccc(-c5ccc(S(C)(=O)=O)nc5)nc4c32)cc1] | 2-methyl-2-(4-(2-(6-(methylsulfonyl)pyridin-3-yl)-9-oxopyrido[3,2-c][1,5]naphthyridin-10(9H)-yl)phenyl)propanenitrile |

-continued

| No. | Structure | Name |
|---|---|---|
| 43 | 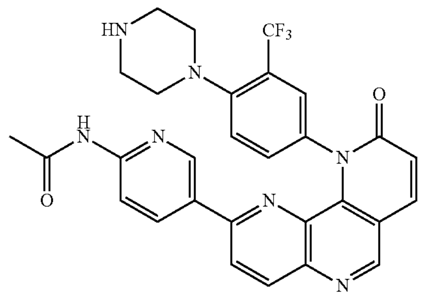 [SMILES: CC(=O)Nc1ccc(-c2ccc3ncc4ccc(=O)n(-c5ccc(N6CCNCC6)c(C(F)(F)F)c5)c4c3n2)cn1] | N-(5-(9-oxo-10-(4-(piperazin-1-yl)-3-(trifluoromethyl)phenyl)-9,10-dihydropyrido[3,2-c][1,5]naphthyridin-2-yl)pyridin-2-yl)acetamide |
| 44 | 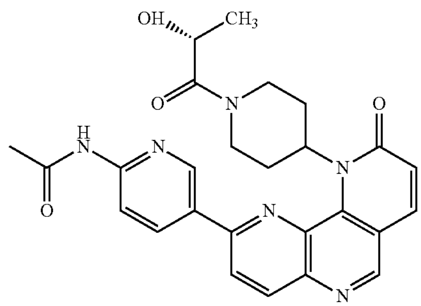 [SMILES: CC(=O)Nc1ccc(-c2ccc3ncc4ccc(=O)n(C5CCN(C(=O)[C@@H](C)O)CC5)c4c3n2)cn1] | (R)-N-(5-(10-(1-(2-hydroxypropanoyl)piperidin-4-yl)-9-oxo-9,10-dihydropyrido[3,2-c][1,5]naphthyridin-2-yl)pyridin-2-yl)acetamide |
| 45 | 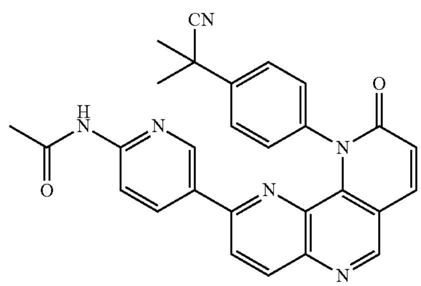 [SMILES: CC(=O)Nc1ccc(-c2ccc3ncc4ccc(=O)n(-c5ccc(C(C)(C)C#N)cc5)c4c3n2)cn1] | N-(5-(10-(4-(2-cyanopropan-2-yl)phenyl)-9-oxo-9,10-dihydropyrido[3,2-c][1,5]naphthyridin-2-yl)pyridin-2-yl)acetamide |
| 46 | 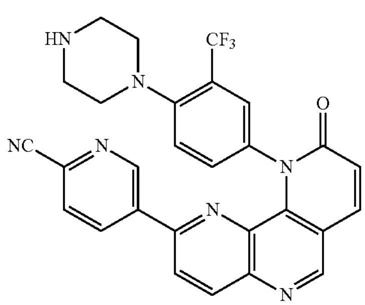 [SMILES: N#Cc1ccc(-c2ccc3ncc4ccc(=O)n(-c5ccc(N6CCNCC6)c(C(F)(F)F)c5)c4c3n2)cn1] | 5-(9-oxo-10-(4-(piperazin-1-yl)-3-(trifluoromethyl)phenyl)-9,10-dihydropyrido[3,2-c][1,5]naphthyridin-2-yl)-2-cyanopyridine |
| 47 | 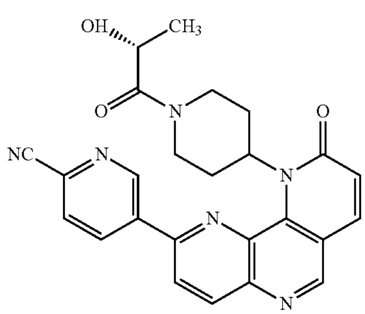 [SMILES: C[C@@H](O)C(=O)N1CCC(n2c(=O)ccc3cnc4ccc(-c5ccc(C#N)nc5)nc4c32)CC1] | (R)-(5-(10-(1-(2-hydroxypropanoyl)piperidin-4-yl)-9-oxo-9,10-dihydropyrido[3,2-c][1,5]naphthyridin-2-yl)-2-cyanopyridine |

| No. | Structure | Name |
|---|---|---|
| 48 | 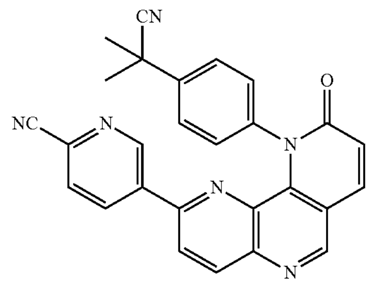 [SMILES: CC(C)(C#N)c1ccc(-n2c(=O)ccc3cnc4ccc(-c5ccc(C#N)nc5)nc4c32)cc1] | 5-(10-(4-(2-cyanopropan-2-yl)phenyl)-9-oxo-9,10-dihydropyrido[3,2-c][1,5]naphthyridin-2-yl)-2-cyanopyridine |
| 49 | 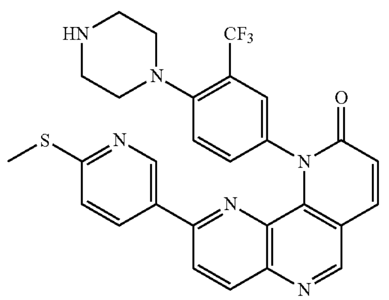 [SMILES: CSc1ccc(-c2ccc3ncc4ccc(=O)n(-c5ccc(N6CCNCC6)c(C(F)(F)F)c5)c4c3n2)cn1] | 2-(6-(methylthio)pyridin-3-yl)-10-(4-(piperazin-1-yl)-3-(trifluoromethyl)phenyl)pyrido[3,2-c][1,5]naphthyridin-9(10H)-one |
| 50 | 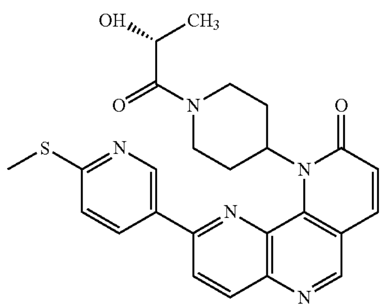 [SMILES: CSc1ccc(-c2ccc3ncc4ccc(=O)n(C5CCN(C(=O)[C@@H](C)O)CC5)c4c3n2)cn1] | (R)-10-(1-(2-hydroxypropanoyl)piperidin-4-yl)-2-(6-(methylthio)pyridin-3-yl)pyrido[3,2-c][1,5]naphthyridin-9(10H)-one |
| 51 | 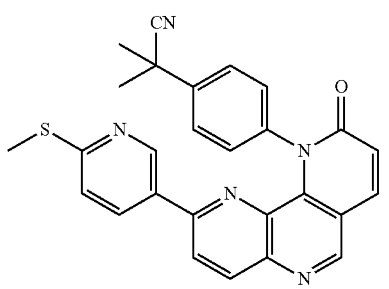 [SMILES: CSc1ccc(-c2ccc3ncc4ccc(=O)n(-c5ccc(C(C)(C)C#N)cc5)c4c3n2)cn1] | 2-methyl-2-(4-(2-(6-(methylthio)pyridin-3-yl)-9-oxopyrido[3,2-c][1,5]naphthyridin-10(9H)-yl)phenyl)propanenitrile |

In the present invention, the term "halogen" means fluoro, chloro, bromo or iodo. In the present invention, the term "$C_{1-6}$alkyl" means a straight-chain or branched chain alkyl containing 1-6 carbon atoms, wherein including, for example "$C_{1-4}$alkyl", "$C_{2-5}$alkyl", "$C_{1-3}$alkyl" and the like; its example includes but is not limited to, for example, methyl, ethyl, n-propyl, iso-propyl, n-butyl, 2-methylpropyl, 1-methylpropyl, 1,1-dimethylethyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like.

In the present invention, the term "$C_{2-6}$alkenyl" means a straight-chain, branched chain or cyclic hydrocarbonyl containing 2-6 carbon atoms and double bond(s), wherein including for example "$C_{2-4}$alkenyl", "$C_{2-5}$alkenyl", "$C_{2-3}$alkenyl", $C_{3-6}$cycloalkenyl and the like; its example includes but is not limited to, for example, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-2-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1,3-butadiene, 1,3-pentadiene, 1,4-pentadiene, 1,4-hexadiene and the like. The example of said "$C_{3-6}$cycloalkenyl" includes but is not limited to, for example, cyclopropenyl, cyclobutenyl, cyclopentenyl, 1,3-cyclopentadienyl, cyclohexenyl, 1,4-cyclohexadienyl and the like.

In the present invention, the term "$C_{2-6}$alkynyl" means a straight-chain, or branched chain hydrocarbonyl containing 2-6 carbon atoms and triple bond(s), wherein including for example "$C_{2-4}$alkynyl", "$C_{2-5}$alkynyl", "$C_{2-3}$alkynyl" the like; its example includes but is not limited to, for example, ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl, 1-ethyl-1-methyl-2-propynyl and the like. In the present invention, the term "$C_{1-6}$alkoxy" means a "$C_{1-6}$alkyl-O-" group, wherein $C_{1-6}$alkyl is defined as hereinbefore, wherein including for example "$C_{1-4}$alkoxyl", "$C_{2-5}$alkoxyl", "$C_{1-3}$alkoxyl" and the like; its example includes but is not limited to, for example, methoxy, ethoxy, propoxy, isopropoxy, butoxy, isobutoxy, tert-butoxy, sec-butoxy, pentyloxy, neo-pentyloxy, hexyloxy, and the like.

In the present invention, the term "3-14-membered cycloalkyl" means a cycloalkyl having 3-14 carbon atoms, wherein including for example "3-12-membered cycloalkyl", "5-10-membered cycloalkyl", "3-8-membered cycloalkyl", "3-6-membered cycloalkyl", "5-8-membered cycloalkyl" and the like; also including "3-8-membered monocyclic cycloalkyl" and "6-14-membered fused cycloalkyl".

Said "3-8-membered monocyclic cycloalkyl" means monocycloalkyl having 3-8 carbon atoms, wherein including for example "3-6-membered monocyclic cycloalkyl", "5-8-membered monocyclic cycloalkyl", "5-6-membered monocyclic cycloalkyl" and like; its example includes but is not limited to: cyclopropyl, cyclobutyl, cyclopentyl, cyclohexyl, cycloheptyl, cyclooctanyl and the like; said 3-8-membered monocyclic cycloalkyl can also be further substituted by $C_{1-6}$alkyl, including but being not limited to, methylcyclopropyl, dimethylcyclopropyl, methylcyclobutyl, dimethylcyclobutyl, methylcyclopentyl, dimethylcyclopentyl, methylcyclohexyl, dimethylcyclohexanyl and the like.

Said "6-14-membered fused cycloalkyl" means a fused cycloalkyl group, which is formed by two or more cyclic structures in said fused ring via sharing two adjacent carbon atoms with each other, wherein including for example "6-12-membered fused cycloalkyl", "8-12-membered fused cycloalkyl", "7-10-membered fused cycloalkyl" and the like; its example includes but is not limited to: dicyclo[3.1.0]hexyl, dicyclo[4.1.0]heptyl, dicyclo[2.2.0]hexyl, dicyclo[3.2.0]heptyl, dicyclo[4.2.0]octyl, octahydro-1H-indenyl, decahydronaphthalenyl, tetradecahydrophenanthrenyl and the like.

In the present invention, the term "6-14-membered aryl" means an aromatic group having 6-14 carbon atoms, wherein including for example "6-10-membered aryl" and the like; also including "6-8-membered monocyclic aryl" and "8-14-membered fused aryl".

Said "6-8-membered monocyclic aryl" includes, for example, phenyl, cyclooctatetraenyl and the like.

Said "8-14-membered fused aryl" means a fused-ring group, which has 8-14 carbon atoms and is formed by two or more cyclic structures via sharing two adjacent carbon atoms with each other, and in which at least one ring is aromatic, wherein including 10-14-membered fused aryl wherein all of the rings are aromatic rings, for example naphthyl, phenanthrenyl and the like, also including 8-14-membered fused aryl wherein a part of the rings are aromatic rings, for example benzene-fused 3-8-membered monocyclic cycloalkyl, benzene-fused $C_{3-6}$cycloalkenyl and the like. Its specific example includes but is not limited to, for example, 2,3-dihydro-1H-indenyl, 1H-indenyl, 1,2,3,4-tetrahydronaphthyl, 1,4-dihydronaphthyl and the like.

In the present invention, the term "7-12-membered bridged ring group" means an aliphatic cyclic hydrocarbyl containing 7-12 ring atoms, which is formed via any two rings sharing two indirectly attached atoms, wherein all of said ring atoms can be carbon atoms, or said ring atoms can contain at least one heteroatom selected from N, O and S and the like. Said "7-12-membered bridged ring group" includes "7-12-membered saturated bridged group" and "7-12-membered non-saturated bridged ring group".

Said "7-12-membered saturated bridged ring group" means all of the rings in the bridged ring group are saturated cyclic groups, wherein including for example "7-10-membered saturated bridged ring group", "7-8-membered saturated bridged ring group" and the like; its specific example includes but is not limited to, for example, the following bridged ring groups:

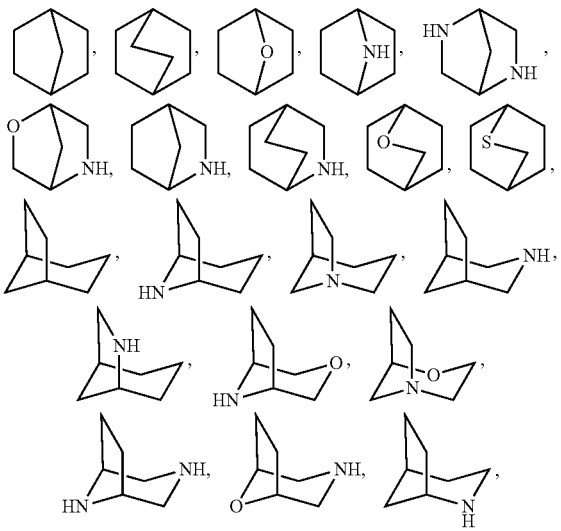

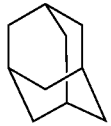

and the like; preferably 7-8-membered saturated bridged ring group.

Said "7-12-membered non-saturated bridged ring group" means a cyclic group, in which at least one ring is non-saturated, wherein including for example "7-10-membered non-saturated bridged ring group", "7-8-membered non-saturated bridged ring group" and the like; its specific example includes but is not limited to, for example, the following bridged ring groups:

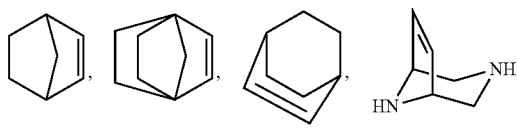

and the like; preferably 7-8-membered non-saturated bridged ring group.

In the present invention, the term "7-12-membered spiro ring group" means an aliphatic cyclic hydrocarbyl that is formed via at least two rings sharing one atom and has 7-12 ring atoms; All of the ring atoms can be carbon atoms, or the ring atom contains at least one heteroatom selected from N, O, S and the like; wherein including for example "7-11-membered spiro ring group", "8-11-membered spiro ring group", "9-10-membered spiro ring group" and the like, also including "7-12-membered saturated spiro ring group" and "7-12-membered non-saturated spiro ring group".

Said "7-12-membered saturated spiro ring group" means all of the rings in said spiro ring group are saturated rings; wherein including for example "7-11-membered saturated spiro ring group", "8-11-membered saturated spiro ring group", "9-10-membered saturated spiro ring group" and the like; its specific example includes but is not limited to, for example, the following spiro ring groups:

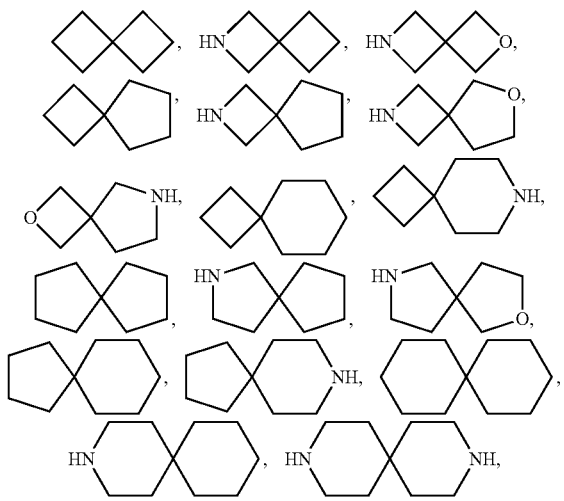

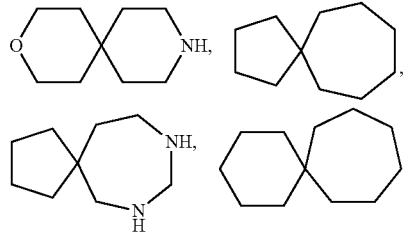

and the like.

Said "7-12-membered non-saturated spiro ring group" means at least one ring in said spiro ring group is/are non-saturated ring(s), wherein including for example "7-11-membered non-saturated spiro ring group", "8-11-membered non-saturated spiro ring group", "9-10-membered non-saturated spiro ring group" and the like; its specific example includes but is not limited to, for example, the following spiro ring groups:

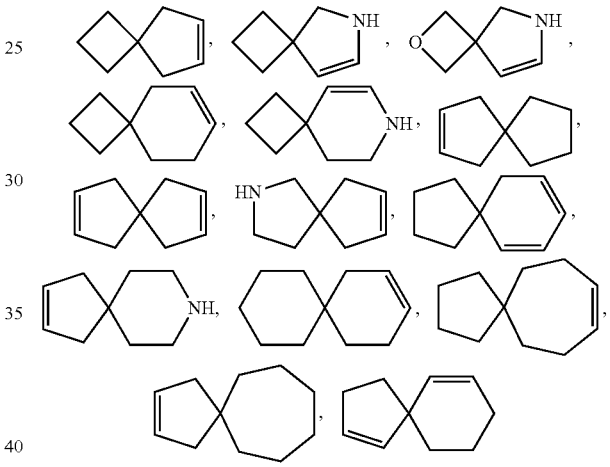

and the like.

In the present invention, the term "3-14-membered heterocyclyl" means a cyclic group containing 3-14 ring atoms (wherein containing at least one hetero atom), wherein including for example "3-8-membered heterocyclyl", "4-12-membered heterocyclyl", "5-10-membered heterocyclyl", "5-8-membered heterocyclyl", "5-6-membered heterocyclyl", and the like, also including "3-8-membered monocyclic heterocyclyl" and "6-14-membered fused heterocyclyl", wherein said hetero atom is selected from N, O, S and the like.

Said "3-8-membered monocyclic heterocyclyl" means a monocyclic heterocyclyl containing 3-8 ring atoms (wherein containing at least one hetero atom), wherein including for example "5-8-membered monocyclic heterocyclyl", "5-6-membered monocyclic heterocyclyl" and the like, also including "5-8-membered aromatic monocyclic heterocyclyl", "3-8-membered partially saturated monocyclic heterocyclyl" and "3-8-membered saturated monocyclic heterocyclyl".

Said "5-8-membered aromatic monocyclic heterocyclyl" means an aromatic cyclic group containing at least one hetero atom, wherein including for example "5-6-membered aromatic monocyclic heterocyclyl", "5-7-membered aromatic monocyclic heterocyclyl" and the like; its specific example includes but is not limited to, for example, furyl, thienyl, pyrrolyl, thiazolyl, thiodiazolyl, oxazolyl, oxdiazolyl, imidazolyl, pyrazolyl, pyridinyl, pyrimidinyl, 1,4-dioxinyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,2,4-triazinyl, 1,3,5-triazinyl, 1,2,4,5-tetrazinyl, oxepinyl, thiepinyl, azepinyl, 1,3-diazepinyl, azocinyl and the like.

Said "3-8-membered partially saturated monocyclic heterocyclyl" means a monocyclic heterocyclyl containing a double bond, wherein including for example "5-8-membered partially saturated monocyclic heterocyclyl", "5-6-membered partially saturated monocyclic heterocyclyl" and the like; its specific example includes but is not limited to, for example, 2,5-dihydrothienyl, 4,5-dihydropyrazolyl, 3,4-dihydro-2H-pyranyl, 5,6-dihydro-4H-1,3-oxazinyl and the like.

Said "3-8-membered saturated monocyclic heterocyclyl" means a monocyclic heterocyclyl, in which all of bonds are saturated, wherein including for example "5-8-membered saturated monocyclic heterocyclyl", "5-6-membered saturated monocyclic heterocyclyl", "3-6-membered saturated monocyclic heterocyclyl" and the like; its specific example includes but is not limited to, for example, aziridinyl, azetidinyl, thietanyl, tetrahydrofuryl, tetrahydropyrrolyl, imidazolidinyl, pyrazolidinyl, tetrahydrofuryl, 1,4-dioxanyl, 1,3-dioxanyl, 1,3-dithianyl, morpholinyl, piperazinyl and the like.

Said "6-14-membered fused heterocyclyl" means a fused heterocyclyl, which contains 6-14 ring atoms (wherein containing at least one hetero atom), and which is formed by linking via two or more cyclic structures sharing two adjacent atoms with each other, wherein including for example "8-12-membered fused heterocyclyl", "7-10-membered fused heterocyclyl", "9-10-membered fused heterocyclyl", "9-12-membered fused heterocyclyl" and the like, also including "8-14-membered aromatic fused heterocyclyl", "6-14-membered partially saturated fused heterocyclyl" and "6-14-membered saturated fused heterocyclyl".

Said "8-14-membered aromatic fused heterocyclyl" means a fused heterocyclyl, in which all of rings are aromatic rings, wherein including for example "8-12-membered aromatic fused heterocyclyl", "9-10-membered aromatic fused heterocyclyl", "10-14-membered aromatic fused heterocyclyl" and the like, for example, a fused heterocyclyl formed by fusing benzene with 5-8-membered aromatic monocyclic heterocyclyl, a fused heterocyclyl formed by fusing 5-8-membered aromatic monocyclic heterocyclyl with 5-8-membered aromatic monocyclic heterocyclyl and the like; its specific example includes but is not limited to, for example, benzofuryl, benzoisofuryl, benzothienyl, indolyl, benzoxazolyl, benzimidazolyl, indazolyl, benzotriazolyl, quinolinyl, isoquinolinyl, pyridopyrazolyl, pyridopyrrolyl, pyrimidinopyrazolyl, pyrimidinopyrrolyl, pyridazinopyrazolyl, pyridazinopyrrolyl, acridinyl, phenanthridinyl, benzopyridazinyl, phthalazinyl, quinazolinyl, quinoxalyl, phenazinyl, pteridinyl, purinyl, naphthyridinyl and the like.

Said "6-14-membered partially saturated fused heterocyclyl" means a fused heterocyclyl containing at least one partially saturated ring or aromatic ring, for example, a group formed by fusing benzene with 3-8-membered partially saturated monocyclic heterocycle, a group formed by fusing 3-8-membered partially saturated monocyclic heterocyclyl with 3-8-membered saturated monocyclic heterocyclyl, a group formed by fusing 3-8-membered partially saturated monocyclic heterocyclyl with 3-8-membered partially saturated monocyclic heterocyclyl and the like, a group formed by fusing 3-8-membered partially saturated monocyclic heterocyclyl with 3-8-membered monocyclic cycloalkyl, a group formed by fusing 5-6-membered aromatic monocyclic heterocyclyl with 3-8-membered monocyclic cycloalkyl, a group formed by fusing 5-6-membered aromatic monocyclic heterocyclyl with 3-8-membered partially saturated monocyclic heterocyclyl and the like; its specific example includes but is not limited to, for example, 1,3-dihydrobenzofuryl, benzo[d][1,3]dioxolyl, isoindolinyl, chromanyl, 1,2,3,4-tetrahydropyrrolo[3,4-c]pyrrolyl, dihydropyrrolopyridinyl, dihydropyrrolopyrimidinyl, dihydropyrrolopyridazinyl, tetrahydropyrrolopyridinyl, tetrahydropyrrolopyrimidinyl, tetrahydropyrrolopyridazinyl and the like.

Said "6-14-membered saturated fused heterocyclyl" means a fused heterocyclyl, in which all of rings are saturated, for example, a group formed by fusing 3-8-membered saturated monocyclic heterocyclyl with 3-8-membered saturated monocyclic heterocyclyl, a group formed by fusing 3-8-membered saturated monocyclic cycloalkyl with 3-8-membered saturated monocyclic heterocyclyl and the like; its specific example includes but is not limited to, for example, cyclobutane-fused tetrahydropyrrolyl cyclopentane-fused tetrahydropyrrolyl azetidine-fused imidazolidinyl and the like.

In an embodiment of the preparation method of the present compound of general formula (I), the compound of general formula (I) wherein $R^6$=H can be prepared, for example, according to the specific processes as illustrated in the following scheme:

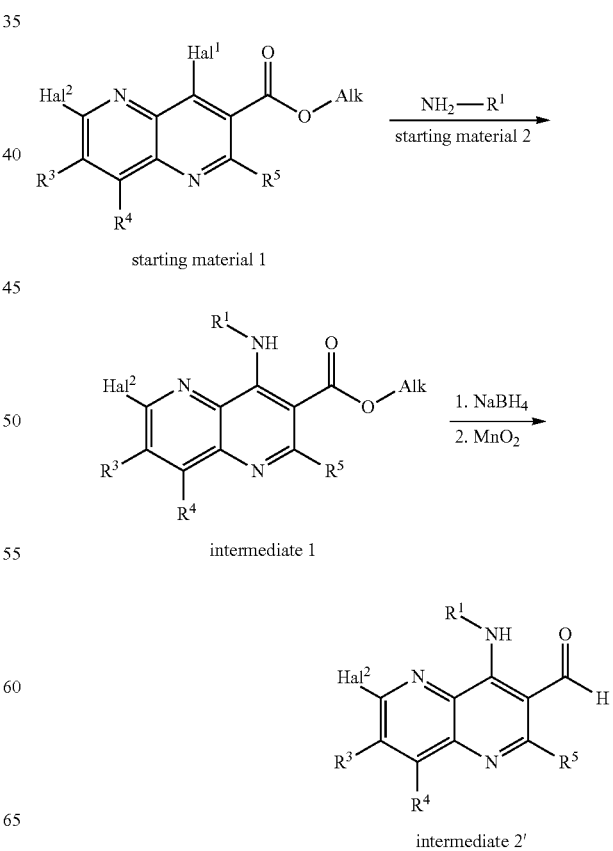

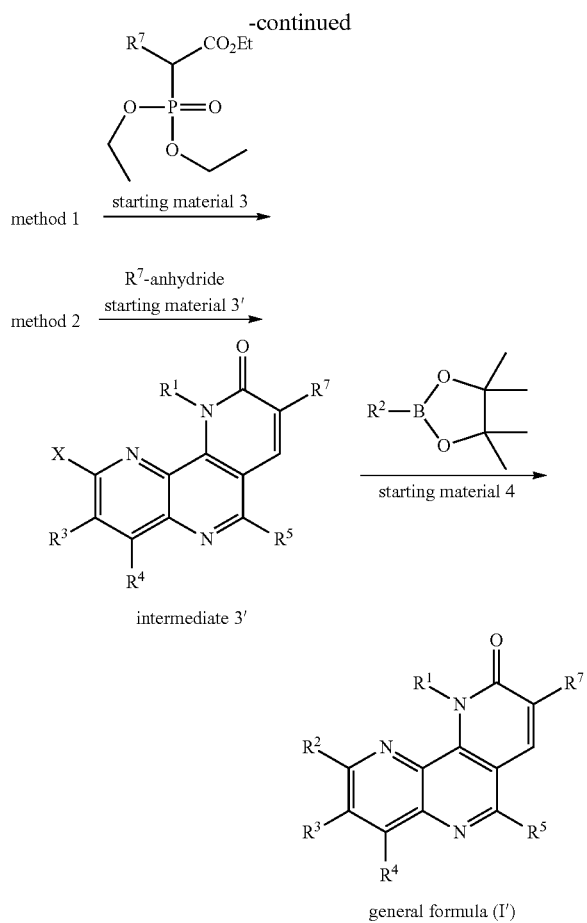

wherein $R^1$, $R^2$, $R^3$, $R^4$, $R^5$ and $R^7$ are defined as hereinbefore, $Hal^1$ and $Hal^2$ represent halogen, which is each independently selected from the group consisting of F, Cl, Br and I, and $Hal^1$ and $Hal^2$ can be identical or different; Alk represents a lower alkyl, e.g. "$C_{1-6}$alkyl", preferably "$C_{1-4}$alkyl" and more preferably ethyl; "anhydride" is preferably an organic acid anhydride, for example, selected from but not limited to acetic anhydride, propionic anhydride, preferably acetic anhydride;

1. Preparation of Intermediate 1

Starting Material 1 and Starting Material 2 are dissolved in an alcohol organic solvent (which includes but is not limited to, for example, methanol, ethanol, isopropanol or t-butanol and the like, preferably ethanol and t-butanol). To the system is added a base (which includes an organic base and an inorganic base, preferably inorganic base, and which includes but is not limited to, for example, potassium hydroxide, sodium hydroxide, zinc hydroxide, calcium hydroxide, potassium carbonate, potassium bicarbonate, sodium carbonate or sodium bicarbonate and the like, preferably potassium carbonate and sodium carbonate). The reaction is conducted under heating to reflux with stirring until the starting material disappearance to produce Intermediate 1;

2. Preparation of Intermediate 2'

Intermediate 1 is added to an alcohol organic solvent (which includes but is not limited to, for example, methanol, ethanol, isopropanol or t-butanol and the like). To the mixture is added an reductant (preferably metal hydride, which includes but is not limited to, for example, sodium borohydride, lithium aluminum hydride or diborane and the like) to conduct a reduction reaction. The solvent is removed under a reduced pressure. To the resulting residue is added water. The resulting mixture is extracted with a halogenating hydrocarbon organic solvent (which includes but is not limited to, for example, chlorobenzene, dichlorobenzene, chloromethane or dichlormethane and the like). The organic phase is dried with a neutral drying agent (which is selected from, for example, but not limited to anhydrous calcium sulphate, anhydrous sodium sulfate or anhydrous magnesium sulfate and the like, preferably anhydrous sodium sulfate), and concentrated. To the resulting concentrated liquor is added an oxidant (which is selected from, for example, but not limited to potassium permanganate, potassium chlorate, manganese dioxide or ferric chloride and the like) in batch. The reaction is conducted with stirring to produce Intermediate 2';

3. Preparation of Intermediate 3'

Method 1: To a solution of Intermediate 2' and Starting Material 3 in an alcohol organic solvent (which is selected from, for example, but not limited to methanol, ethanol, isopropanol or t-butanol and the like) in a sealed vessel, is added an inorganic base (which is selected from, for example, but not limited to potassium hydroxide, sodium hydroxide, zinc hydroxide, calcium hydroxide, potassium carbonate, potassium bicarbonate, sodium carbonate or sodium bicarbonate and the like). The reaction was conducted at 130-160° C. to produce Intermediate 3; or Method 2: Intermediate 2' is dissolved in a non protonic polar organic solvent (which is selected from, for example, but not limited to N,N-dimethylacetamide, N,N-dimethyl formamide, dimethyl sulfoxide or acetonitrile and the like) and Starting Material 3'. The reaction mixture is reacted in a microwave reactor until the starting material disappearance to produce Intermediate 3; and 4. Preparation of Formula (I')

Intermediate 3', and Starting Material 4 are dissolved in an organic solvent [selected from "an alcohol organic solvent (which includes but is not limited to, for example, methanol, ethanol, isopropanol or t-butanol and the like)", "an aromatic hydrocarbon organic solvent (which includes but is not limited to, for example, benzene, toluene or xylene and the like)" or a mixture thereof]. To the reaction system is added a solution of a catalyst (which is selected from, for example, but not limited to nickel catalyst, palladium catalyst, platinum catalyst or metal hydride catalyst and the like) and a base (e.g. potassium hydroxide, sodium hydroxide, zinc hydroxide, calcium hydroxide, potassium carbonate, potassium bicarbonate, sodium carbonate or sodium bicarbonate and the like). The resulting mixture is reacted under reflux in a nitrogen-protecting atmosphere to produce the compound of formula (I);

If necessary, a functional group that needs to be protected, such as hydroxy, amino and the like, can be protected; and afterwards can be deprotected according to the conventional method.

"A pharmaceutically acceptable salt" of the present compound of general formula (I) means a salt formed from an acidic functional group (e.g. —COOH, —OH, $SO_3H$ and the like) present in the compound of general formula (I) and a suitable inorganic or organic cationic ion (base), including, a salt formed with an alkali metal such as Na, K and the like, a salt formed with an alkaline-earth metal such as Ca, Mg and the like, an ammonium salt, and a salt formed with a nitrogen-containing organic base, wherein said organic base includes but is not limited to, for example, trimethylamine, triethylamine, tributylamine, pyridine, N,N-dimethylphenylamine, N-methylpiperidine, N-methylmorpholine, diethylamine, dicyclohexylamine, procaine, dibenzylamine, N-benzyl-β-benzeneethylamine, 1-diphenylhydroxymethylamine, N,N'-dibenzylethylenediamine and the like; and a salt formed from a basic functional group (e.g. —NH$_2$ and the like) present in the compound of general formula (I) and a suitable inorganic or organic anionic ion (acid), including, a salt formed with an inorganic acid, such as hydrochloride, hydrobromide, sulfate and the like, a salt formed with an organic carboxylic acid, such as tartrate, formate, acetate, lactate, citrate, trichloroacetate, trifluoroacetate and the like, a salt formed with sulfonic acid, such as mesylate, benzenesulphonate, para-tosylate, napsylatenapsylate and the like.

The "stereoisomer" of the present compound of general formula (I) means all of possible stereoisomers caused in case that an asymmetric carbon atom or a carbon-carbon double bond is present in the compound of general formula (T), which includes enantiomer, diastereoisomer, racemate, cis-/trans-isomer, tautomer, geometric isomer, epimer and a mixture thereof, all of which fall into the scope of the present invention.

The present invention includes the "deuteride" of the compound of general formula (I), in case that the hydrogen atom in the compound is replaced in part or in a whole with its isotope deuterium (marked as D). The resulting deuteride compound also falls in the scope of the present invention.

The present compound of general formula (I) and its pharmaceutically acceptable salt, stereoisomer and deuteride thereof can be administrated, for example, orally, parenterally (intravenously, intramuscularly, subcutaneously or rectally, and the like), pulmonarily, topically to a mammal e.g. human being. The daily dosage of the present compound can be in a range of about 20 mg-500 mg, preferably 50-300 mg.

The present compound of general formula (I), and its pharmaceutically acceptable salt, stereoisomer or deuteride thereof and one or more pharmaceutically acceptable carriers can be combined to form a pharmaceutically acceptable pharmaceutical formulation for oral, parenteral administration and the like to a patient in need thereof.

For the oral administration, the present compound of general formula (I), and its pharmaceutically acceptable salt, stereoisomer or deuteride thereof can be mixed with conventional filler, binder, disintegrant, lubricant and/or diluent and the like to formulate into a conventional solid preparation, such as tablet, capsule, pill, granule and the like; or an oral liquid preparation, such as an oral solution, an oral suspension, a syrup and the like. For the parenteral administration, the present compound of general formula (I), and its pharmaceutically acceptable salt, stereoisomer or deuteride thereof can be formulated into an injectable preparation, including an injection solution, a sterile injection powder and a concentrated injection solution. For preparing the injectable preparation, a conventional method in the pharmaceutical production can be used. For preparing the injectable preparation, an additive can be optionally added, depending on the nature of drug. The additive includes an osmotic regulator, a pH-value regulator, a solubilizer, a filler, an antioxidant, a bacteriostatic agent, an emulsifier, a suspending agent or the like.

The present compound of general formula (I), and its pharmaceutically acceptable salt, stereoisomer or deuteride thereof can be used to treat and/or prevent a proliferative disease, and can be administrated or used in combination with one or more other therapeutical agent(s), in particular, an antineoplastic agent and an immunosuppressive agent, said antineoplastic agent and said immunosuppressive agent are selected from antimetabolite, including but being not limited to capecitabine, gemcitabine, pemetrexed disodium; growth factor inhibitor, including but being not limited to pazopanib, imatinib, erlotinib, lapatinib, geftinat, vandetanib; antibody, including but being not limited to herceptin, bevacizumab; mitotic inhibitor, including but being not limited to paclitaxel, vinorelbine, docetaxel, doxorubicin; antineoplastic hormone, including but being not limited to letrozole, tamoxifen, fulvestrant, flutamide, triptorelin; alkylating agent, including but being not limited to cyclophosphamide, chlormethine, melphalan, chlorambucil, carmustine; metallic platinum, including but being not limited to carboplatin, cisplatin, oxaliplatin; topoismerase inhibitor, including but being not limited to topotecan, camptothecin, topotecan, irinotecanpto; immunosuppressive agents, including but being not limited to everolimus, sirolimus, torisel; purine analogues, including but being not limited to 6-mercaptopurine, 6-thioguanine, azathioprine; antibiotics, including but being not limited to actinomycin D, daunorubicin, adriamycin, mitoxantrone, bleomycin, plicamycin; platinum complex, including but being not limited to cisplatin, carboplatin; adrenal cortex inhibitors, including but being not limited to aminoglutethimide and the like. All of components to be administered or used in combination can be administered at the same time or successively and separately in a form of the single formulation or in a combination of the divided formulations.

The present invention also involves the use of a compound of general formula (I), and its pharmaceutically acceptable salt, stereoisomer or deuteride thereof in the manufacture of a medicament for treating and/or preventing a proliferative disease.

Said proliferative disease includes a cancer and a non-carcinomatous proliferative disease. Said cancer is selected from cerebroma, lung cancer, non-small cell lung cancer, squamous epithelial cell carcinoma, bladder carcinoma, gastric cancer, ovarian cancer, peritoneal cancer, pancreatic cancer, mammary cancer, head and neck cancer, cervical cancer, endometrial cancer, colorectal cancer, liver cancer, renal carcinoma, adenocarcinoma of esophagus, esophageal squamous cell cancer, solid tumor, non-Hodgkin lymphoma, glioma, glioblastoma multiforme, glioma sarcomatosum, prostate carcinoma, thyroid carcinoma, female genital tract cancer, carcinoma in situ, lymphoma, histiocytic lymphoma, neurofibromatosis, osteocarcinoma, cutaneous carcinoma, brain cancer, colon carcinoma, testis carcinoma, small cell lung cancer, gastrointestinal stromal tumor, prostate tumor, mast cell tumor, multiple myeloma, melanoma, neurogliocytoma, glioblastoma, astrocytoma, neuroblastoma, sarcoma and the like; said non-carcinomatous proliferative disease is selected from, for example, skin or prostate benign proliferations and the like.

It is demonstrated by experiment that the present compound is a dual PI3K and mTOR inhibitor, having an excellent antineoplastic effect; a good therapeutic effect on a proliferative disease; and a good pharmacokinetic characteristic.

SPECIFIC EMBODIMENTS

Hereinafter, the present invention will be further illustrated in details by the following specific examples. It should be understood that the scope of the present invention is not limited by the following examples.

I. Preparation Examples for the Present Compound

(I) Preparation of ethyl 4,6-dichloro-1,5-naphthyridine-3-carboxylate (starting material)

It was prepared according to the method disclosed in WO2010/038165 A1 as follows:

1. Preparation of 6-bromopyridine-3-amine

To a solution of 2-bromo-5-nitropyridine (64 g, 0.317 mol)/ethanol (1 L) was successively added Fe powder (88 g, 1.571 mmol), concentrated hydrochloric acid (61 mL) and water (287 mL). The reaction mixture was reacted under reflux for 5 h. The reaction mixture was cooled and filtered. The filtrate was concentrated and adjusted with a sodium bicarbonate solution to pH≈7-8, and re-filtered. The resulting filtrate was extracted with dichlormethane. The organic phase was dried with anhydrous sodium sulfate, and concentrated in a reduced pressure to produce 40.5 g of the title compound as a pale-yellow solid in a yield of 74.4%.

2. Preparation of diethyl 2-((6-bromopyridine-3-ylamino)methylene)malonate 6-bromopyridine-3-amine (74 g, 0.43 mol) and diethyl ethoxymethylenemalonate (100 mL) were added ethanol (680 mL). The mixture is reacted under heating to reflux for 5 h. The reaction mixture was cooled. The solid was separated out and filtered by suction. The resulting solid was washed with petroleum ether to produce 125.4 g of the title compound as a pale-yellow solid in a yield of 85.2%.

3. Preparation of ethyl 6-bromo-4-hydroxy-1,5-naphthyridine-3-carboxylate

To a boiling diphenylether (214 mL) was added diethyl (2-((6-bromopyridine-3-ylamino)methylene)malonate (40 g, 0.117 mol) in 5 mins in batch. The mixture was heated to reflux for 45 mins and TLC (ethyl acetate:petroleum ether=1:3) showed the starting material disappearance. The reaction mixture was cooled and poured into petroleum ether. The solid was separated out and filtered by suction to produce 24.6 g of the title compound as an earthy yellow solid in a yield of 71.2%.

4. Preparation of ethyl 4,6-dichloro-1,5-naphthyridine-3-carboxylate ethyl 6-bromo-4-hydroxy-1,5-naphthyridine-3-carboxylate (49.8 g, 0.168 mmol) and N,N-dimethylamine (8 mL) were added tophosphorus oxychloride (400 mL). The mixture was heated to reflux for 3 h. The reaction mixture was cooled. Phosphorus oxychloride was removed by evaporation under a reduced pressure. The resulting residual was poured into an ice-water mixture. The resulting mixture was adjusted with a sodium bicarbonate solution to pH≈8, and then extracted with dichlormethane. The organic phase was dried with anhydrous sodium sulfate, concentrated, and purified with a silica-gel column chromatography (petroleum ether:ethyl acetate=3:1) to produce 20.2 g of the title compound as a pale-yellow solid in a yield of 44.5%.

(II) Preparation of the Present Compound

Example 1

Preparation of 2-(6-aminopyridin-3-yl)-10-(3-(trifluoromethyl)phenyl)pyrido[3,2-c][1,5]naphthyridin-9(10H)-one (Compound 1)

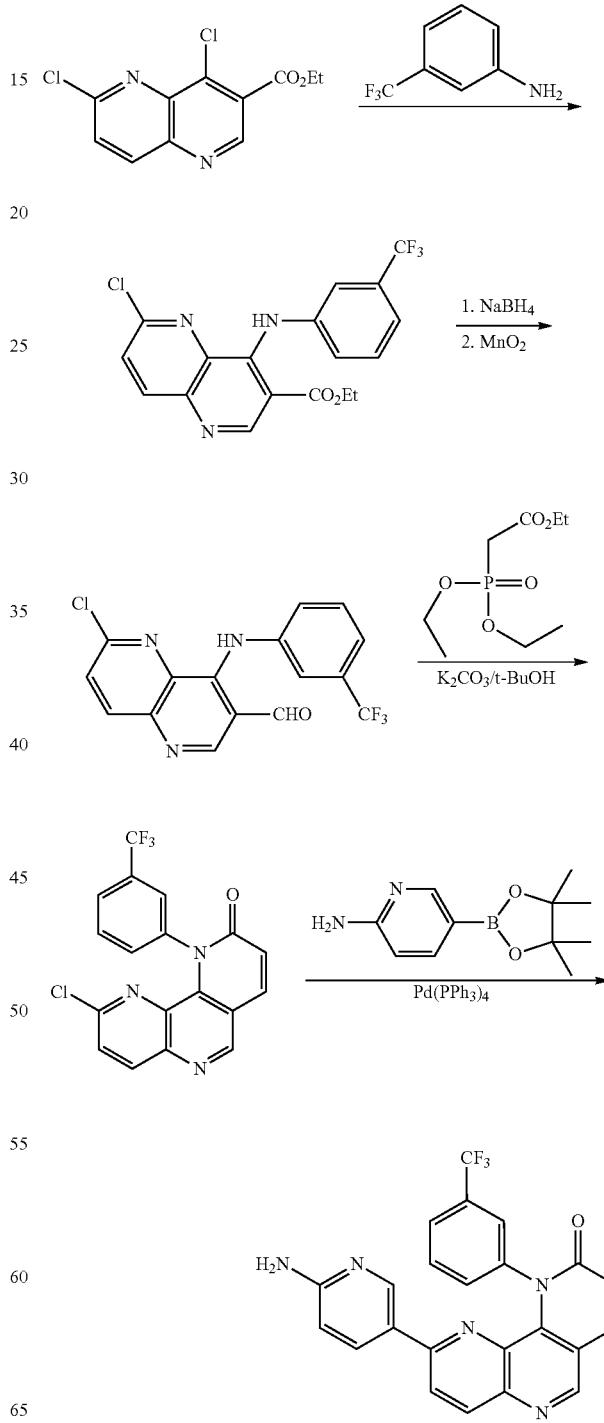

1. Preparation of ethyl 6-chloro-4-(3-(trifluoromethyl)phenylamino)-1,5-naphthyridine-3-carboxylate

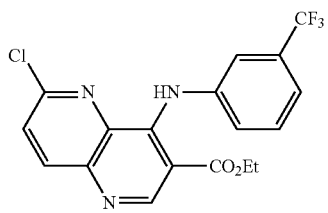 [SMILES: CCOC(=O)c1cnc2ccc(Cl)nc2c1Nc1cccc(C(F)(F)F)c1]

Ethyl 4,6-dichloro-1,5-naphthyridine-3-carboxylate (2.70 g, 10.0 mmol) and 3-trifluoromethylphenylamine (1.77 g, 11.0 mmol) were dissolved in t-butanol (50 mL). To the resulting reaction system was added potassium carbonate (4.15 g, 30.0 mmol). The reaction was conducted with stirring under reflux for 3 hrs. TLC (ethyl acetate:petroleum ether=1:3) showed the starting material disappearance. The reaction system was filtered by suction. The filter cake was washed with dichlormethane. The filter cake was discarded. The washing liquor and the filtrate were combined. The combined material was concentrated under a reduced pressure to obtain a solid, which was recrystallized with diether ether to produce 3.7 g of the title compound as a pale-yellow solid in a yield of 93.5%.

2. Preparation of 6-chloro-4-(3-(tri fluoromethyl)phenylamino)-1,5-naphthyridine-3-carbaldehyde

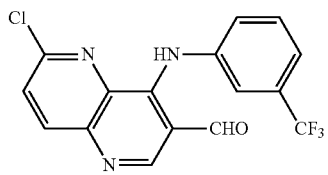 [SMILES: O=Cc1cnc2ccc(Cl)nc2c1Nc1cccc(C(F)(F)F)c1]

ethyl 6-chloro-4-(3-trifluoromethylphenylamino)-1,5-naphthyridin-3-carboxylate (2.5 g, 6.3 mmol) was added to ethanol (80 mL). To this system was added sodium borohydride (0.95 g, 25.1 mmol) in batch. The mixture was stirred at room temperature for 24 hrs. Ethanol was removed by evaporation under a reduced pressure. 20 mL water was added to the resulting residue. The resulting mixture was extracted with dichlormethane. The organic phase was dried with anhydrous sodium sulfate and concentrated in a reduced pressure to produce 1.3 g of the crude product. The crude product was dissolved in dichlormethane (20 mL). To the resulting solution was added manganese dioxide (9.6 g, 110.5 mmol) in batch. The mixture was reacted under stirring at room temperature for 8 h and filtered. The filter cake was washed with dichlormethane. The filter cake was discarded. The washing liquor and the filtrate were combined. The combined material was concentrated under a reduced pressure to obtain a solid, which was purified with a silica-gel column chromatography (ethyl acetate:petroleum ether=2:1) to produce 1.1 g of the title compound in a yield (two steps) of 49.7%.

3. Preparation of 2-chloro-10-(3-(trifluoromethyl)phenyl)pyrido[3,2-c][1,5]naphthyridin-9(10H)-one

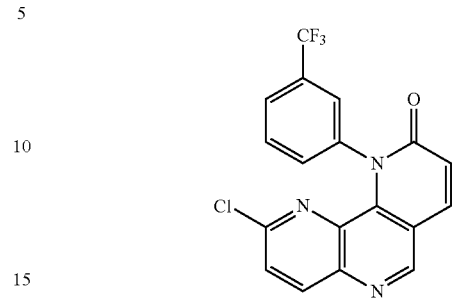

To a solution of 6-chloro-4-(3-(trifluoromethyl)phenylamino)-1,5-naphthyridine-3-carbaldehyde (1.0 g, 2.84 mmol) and ethyl 2-(diethoxyphosphoryl)acetate (1.78 g, 7.98 mmol) in t-butanol (70 mL) in a 250 mL sealed bottle was added potassium carbonate (2.36 g, 17.1 mmol). The mixture was reacted at 160° C. for 36 h. The reaction mixture was cooled. The reaction system was filtered by suction. The filter cake was washed with dichlormethane. The filter cake was discarded. The washing liquor and the filtrate were combined. The combined material was concentrated under a reduced pressure to obtain a solid, which was purified with a silica-gel column chromatography (ethyl acetate:petroleum ether=3:1) to produce 0.56 g of the title compound in a yield of 52.5%.

4. Preparation of 2-(6-aminopyridin-3-yl)-10-(3-(trifluoromethyl)phenyl)pyrido[3,2-c][1,5]naphthyridin-9(10H)-one

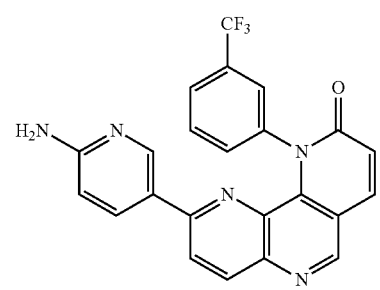

2-chloro-10-(3-(trifluoromethyl)phenyl)pyrido[3,2-c][1,5]naphthyridin-9(10H)-one (418 mg, 1.11 mmol) and 5-(4,4,5,5-tetramethyl-1,3,2-dioxaborolan-2-yl)pyridin-2-amine (368 mg, 1.67 mmol) were dissolved in toluene (40 mL) and ethanol (10 mL). To the resulting reaction system was added palladium tetrakis(triphenylphosphine) (12 mg) and 2 N sodium carbonate solution (2 mL). The resulting mixture was reacted under reflux in a nitrogen-protecting atmosphere for 12 h. The reaction mixture was cooled to the room temperature and the filtered. The organic layer is concentrated in a reduced pressure and then dissolved in dichlormethane. The resulting solution was washed successively by water and saturated brine, dried over anhydrous sodium sulfate, concentrated, and then purified with a silica-gel column chromatography (ethyl acetate:petroleum ether=3:1) to produce 248 mg of the target compound in a yield of 51.5%.

Formula: $C_{23}H_{14}F_3N_5O$ MW: 433.1 MS (M+1): 434

$^1$H NMR ($d_6$-DMSO, 400 MHz): δ 9.14 (1H, s), 8.33 (2H, d), 8.22-8.10 (2H, m), 7.87-7.79 (2H, m), 7.72 (1H, t), 7.65-7.55 (1H, m), 6.95 (1H, d), 6.80 (1H, d), 6.40 (2H, s), 6.27 (1H, d).

According to the preparation method in Example 1 (for compound 1), Compound 3, i.e. (R)-2-(6-aminopyridin-3-yl)-10-(1-(2-hydroxypropanoyl)piperidin-4-yl)pyrido[3,2-c][1,5]naphthyridin-9(10H)-one could be prepared.

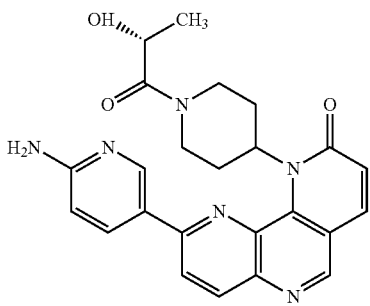 [SMILES: C[C@@H](O)C(=O)N1CCC(n2c(=O)ccc3cnc4ccc(-c5ccc(N)nc5)nc4c32)CC1]

Formula: $C_{24}H_{24}N_6O_3$ MW: 444.19 MS (M+H): 445.

According to the preparation method in Example 1 (for compound 1), Compound 4, i.e., (R)-10-(1-(2-hydroxypropanoyl)piperidin-4-yl)-2-(6-methoxypyridin-3-yl)pyrido[3,2-c][1,5]naphthyridin-9(10H)-one, could be prepared.

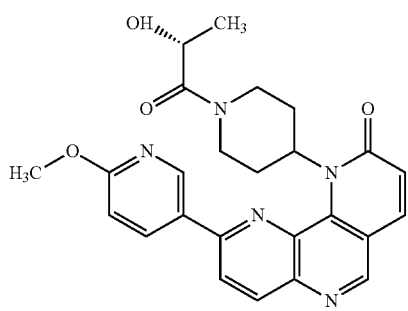 [SMILES: COc1ccc(-c2ccc3ncc4ccc(=O)n(C5CCN(C(=O)[C@@H](C)O)CC5)c4c3n2)cn1]

Formula: $C_{25}H_{25}N_5O_4$ MW: 459.19 MS (M+H): 460.

Example 2

Preparation of 2-(6-methoxypyridin-3-yl)-10-(4-(piperazin-1-yl)-3-(trifluoromethyl)phenyl)pyrido[3,2-c][1,5]naphthyridin-9(10H)-one (Compound 2)

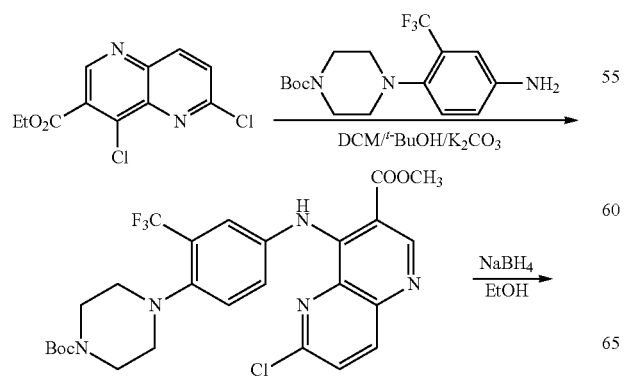

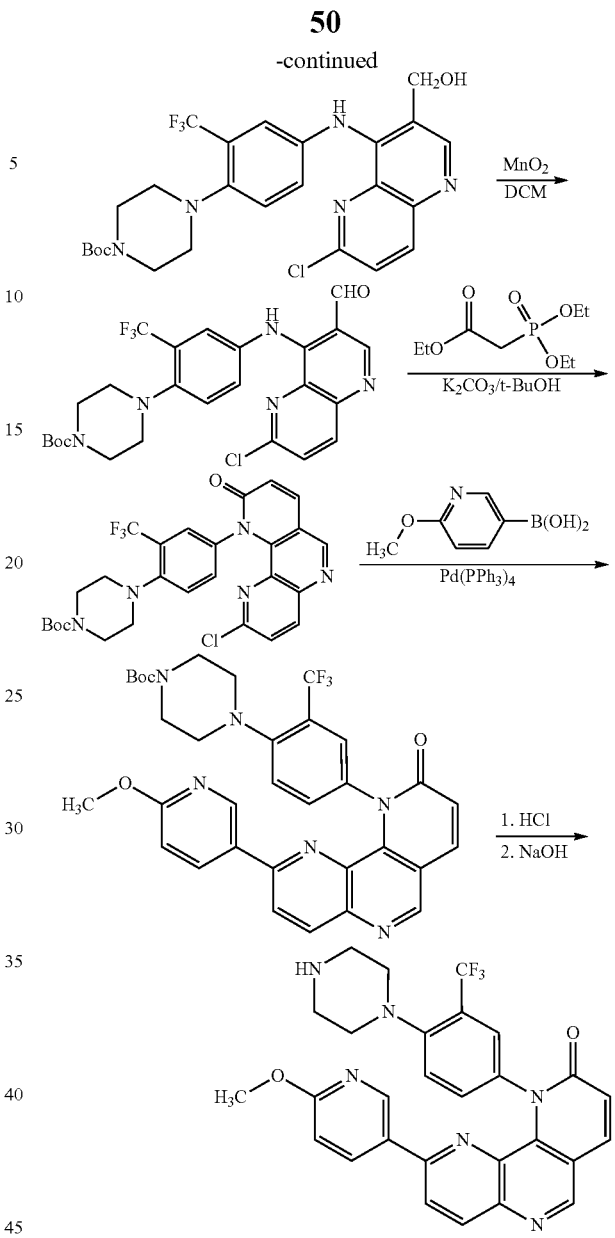

1. Preparation of methyl 4-(4-(4-(tert-butoxycarbonyl)piperazin-1-yl)-3-(trifluoromethyl)phenylamino)-6-chloro-1,5-naphthyridine-3-carboxylate Ethyl 4,6-dichloro-1,5-naphthyridine-3-carboxylate (0.5 g, 1.84 mmol) and tert-butyl 4-(4-amino-2-(trifluoromethyl)phenyl)piperazin-1-carboxylate (0.766 g, 2.22 mmol) were dissolved in a mixed solution of dichlormethane (5 mL) and t-butanol (5 mL). To the resulting reaction system was added potassium carbonate (0.612 g, 4.43 mmol). The mixture was reacted under stirring at room temperature for 24 hrs. The reaction system was filtered by suction. The filter cake was washed with dichlormethane. The filter cake was discarded. The washing liquor and the filtrate were combined. The combined material was concentrated under a reduced pressure to obtain a solid, which was recrystallized with diether ether to produce 0.73 g of the title compound as a pale-yellow solid in a yield of 70.1%.

2. Preparation of tert-butyl 4-(4-(6-chloro-3-(hydroxymethyl)-1,5-naphthyridin-4-ylamino)-2-(trifluoromethyl)phenyl)piperazin-1-carboxylate

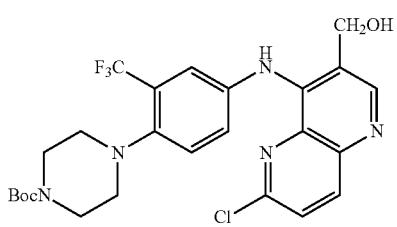 [SMILES: CC(C)(C)OC(=O)N1CCN(c2ccc(Nc3c(CO)cnc4ccc(Cl)nc34)cc2C(F)(F)F)CC1]

methyl 4-(4-(4-(tert-butoxycarbonyl)piperazin-1-yl)-3-(trifluoromethyl)phenylamino)-6-chloro-1,5-naphthyridine-3-carboxylate (0.565 g, 1.0 mmol) was added to ethanol (10 mL). To the system was added sodium borohydride (0.228 g, 6 mmol) in batch. The mixture was stirred at room temperature for 18 hrs. Ethanol was removed under a reduced pressure. To the resulting residual was added to water (10 mL). The resulting mixture was extracted with dichlormethane. The organic phase was dried with anhydrous sodium sulfate and concentrated in a reduced pressure to produce a title compound as solid crude, which was directly used in the next step.

3. Preparation of tert-butyl 4-(4-(6-chloro-3-formyl-1,5-naphthyridin-4-ylamino)-2-(trifluoromethyl)phenyl)piperazin-1-carboxylate

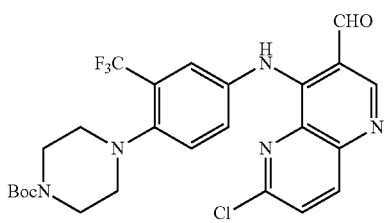 [SMILES: CC(C)(C)OC(=O)N1CCN(c2ccc(Nc3c(C=O)cnc4ccc(Cl)nc34)cc2C(F)(F)F)CC1]

The crude tert-butyl 4-(4-(6-chloro-3-(hydroxymethyl)-1,5-naphthyridin-4-ylamino)-2-(trifluoromethyl)phenyl)piperazin-1-carboxylate (1 mmol) directly obtained in the above step was dissolved in dichlormethane (10 mL). To the resulting solution was added manganese dioxide (2.14 g, 24.6 mmol). The resulting mixture was reacted under stirring at room temperature 3 h and filtered. The filter cake was washed with dichlormethane. The filter cake was discarded. The washing liquor and the filtrate were combined. The combined material was concentrated under a reduced pressure to obtain a solid, which was purified with a silica-gel column chromatography (ethyl acetate:petroleum ether=2:1) to produce 0.33 g of the title compound in a yield (two steps) of 61.6%.

4. Preparation of tert-butyl 4-(4-(2-chloro-9-oxopyrido[3,2-c][1,5]naphthyridin-10(9H)-yl)-2-(trifluoromethyl)phenyl)piperazin-1-carboxylate

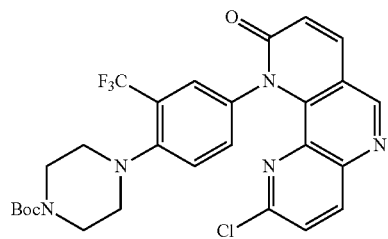 [SMILES: CC(C)(C)OC(=O)N1CCN(c2ccc(-n3c(=O)ccc4cnc5ccc(Cl)nc5c43)cc2C(F)(F)F)CC1]

To a solution of tert-butyl 4-(4-(6-chloro-3-formyl-1,5-naphthyridin-4-ylamino)-2-(trifluoromethyl)phenyl)piperazin-1-carboxylate (2.5 g, 4.66 mmol) and ethyl 2-(diethoxyphosphoryl)acetate (2.93 g, 13.1 mmol) in t-butanol (125 mL) in 250 mL seal bottom was added potassium carbonate (3.87 g, 28.0 mmol). The mixture was reacted at 160° C. for 36 h. The reaction mixture was cooled. The reaction system was filtered by suction. The filter cake was washed with dichlormethane. The filter cake was discarded. The washing liquor and the filtrate were combined. The combined material was concentrated under a reduced pressure to obtain a solid, which was purified with a silica-gel column chromatography (ethyl acetate:petroleum ether=3:1) to produce 145 mg of the target compound in a yield of 5.6%.

5. Preparation of tert-butyl 4-(4-(2-(6-methoxypyridin-3-yl)-9-oxopyrido[3,2-c][1,5]naphthyridin-10(9H)-yl)-2-(trifluoromethyl)phenyl)piperazin-1-carboxylate

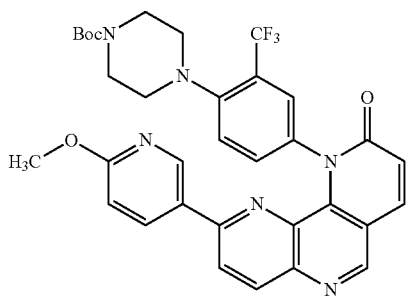 [SMILES: COc1ccc(-c2ccc3ncc4ccc(=O)n(-c5ccc(N6CCN(C(=O)OC(C)(C)C)CC6)c(C(F)(F)F)c5)c4c3n2)cn1]

tert-butyl 4-(4-(2-(6-methoxypyridin-3-yl)-9-oxopyrido[3,2-c][1,5]naphthyridin-10(9H)-yl)-2-(trifluoromethyl)phenyl)piperazin-1-carboxylate (145 mg, 0.26 mmol) and 6-methoxy-3-pyridine boric acid (40 m g, 0.26 mmol) were dissolved in toluene (8 mL) and ethanol (2 mL). To the resulting reaction system was added palladium tetrakis(triphenylphosphine) (3 mg) and 2N sodium carbonate solution (0.12 mL). The resulting mixture was reacted under reflux in a nitrogen-protecting atmosphere for 4 h. The reaction mixture was cooled to room temperature, and filtered. The organic layer was separated out, concentrated in a reduced pressure, dissolved in dichlormethane, successively washed with water and saturated brine, dried over anhydrous sodium sulfate, concentrated, purified with a silica-gel column chromatography (ethyl acetate:petroleum ether=3:1) to produce 72 mg of the target compound in a yield of 43.8%.

6. Preparation of 2-(6-methoxypyridin-3-yl)-10-(4-(piperazin-1-yl)-3-(trifluoromethyl)phenyl)pyrido[3,2-c][1,5]naphthyridin-9(10H)-one

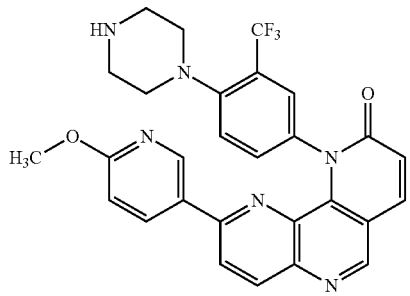 [SMILES: COc1ccc(-c2ccc3ncc4ccc(=O)n(-c5ccc(N6CCNCC6)c(C(F)(F)F)c5)c4c3n2)cn1]

tert-butyl 4-(4-(2-(6-methoxypyridin-3-yl)-9-oxopyrido[3,2-c][1,5]naphthyridin-10(9H)-yl)-2-(trifluoromethyl)phenyl)piperazin-1-carboxylate (72 mg, 0.114 mmol) was dissolved in dichlormethane (8 mL). To this system was introduced a gas of hydrogen chloride for 0.5 h. The solid was separated out and filtered by suction. The resulting solid was successively washed with dichlormethane and diethylether. The resulting solid was dissolved in water. The resulting solution was adjusted with 1N sodium hydroxide solution to pH≈9, and then extracted with ethyl acetate. The organic phase was washed with saturated brine, dried over anhydrous sodium sulfate, concentrated in a reduced pressure to produce 54 g of the title compound as a solid in a yield of 88.6%.

Formula: $C_{28}H_{23}F_3N_6O_2$ MW: 532.18 MS (M+H): 532.9
$^1$H NMR (CDCl$_3$, 400 MHz): δ 9.04 (1H, s), 8.43 (1H, d), 8.14 (1H, d), 8.03 (11-1, d), 7.95 (1H, d), 7.59 (1H, d), 7.47-7.38 (3H, m), 7.01 (1H, d), 6.72 (1H, d), 3.97 (3H, s), 3.05 (6H, br s), 2.98-2.89 (2H, m).

Example 3

Preparation of 2-methyl-2-(4-(9-oxo-2-(quinolin-3-yl)pyrido[3,2-c][1,5]naphthyridin-10(9H)-yl)phenyl)propanenitrile (Compound 5)

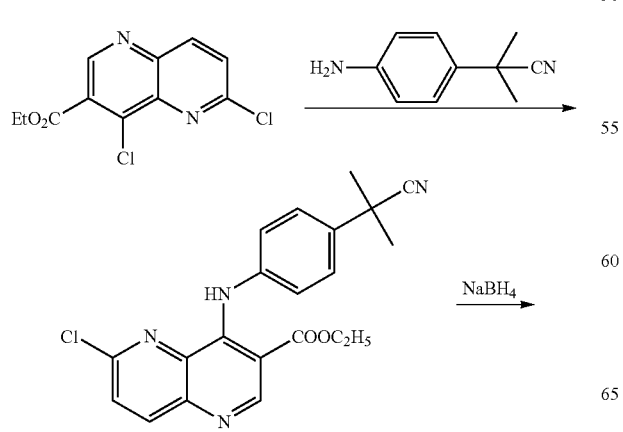

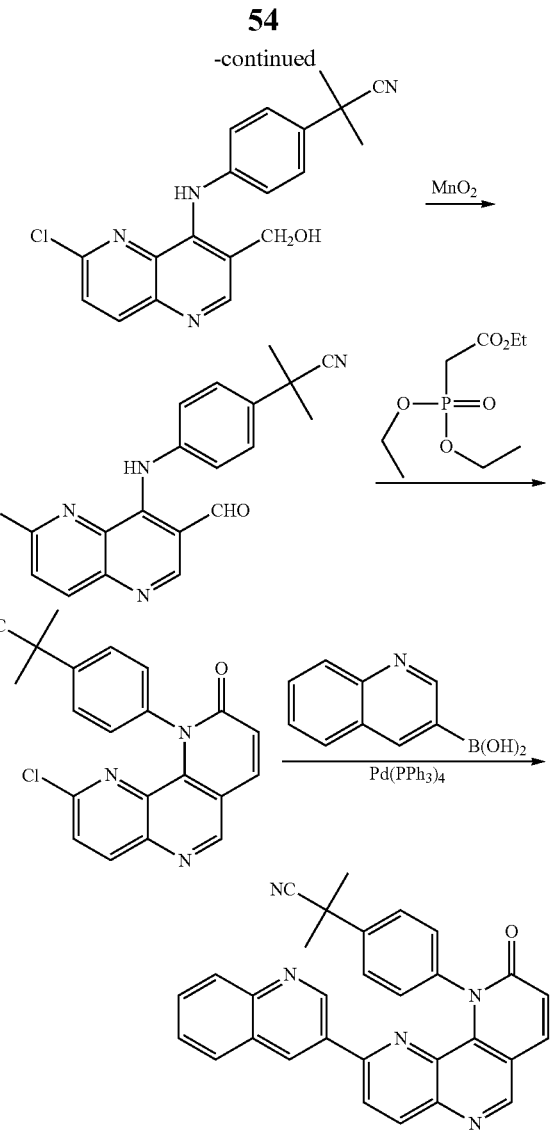

1. Preparation of methyl 6-chloro-4-(4-(2-(cyanopropan-2-yl)phenylamino)-1,5-naphthyridine-3-carboxylate Ethyl 4,6-dichloro-1,5-naphthyridine-3-carboxylate (5.0 g, 18.4 mmol) and 2-(4-aminophenyl)-2-methylpropanenitrile (2.96 g, 18.5 mmol) were dissolved in 1,4-dioxane (80 mL). The reaction was conducted with stirring under reflux for 4 hrs. The reaction mixture was cooled, and concentrated in a reduced pressure. The resulting solid was dissolved with dichlormethane, successively washed with saturated aqueous sodium carbonate solution and saturated brine, dried over anhydrous sodium sulfate, and concentrated in a reduced pressure to produce 6.54 g of the title compound as a pale-yellow solid in a yield of 90.2%.

2. Preparation of 2-(4-(6-chloro-3-(hydroxymethyl)-1,5-naphthyridin-4-ylamino)phenyl)-2-methy 1 propanenitrile

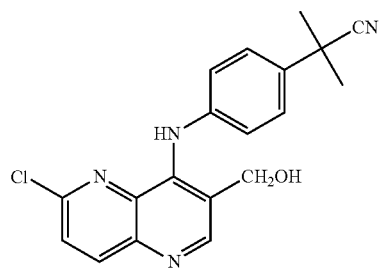 [SMILES: CC(C)(C#N)c1ccc(Nc2c(CO)cnc3ccc(Cl)nc23)cc1]

6-chloro-4-(4-(2-(cyanopropan-2-yl)phenylamino)-1,5-naphthyridine-3-ethyl carboxylate (6.54 g, 16.6 mmol) was added to ethanol (200 mL). To the system was added sodium borohydride (6.27 g, 166 mmol) in batch. The mixture was stirred at room temperature for 24 hrs. Ethanol was removed under a reduced pressure. The resulting solution was adjusted with 1N diluted hydrochloric acid to a neutral pH, and extracted with ethyl acetate. The organic phase was dried with anhydrous sodium sulfate, concentrated in a reduced pressure to produce 5.8 g of the title compound as solid crude, which was directly used in the next step.

3. Preparation of 2-(4-(6-chloro-3-formyl-1,5-naphthyridin-4-ylamino)phenyl)-2-methylpropanenitrile

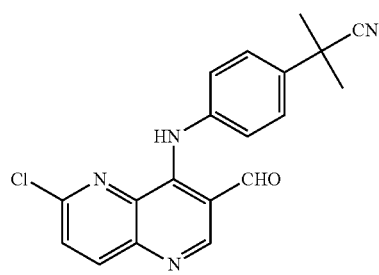 [SMILES: CC(C)(C#N)c1ccc(Nc2c(C=O)cnc3ccc(Cl)nc23)cc1]

About 5.8 g of crude 2-(4-(6-chloro-3-(hydroxymethyl)-1,5-naphthyridin-4-ylamino)phenyl)-2-methyl propanenitrile obtained in the above step was dissolved in dichlormethane (80 mL). To the resulting solution added manganese dioxide (46.2 g, 0.53 mol) in batch. The resulting mixture was reacted under stirring at room temperature for 30 hrs and then filtered. The filter cake was washed with dichlormethane. The filter cake was discarded. The washing liquor and the filtrate were combined. The combined material was concentrated under a reduced pressure to obtain a solid. The resulting solid was purified with a silica-gel column chromatography (ethyl acetate:petroleum ether=2:1) to produce 2.3 g of the title compound in a yield (two steps) of 39.5%.

4. Preparation of 2-(4-(2-chloro-9-oxopyrido[3,2-c][1,5]naphthyridin-10(9H)-yl)phenyl)-2-methyl propanenitrile

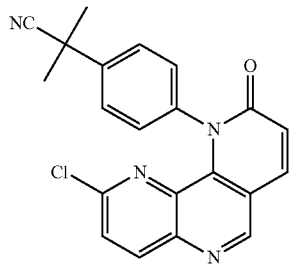 [SMILES: CC(C)(C#N)c1ccc(-n2c(=O)ccc3cnc4ccc(Cl)nc4c32)cc1]

To a 250 mL sealed bottle were successively added 2-(4-(6-chloro-3-formyl-1,5-naphthyridin-4-ylamino)phenyl)-2-methylpropanenitrile (1.0 g, 2.85 mmol), ethyl 2-(diethoxyphosphoryl)acetate (1.8 g, 8.03 mmol), t-butanol (70 mL) and potassium carbonate (1.85 g, 13.4 mmol). The resulting mixture was reacted at 160° C. for 48 hrs. The reaction mixture was cooled. The reaction system was filtered by suction. The filter cake was washed with dichlormethane. The filter cake was discarded. The washing liquor and the filtrate were combined. The combined material was concentrated under a reduced pressure to obtain a solid. The resulting solid was purified with a silica-gel column chromatography (ethyl acetate:petroleum ether=1:1) to produce 0.31 g of the title compound in a yield of 29.0%.

5. Preparation of 2-methyl-2-(4-(9-oxo-2-(quinolin-3-yl)pyrido[3,2-c][1,5]naphthyridin-10(9H)-yl)phenyl)propanenitrile

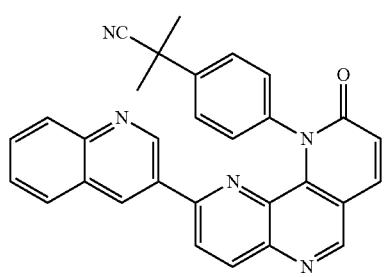 [SMILES: CC(C)(C#N)c1ccc(-n2c(=O)ccc3cnc4ccc(-c5cnc6ccccc6c5)nc4c32)cc1]

2-(4-(2-chloro-9-oxopyrido[3,2-c][1,5]naphthyridin-10 (9H)-yl)phenyl)-2-methyl propanenitrile (310 mg, 0.827 mmol) and quinolin-3-yl boric acid (159 mg, 0.919 mmol) were dissolved in toluene (21 mL) and ethanol (7 mL). To the resulting reaction system was added palladium tetrakis (triphenylphosphine) (10 mg) and 2N sodium carbonate solution (1.2 mL). The resulting mixture was reacted under reflux in a nitrogen-protecting atmosphere for 8 hrs. The reaction mixture was cooled to room temperature, and filtered. The organic layer was separated out, concentrated in a reduced pressure, dissolved in dichlormethane, successively washed with water and saturated brine, dried over anhydrous sodium sulfate, concentrated, and purified with a silica-gel column chromatography (ethyl acetate:petroleum ether=1:1) to produce 108 mg of the target compound in a yield of 27.9%.

Formula: $C_{30}H_{21}N_5O$ MW: 467.17 MS (M+H): 467.9

$^1$H-NMR (d$_6$-DMSO, 400 MHz): δ 9.25 (1H, s), 8.76 (1H, d), 8.55 (1H, d), 8.46 (1H, d), 8.41-8.33 (2H, m), 8.04 (1H, d), 7.99 (1H, d), 7.85-7.77 (1H, m), 7.69-7.58 (3H, m), 7.43 (2H, d), 6.99 (1H, d), 1.60 (6H, s).

Example 4

Preparation of 2-(6-aminopyridin-3-yl)-10-(4-(piperazin-1-yl)-3-(trifluoromethyl)phenyl)pyrido[3,2-c][1,5]naphthyridin-9(10H)-one (Compound 6)hydrochloride

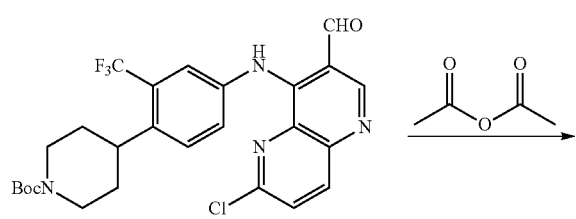

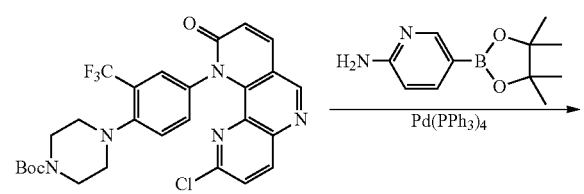

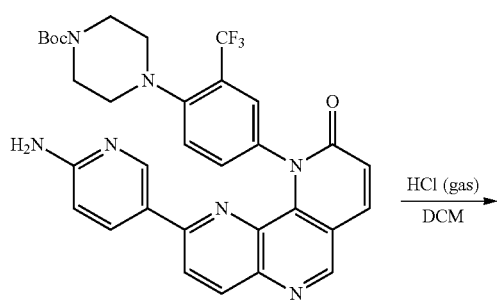

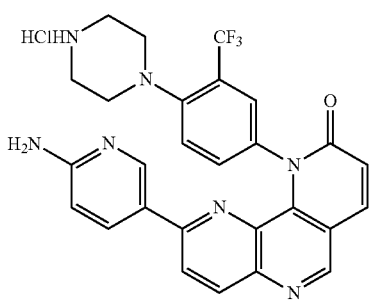

1. Preparation of tert-butyl 4-(4-(2-chloro-9-oxopyrido[3,2-c][1,5]naphthyridin-10(9H)-yl)-2-(trifluoromethyl)phenyl)piperazin-1-carboxylate

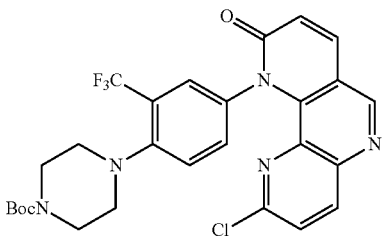 [SMILES: CC(C)(C)OC(=O)N1CCN(c2ccc(-n3c(=O)ccc4cnc5ccc(Cl)nc5c43)cc2C(F)(F)F)CC1]

tert-butyl 4-(4-(6-chloro-3-formyl-1,5-naphthyridin-4-ylamino)-2-(trifluoromethyl)phenyl) piperazin-1-carboxylate (524 mg, 0.98 mmol) was dissolved in 9 mL N,N-dimethylacetamide and 6 mL acetic anhydride. The resulting mixture was reacted in a microwave reactor at 160° C. for 40 min. The reaction mixture was cooled. A large portion of the solvent was removed under a reduced pressure. The resulting residue was purified with a silica-gel column chromatography (ethyl acetate) to produce 505 mg of the title compound as a white solid in a yield of 91.8%.

2. Preparation of tert-butyl 4-(4-(2-(6-aminopyridin-3-yl)-9-oxopyrido[3,2-c][1,5]naphthyridin-10(9H)-yl)-2-(trifluoromethyl)phenyl)piperazin-1-carboxylate

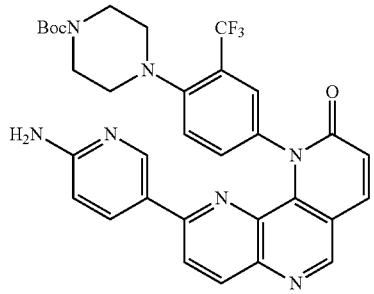 [SMILES: CC(C)(C)OC(=O)N1CCN(c2ccc(-n3c(=O)ccc4cnc5ccc(-c6ccc(N)nc6)nc5c43)cc2C(F)(F)F)CC1]

tert-butyl 4-(4-(2-(6-methoxypyridin-3-yl)-9-oxopyrido[3,2-c][1,5]naphthyridin-10(9H)-yl)-2-(trifluoromethyl)phenyl)piperazin-1-carboxylate (302 mg, 0.54 mmol) and 5-(4,4,5,5-tetramethyl-1,3,2-dioxaborolan-2-yl)pyridin-2-amine (240 mg, 1.09 mmol) were dissolved in toluene (6 mL) and ethanol (2 mL). To the resulting reaction system was added palladium tetrakis(triphenylphosphine) (13 mg) and 2N sodium carbonate solution (1.6 mL). The resulting mixture was reacted under reflux in a nitrogen-protecting atmosphere for 4 h. The reaction mixture was cooled to room temperature and filtered. The organic layer was separated out, concentrated in a reduced pressure, dissolved in dichloromethane, successively washed with water and saturated brine, dried over anhydrous sodium sulfate, concentrated, and purified with a silica-gel column chromatography (ethyl acetate:petroleum ether=1:1) to produce 312 mg of the target compound in a yield of 93.5%.

3. Preparation of 2-(6-aminopyridin-3-yl)-10-(4-(piperazin-1-yl)-3-(trifluoromethyl)phenyl)pyrido[3,2-c][1,5]naphthyridin-9(10H)-one hydrochloride

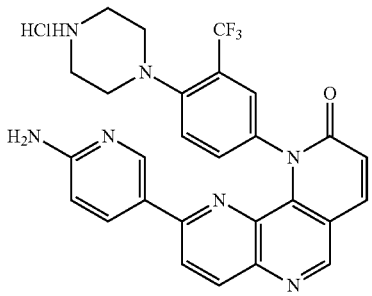

tert-butyl 4-(4-(2-(6-aminopyridin-3-yl)-9-oxopyrido[3,2-c][1,5]naphthyridin-10(9H)-yl)-2-(trifluoromethyl)phenyl)piperazin-1-carboxylate (312 mg, 0.505 mmol) was dissolved in dichlormethane (8 mL). To this system was introduced a gas of hydrogen chloride for 0.5 h. The solid was separated out and filtered by suction. The resulting solid was successively washed with dichlormethane and diethylether to produce 271 mg of the title compound as a white solid in a yield of 96.8%.

Formula: $C_{27}H_{23}ClF_3N_7O$ MW: 553.16 MS (M−HCl+H): 518.0

$^1$H-NMR (D$_2$O, 400 MHz): δ 9.06 (1H, s), 8.28-8.19 (2H, m), 8.04 (1H, s), 7.88 (1H, d), 7.51 (1H, s), 7.38 (1H, d), 7.22 (1H, d), 7.05-6.93 (2H, m), 6.74 (1H, d), 3.32 (4H, br s), 3.22-3.10 (2H, m), 2.88-2.78 (2H, m).

Example 5

Preparation of 2-(4-(2-(6-aminopyridin-3-yl)-9-oxopyrido[3,2-c][1,5]naphthyridin-10(9H)-yl)phenyl)-2-methylpropanenitrile (Compound 7)

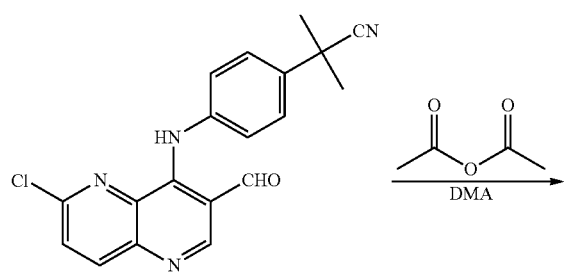

1. Preparation of 2-(4-(2-chloro-9-oxopyrido[3,2-c][1,5]naphthyridin-10(9H)-yl)phenyl)-2-methyl propanenitrile

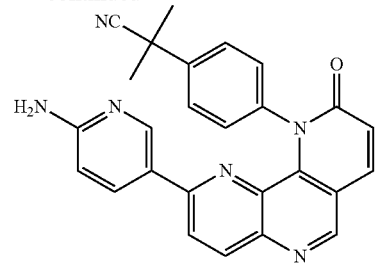 [SMILES: CC(C)(C#N)c1ccc(-n2c(=O)ccc3cnc4ccc(-c5ccc(N)nc5)nc4c32)cc1]

2-(4-(6-chloro-3-formyl-1,5-naphthyridin-4-ylamino)phenyl)-2-methylpropanenitrile (1.3 g, 3.71 mmol) was dissolved in 12 mL N,N-dimethylacetamide and 8 mL acetic anhydride. The resulting mixture was reacted in a microwave reactor at 160° C. for 60 mins. The reaction mixture was cooled. A large portion of the solvent was removed under a reduced pressure. The resulting residue was purified with a silica-gel column chromatography (ethyl acetate) to produce 1.1 g of the title compound as a white solid in a yield of 79.0%.

2. 2-(4-(2-(6-aminopyridin-3-yl)-9-oxopyrido[3,2-c][1,5]naphthyridin-10(9H)-yl)phenyl)-2-methylpropanenitrile

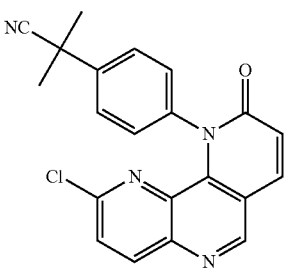

2-(4-(2-chloro-9-oxopyrido[3,2-c][1,5]naphthyridin-10(9H)-yl)phenyl)-2-methyl propanenitrile (400 mg, 1.07 mmol) and 5-(4,4,5,5-tetramethyl-1,3,2-dioxaborolan-2-yl)pyridin-2-amine (282 mg, 1.28 mmol) were dissolved in toluene (21 mL) and ethanol (7 mL). To the resulting reaction system was added palladium tetrakis(triphenylphosphine) (12 mg) and 2N sodium carbonate solution (1.6 mL). The resulting mixture was reacted under reflux in a nitrogen-protecting atmosphere for 8 hrs. The reaction mixture was cooled to room temperature and filtered. The organic layer was separated out, concentrated in a reduced pressure, dissolved in dichlormethane, successively washed with water and saturated brine, dried over anhydrous sodium sulfate, concentrated, and purified with a silica-gel column chromatography (ethyl acetate:petroleum ether=1:1) to produce 61 mg of the target compound in a yield of 13.2%.

Formula: $C_{26}H_{20}N_6O$ MW: 432.17 MS (M+H): 433.0

$^1$H-NMR (d$_6$-DMSO, 400 MHz): δ 9.11 (1H, s), 8.35-8.26 (2H, m), 8.10 (1H, d), 7.96 (1H, s), 7.60 (2H, d), 7.34 (2H, d), 7.24 (1H, d), 6.92 (1H, d), 6.39-6.27 (3H, m), 1.74 (6H, s).

Example 6

Preparation of 2-(4-(2-(6-methoxypyridin-3-yl)-9-oxopyrido[3,2-c][1,5]naphthyridin-10(9H)-yl)phenyl)-2-methylpropanenitrile (Compound 12)

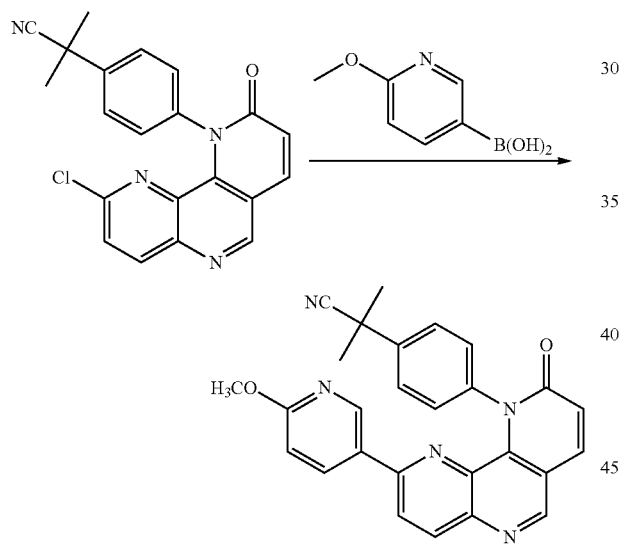

The specific procedure was the same as those in Example 1, except for substituting 2-(4-(2-chloro-9-oxopyrido[3,2-c][1,5]naphthyridin-10(9H)-yl)phenyl)-2-methyl propanenitrile (200 mg, 0.534 mmol) and 6-methoxy-3-pyridine boric acid (100 mg, 0.654 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 182 mg of the target compound in a yield of 76.2%.

Formula: $C_{27}H_{21}N_5O_2$ MW: 447.17 MS (M+H): 448.2

$^1$H-NMR (d$_6$-DMSO, 400 MHz): δ 9.18 (1H, s), 8.42 (1H, d) 8.33 (1H, d), 8.21 (1H, d) 7.85 (1H, d), 7.79 (1H, dd), 7.63 (2H, d), 7.37 (2H, d), 6.95 (1H, d), 6.78 (1H, d), 3.91 (3H, s), 1.75 (6H, s).

Example 7

Preparation of 2-(2-aminopyrimidin-5-yl)-10-(3-(trifluoromethyl)phenyl)pyrido[3,2-c][1,5]naphthyridin-9(10H)-one (Compound 13)

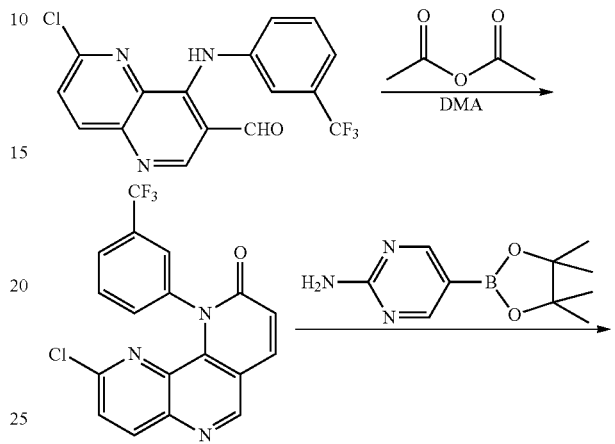

1. Preparation of 2-chloro-10-(3-(trifluoromethyl) phenyl)pyrido[3,2-c][1,5]naphthyridine-9(10H)-one

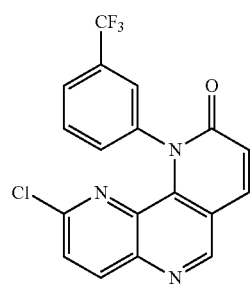 [SMILES: O=c1ccc2cnc3ccc(Cl)nc3c2n1-c1cccc(C(F)(F)F)c1]

6-chloro-4-(3-(trifluoromethyl)phenylamino)-1,5-naphthyridine-3-carbaldehyde (0.600 g, 1.71 mmol) was dissolved in 10 mL N,N-dimethylacetamide and 6 mL acetic anhydride. The resulting mixture was reacted in a microwave reactor at 160° C. for 40 min. The reaction mixture was cooled. A large portion of the solvent was removed under a reduced pressure. The resulting residue was purified with a silica-gel column chromatography (ethyl acetate) to produce 0.580 g of the title compound as a white solid in a yield of 90.1%.

2. Preparation of 2-(2-aminopyrimidin-5-yl)-10-(3-(trifluoromethyl)phenyl)pyrido[3,2-c][1,5]naphthyridin-9(10H)-one

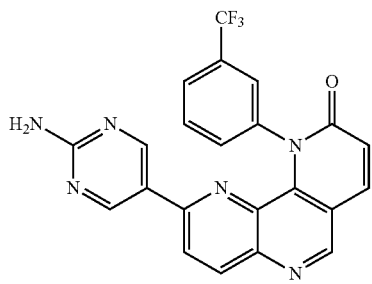 [SMILES: Nc1ncc(-c2ccc3ncc4ccc(=O)n(-c5cccc(C(F)(F)F)c5)c4c3n2)cn1]

The specific procedure was the same as those in Example 1, Step 4, except for substituting 2-chloro-10-(3-(trifluoromethyl)phenyl)pyrido[3,2-c][1,5]naphthyridin-9(10H)-one (300 mg, 0.799 mmol) and 5-(4,4,5,5-tetramethyl-1,3,2-dioxaborolan-2-yl)pyrimidin-2-amine (213 mg, 0.963 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 148 mg of the target compound in a yield of 42.7%.

Formula: $C_{22}H_{13}F_3N_6O$ MW: 434.11 MS (M+H): 434.9
$^1$H-NMR (d$_6$-DMSO, 400 MHz): δ 9.14 (1H, s), 8.41-8.29 (2H, m), 8.15 (1H, d), 7.98 (2H, s), 7.82-7.70 (3H, m), 7.69-7.63 (1H, m), 7.03 (2H, s), 6.94 (1H, d).

Example 8

Preparation of 2-(2-methoxypyrimidin-5-yl)-10-(3-(trifluoromethyl)phenyl)pyrido[3,2-c][1,5]naphthyridin-9(10H)-one (Compound 14)

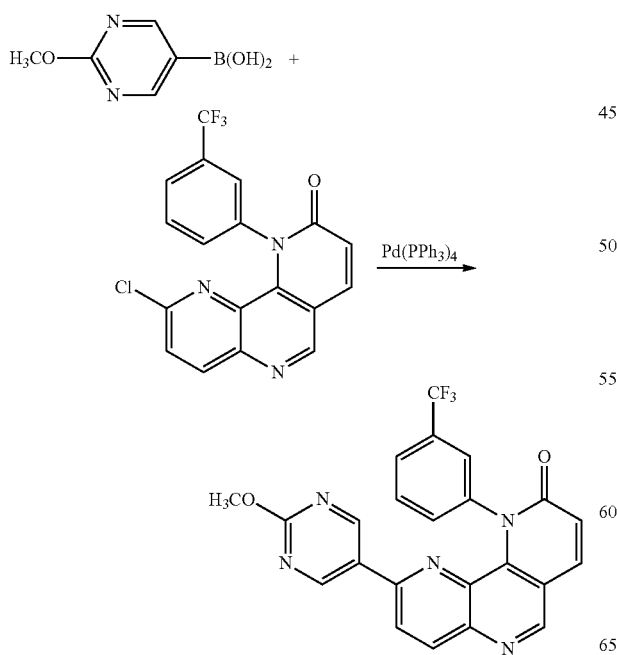

The specific processure was the same as those in Example 1, Step 4, except for substituting 2-chloro-10-(3-(trifluoromethyl)phenyl)pyrido[3,2-c][1,5]naphthyridin-9(10H)-one (180 mg, 0.479 mmol) and 2-methoxypyrimidin-5-yl boric acid (89 mg, 0.578 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 165 mg of the target compound in a yield of 76.6%.

Formula: $C_{23}H_{14}F_3N_5O_2$ MW: 449.11 MS (M+H): 450.2
$^1$H-NMR (d$_6$-DMSO, 400 MHz): δ 9.25 (1H, s), 8.50 (1H, d), 8.37 (1H, d), 8.33 (2H, s), 8.30 (1H, d), 7.85 (1H, s), 7.82 (1H, d), 7.74 (1H, t), 7.66 (1H, d), 7.00 (1H, d), 3.96 (3H, s).

Example 9

Preparation of N-(5-(9-oxo-10-(3-(trifluoromethyl)phenyl)-9,10-dihydropyrido[3,2-c][1,5]naphthyridin-2-yl)pyridin-2-yl)acetamide (Compound 15)

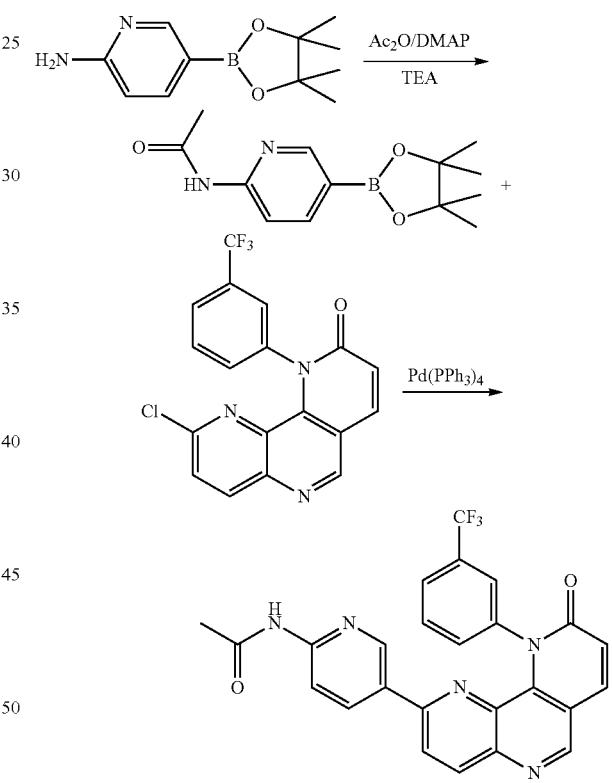

1. Preparation of N-(5-(4,4,5,5-tetramethyl-1,3,2-dioxaborolan-2-yl)pyridin-2-yl)acetamide

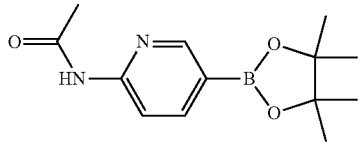 [SMILES: CC(=O)Nc1ccc(B2OC(C)(C)C(C)(C)O2)cn1]

To a solution of 5-(4,4,5,5-tetramethyl-1,3,2-dioxaborolan-2-yl)pyridin-2-amine (300 mg, 1.36 mmol) in dichlormethane (15 mL) were successively added dimethylaminopyridine (17 mg, 0.139 mmol), triethylamine (0.21 mL, 1.50 mmol) and acetic anhydride (153 mg, 1.50 mmol). The resulting mixture was reacted under stirring at room temperature for several hours. Then the reaction mixture was diluted with dichlormethane, and washed with aqueous saturated ammonium chloride solution. The organic phase was dried with anhydrous magnesium sulfate, filtered, concentrated to produce 225 mg of the target compound in a yield of 63.1%.

2. Preparation of N-(5-(9-oxo-10-(3-(trifluoromethyl)phenyl)-9,10-dihydropyrido[3,2-c][1,5]naphthyridin-2-yl)pyridin-2-yl)acetamide

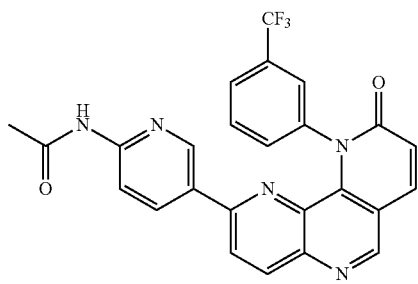 [SMILES: CC(=O)Nc1ccc(-c2ccc3ncc4ccc(=O)n(-c5cccc(C(F)(F)F)c5)c4c3n2)cn1]

To N-(5-(4,4,5,5-tetramethyl-1,3,2-dioxaborolan-2-yl)pyridin-2-yl)acetamide (225 m g, 0.858 mmol) were added 2-chloro-10-(3-(trifluoromethyl)phenyl)pyrido[3,2-c][1,5]naphthyridin-9(10H)-one (300 mg, 0.799 mmol), palladium tetrakis(triphenylphosphine)(15 mg) and 2N sodium carbonate solution (1.3 mL). This system was reacted in a nitrogen-protecting atmosphere at 90° C. for 16 hrs. The reaction mixture was cooled to room temperature and filtered. The organic layer was separated out, concentrated in a reduced pressure, dissolved in dichlormethane, successively washed with water and saturated brine, dried over anhydrous sodium sulfate, concentrated and purified with a silica-gel column chromatography (ethyl acetate) to produce 160 mg of the target compound in a yield of 42.2%.

Formula: $C_{25}H_6F_3N_5O_2$ MW: 475.13 MS (M+H): 476.2

$^1$H-NMR (d$_6$-DMSO, 400 MHz): δ 10.65 (1H, s), 9.23 (1H, s), 8.46 (1H, d), 8.37 (1H, d), 8.34 (1H, d), 8.32 (1H, d), 7.98 (1H, d), 7.86 (1H, s), 7.80 (1H, d), 7.74 (1H, t), 7.66 (1H, d), 7.31 (1H, dd), 6.98 (1H, d), 2.12 (3H, s).

Example 10

Preparation of 5-(9-oxo-10-(3-(trifluoromethyl)phenyl)-9,10-dihydropyrido[3,2-c][1,5]naphthyridin-2-yl)-2-cyanopyridine (Compound 16)

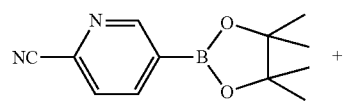

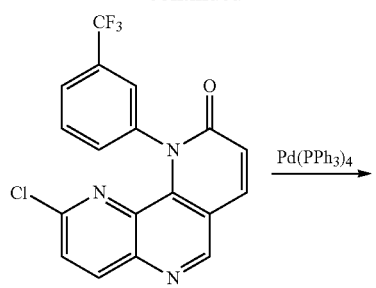

-continued

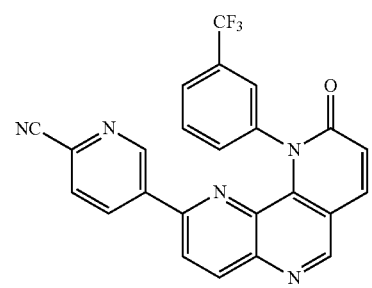

The specific processure was the same as those in Example 9 (for the preparation of compound 15), Step 2, except for substituting 2-chloro-10-(3-(trifluoromethyl)phenyl)pyrido[3,2-c][1,5]naphthyridin-9(10H)-one (188 mg, 0.50 mmol) and 5-(4,4,5,5-tetramethyl-1,3,2-dioxaborolan-2-yl)-2-cyanopyridine (138 mg, 0.60 mmol) respectively for 2-chloro-10-(3-(trifluoromethyl)phenyl)pyrido[3,2-c][1,5]naphthyridin-9(10H)-one and N-(5-(4,4,5,5-tetramethyl-1,3,2-dioxaborolan-2-yl)pyridin-2-yl)acetamide to produce 128 mg of the target compound in a yield of 57.8%.

Formula: $C_{24}H_{12}F_3N_5O$ MW: 443.1 MS (M+H): 444.1

$^1$H-NMR (d$_6$-DMSO, 400 MHz): δ 9.27 (1H, s), 8.55 (1H, d), 8.49 (1H, d), 8.40 (1H, d), 8.37 (1H, d), 7.97 (1H, d), 7.89 (1H, d), 7.81 (1H, s), 7.77 (1H, t), 7.71-7.62 (2H, m), 7.00 (1H, d).

Example 11

Preparation of 2-(1H-pyrrolo[2,3-b]pyridin-3-yl)-10-(3-(trifluoromethyl)phenyl)pyrido[3,2-c][1,5]naphthyridin-9(10H)-one (Compound 17)

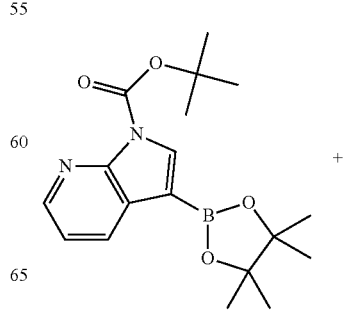

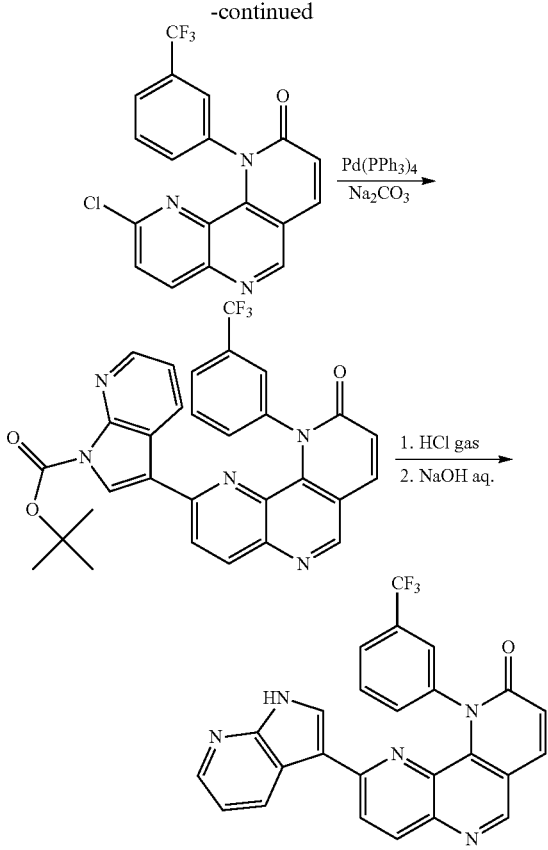

1. Preparation of tert-butyl 3-(9-oxo-10-(3-(trifluoromethyl)phenyl)-9,10-dihydropyrido[3,2-c][1,5]naphthyridin-2-yl)-1H-pyrrolo[2,3-b]pyridin-1-carboxylate

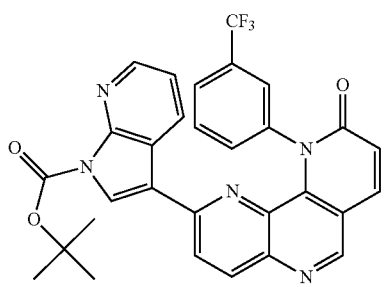 [SMILES: CC(C)(C)OC(=O)n1cc(-c2ccc3ncc4ccc(=O)n(-c5cccc(C(F)(F)F)c5)c4c3n2)c2cccnc21]

2-chloro-10-(3-(trifluoromethyl)phenyl)pyrido[3,2-c][1,5]naphthyridin-9(10H)-one (137 mg, 0.365 mmol) and tert-butyl 3-(4,4,5,5-tetramethyl-1,3,2-dioxaborolan-2-yl)-1H-pyrrolo[2,3-b]pyridin-1-carboxylate (151 mg, 0.439 mmol) were dissolved in toluene (6 mL) and ethanol (2 mL). To the resulting reaction system was added palladium tetrakis(triphenylphosphine)(10 mg) and 2N sodium carbonate solution (0.5 mL). The resulting mixture was reacted under reflux in a nitrogen-protecting atmosphere for 6 h. The reaction mixture was cooled to room temperature and filtered. The organic layer was separated out, concentrated in a reduced pressure, dissolved in dichlormethane, successively washed with water and saturated brine, dried over anhydrous sodium sulfate, and concentrated to dryness to produce 193 mg of the target compound in a yield of 95.2%.

2. Preparation of 2-(1H-pyrrolo[2,3-b]pyridin-3-yl)-10-(3-(trifluoromethyl)phenyl)pyrido[3,2-c][1,5]naphthyridin-9(10H)-one

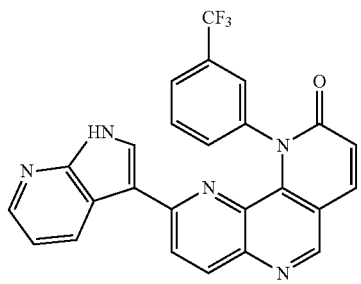 [SMILES: O=c1ccc2cnc3ccc(-c4c[nH]c5ncccc45)nc3c2n1-c1cccc(C(F)(F)F)c1]

The crude tert-butyl 3-(9-oxo-10-(3-(trifluoromethyl)phenyl)-9,10-dihydropyrido[3,2-c][1,5]naphthyridin-2-yl)-1H-pyrrolo[2,3-b]pyridin-1-carboxylate (193 mg, 0.347 mmol) directly obtained in the above step was dissolved in dichlormethane (10 mL). To this system was introduced a gas of hydrogen chloride for 0.5 h. The solid was separated out and filtered by suction. The resulting solid was successively washed with dichlormethane and diethylether. The resulting material was dissolving in water. The resulting solution was adjusted with 1N sodium hydroxide solution to pH=9, and then extracted with ethyl acetate. The organic phase was washed with saturated brine, dried over anhydrous sodium sulfate, filtered by suction, concentrated, and purified with a silica-gel column chromatography (ethyl acetate) to produce 44 mg of the target compound in a yield of 27.7%.

Formula: $C_{25}H_{14}F_3N_5O$ MW: 457.12 MS (M+H): 458.2

$^1$H-NMR (d$_6$-DMSO, 400 MHz): δ 12.16 (1H, s), 9.15 (1H, s), 8.39 (1H, d), 8.35 (1H, d), 8.31-8.24 (2H, m), 8.18 (1H, d), 7.83 (1H, s), 7.77-7.65 (3H, m), 7.17 (1H, dd), 6.96 (1H, d), 6.73 (1H, s).

Example 12

Preparation of 2-(6-(hydroxymethyl)pyridin-3-yl)-10-(3-(trifluoromethyl)phenyl)pyrido[3,2-c][1,5]naphthyridin-9(10H)-one (Compound 18)

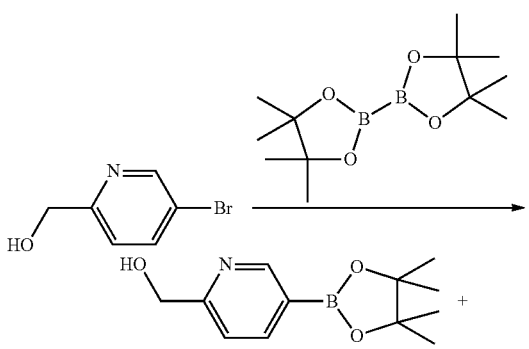

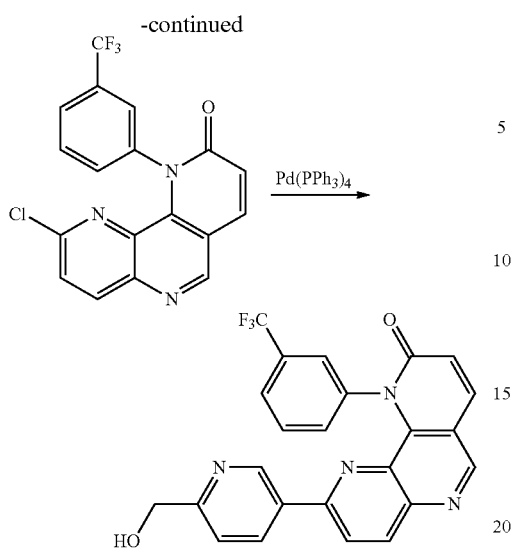

1. Preparation of (5-(4,4,5,5-tetramethyl-1,3,2-di-oxaborolan-2-yl)pyridin-2-yl)methanol

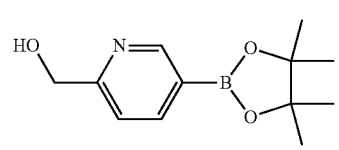 [SMILES: CC1(C)OB(c2ccc(CO)nc2)OC1(C)C]

To 1,4-dioxane (20 mL) was successively added (5-bromopyridin-2-yl)methanol (376 mg, 2.0 mmol), bis(pinacolato)diboron (762 mg, 3.0 mmol), potassium acetate (504 mg, 5.14 mmol) and [1,1'-bis(diphenylphosphino)ferrocene]palladium(II) chloride dichlormethane complex (20 mg). The resulting mixture was reacted under stirring in a nitrogen-protecting atmosphere at 90° C. for 12 hrs. The reaction mixture was cooled and directly used in the next step without a further treatment.

2. Preparation of 2-(6-(hydroxymethyl)pyridin-3-yl)-10-(3-(trifluoromethyl)phenyl)pyrido[3,2-c][1,5]naphthyridin-9(10H)-one

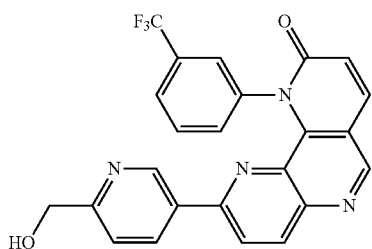 [SMILES: O=c1ccc2cnc3ccc(-c4ccc(CO)nc4)nc3c2n1-c1cccc(C(F)(F)F)c1]

To the cooled reaction liquor of ((5-(4,4,5,5-tetramethyl-1,3,2-dioxaborolan-2-yl)pyridin-2-yl)methanol) obtained in the above step, were added 2-chloro-10-(3-(trifluoromethyl)phenyl)pyrido[3,2-c][1,5]naphthyridin-9(10H)-one (315 mg, 0.84 mmol), palladium tetrakis(triphenylphosphine)(15 mg) and 2N sodium carbonate solution (3.0 mL). This system was reacted in a nitrogen-protecting atmosphere at 90° C. for 16 hrs. The reaction mixture was cooled to room temperature and filtered. The organic layer was separated out, concentrated in a reduced pressure, dissolved in dichloromethane, successively washed with water and saturated brine, dried over anhydrous sodium sulfate, concentrated, and purified with a silica-gel column chromatography (ethyl acetate) to produce 189 mg of the target compound in a yield of 50.0%.

Formula: $C_{24}H_{15}F_3N_4O_2$ MW: 448.11 MS (M+H): 449.2

$^1$H-NMR (d$_6$-DMSO, 400 MHz): δ 9.24 (1H, s), 8.58 (1H, d), 8.49 (1H, d), 8.38 (1H, d), 8.35 (1H, d), 7.89-7.83 (2H, m), 7.73 (1H, t), 7.65 (1H, d), 7.35 (1H, d), 7.25 (1H, dd), 6.99 (1H, d), 5.51 (1H, t), 4.58 (2H, d).

Example 13

Preparation of 2-(6-(4-methylpiperazin-1-yl)pyridin-3-yl)-10-(3-(trifluoromethyl)phenyl)pyrido[3,2-c][1,5]naphthyridin-9(10H)-one (Compound 19)

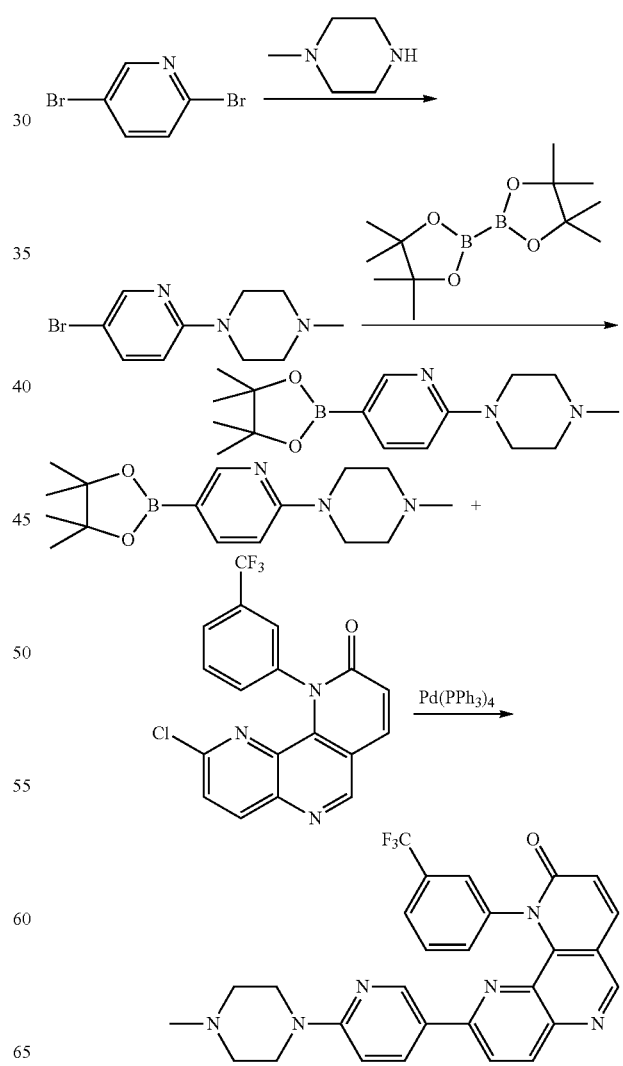

1. Preparation of 1-(5-bromopyridin-2-yl)-4-methylpiperazine

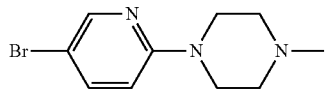

2,5-dibromopyridine (2.00 g, 8.44 mmol) and 1-methylpiperazine (3.00 mL) were stirred at 110° C. for 2 hrs. An excess of 1-methylpiperazine was removed by evaporation in vacuum under a reduced pressure. To the resulting residue was added a saturated sodium bicarbonate solution. The resulting solution was extracted with ethyl acetate. The organic phase was dried with anhydrous sodium sulfate, and filtered. The organic solvent was removed under a reduced pressure to produce 1.45 g of the title compound as a brown solid in a yield of 67.1%.

2. Preparation of 1-methyl-4-(5-(4,4,5,5-tetramethyl-1,3,2-dioxaborolan-2-yl)pyridin-2-yl)piperazine

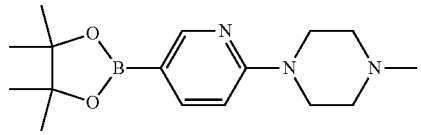

To 1,4-dioxane (20 mL) was successively added 1-(5-bromopyridin-2-yl)-4-methylpiperazine (0.67 g, 2.62 mmol), bis(pinacolato)diboron (1.00 g, 3.94 mmol), potassium acetate (0.65 g, 6.63 mmol) and [1,1'-bis(diphenylphosphino)ferrocene]palladium(II) chloride dichlormethane complex (15 mg). The resulting mixture was reacted under stirring in a nitrogen-protecting atmosphere at 90° C. for 12 hrs. The reaction mixture was cooled and directly used in the next step without a further treatment.

3. Preparation of 2-(6-(4-methylpiperazin-1-yl)pyridin-3-yl)-10-(3-(trifluoromethyl)phenyl)pyrido[3,2-c][1,5]naphthyridin-9(10H)-one

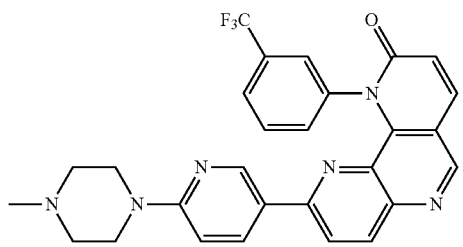 [SMILES: CN1CCN(c2ccc(-c3ccc4ncc5ccc(=O)n(-c6cccc(C(F)(F)F)c6)c5c4n3)cn2)CC1]

To the cooled reaction liquor of (1-methyl-4-(5-(4,4,5,5-tetramethyl-1,3,2-dioxaborolan-2-yl)pyridin-2-yl)piperazine) obtained in the above step, were added 2-chloro-10-(3-(trifluoromethyl)phenyl)pyrido[3,2-c][1,5]naphthyridin-9(10H)-one (0.68 g, 1.81 mmol), palladium tetrakis (triphenylphosphine) (15 mg) and 2N sodium carbonate solution (3.9 mL). This system was reacted in a nitrogen-protecting atmosphere at 90° C. for 16 h, cooled to the room temperature and filtered. The organic layer was separated out, concentrated in a reduced pressure, dissolved in dichlormethane, successively washed with water and saturated brine, dried over anhydrous sodium sulfate, concentrated, and purified with a silica-gel column chromatography (ethyl acetate) to produce 518 mg of the target compound in a yield of 55.6%.

Formula: $C_{28}H_{23}F_3N_6O$ MW: 516.19 MS (M+H): 517.3

$^1$H-NMR (CDCl$_3$, 400 MHz): δ 8.99 (1H, s), 8.35 (1H, d), 8.33 (1H, d), 8.02 (1H, d), 7.94 (1H, d), 7.76 (1H, d), 7.69 (1H, s), 7.63 (1H, t), 7.42 (1H, d), 6.99 (1H, d), 6.94 (1H, dd), 6.46 (1H, d), 3.75-3.67 (4H, m), 2.64-2.56 (4H, m), 2.40 (3H, s).

Example 14

Preparation of 2-(6-(1H-pyrazol-1-yl)pyridin-3-yl)-10-(3-(trifluoromethyl)phenyl)pyrido[3,2-c][1,5]naphthyridin-9(10H)-one (Compound 20)

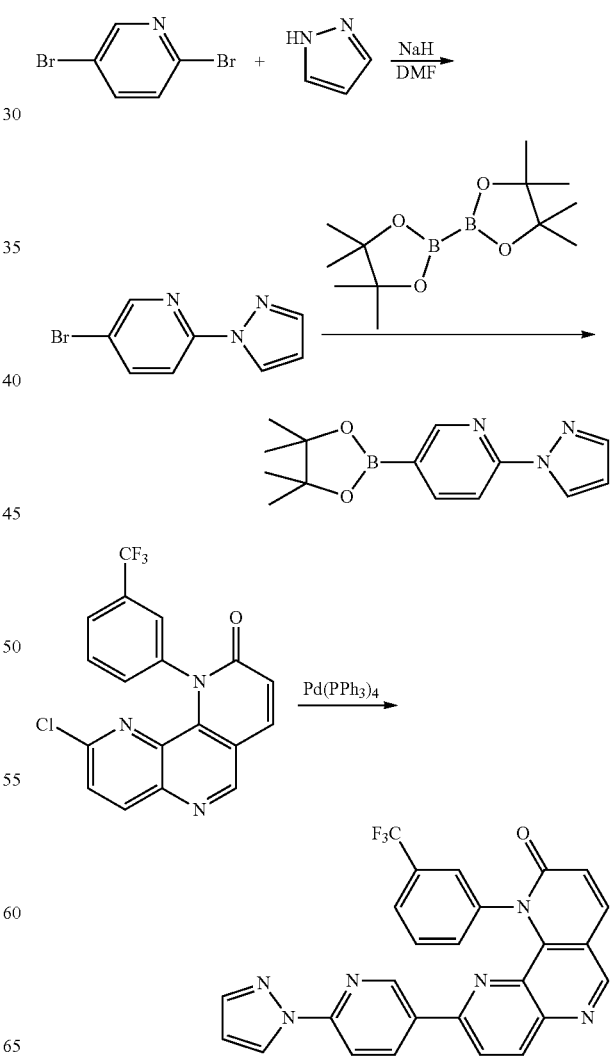

1. Preparation of 5-bromo-2-(1H-pyrazol-1-yl)pyridine

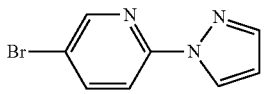

To a solution of 60% sodium hydride (1.20 g, 30.0 mmol) in N,N-dimethyl formamide (40 mL) was added pyrazole (2.05 g, 30.1 mmol) in batch. The resulting mixture was reacted under stirring at room temperature for an hour. Then to the reaction system was added 2,5-dibromopyridine (4.75 g, 20.1 mmol). The resulting mixture was reacted under stirring at 100° C. for 2 hrs. The reaction mixture was cooled and poured into an ice water, The solid was separated out and filtered by suction. The resulting solid was dired in vacuum and recrystallized with n-hexane to produce 3.31 g of the title compound as brown solid in a yield of 73.6%.

2. Preparation of 2-(1H-pyrazol-1-yl)-5-(4,4,5,5-tetramethyl-1,3,2-dioxaborolan-2-yl)pyridine

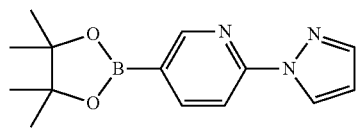 [SMILES: CC1(C)OB(c2ccc(-n3cccn3)nc2)OC1(C)C]

To 1,4-dioxane (20 mL) was successively added 5-bromo-2-(1H-pyrazol-1-yl)pyridine (0.45 g, 2.01 mmol), bis(pinacolato)diboron (0.76 g, 2.99 mmol), potassium acetate (0.51 g, 5.20 mmol) and [1,1'-bis(diphenylphosphino)ferrocene]palladium(II) chloride dichlormethane complex (15 mg). The resulting mixture was reacted under stirring in a nitrogen-protecting atmosphere at 90° C. for 5 hrs. The reaction mixture was cooled and directly used in the next step without a further treatment.

3. Preparation of 2-(6-(1H-pyrazol-1-yl)pyridin-3-yl)-10-(3-(trifluoromethyl)phenyl)pyrido[3,2-c][1,5]naphthyridin-9(10H)-one

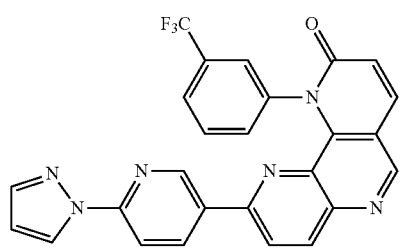 [SMILES: O=c1ccc2cnc3ccc(-c4ccc(-n5cccn5)nc4)nc3c2n1-c1cccc(C(F)(F)F)c1]

To the cooled reaction liquor of (2-(1H-pyrazol-1-yl)-5-(4,4,5,5-tetramethyl-1,3,2-dioxaborolan-2-yl)pyridine) obtained in the above step, were added 2-chloro-10-(3-(trifluoromethyl)phenyl)pyrido[3,2-c][1,5]naphthyridin-9(10H)-one (300 mg, 0.799 mmol), palladium tetrakis(triphenylphosphine) (15 mg) and 2N sodium carbonate solution (3 mL). This system was reacted in a nitrogen-protecting atmosphere at 90° C. for 16 hrs. The reaction mixture was cooled to room temperature and filtered. The organic layer was separated out, concentrated in a reduced pressure, dissolved in dichlormethane, successively washed with water and saturated brine, dried over anhydrous sodium sulfate, concentrated, and purified with a silica-gel column chromatography (ethyl acetate) to produce 291 mg of the target compound in a yield of 75.2%.

Formula: $C_{26}H_{15}F_3N_6O$ MW: 484.13 MS (M+H): 485.2
$^1$H-NMR ($d_6$-DMSO, 400 MHz): δ 9.24 (1H, s), 8.62 (1H, d), 8.54 (1H, d), 8.50 (1H, d), 8.38 (1H, d), 8.36 (1H, d), 7.93 (1H, d), 7.91-7.87 (2H, m), 7.79-7.72 (2H, m), 7.65 (1H, d), 7.38 (1H, dd), 6.99 (1H, d), 6.62 (1H, t).

Example 15

Preparation of 2-(4-(2-(2-methoxypyrimidin-5-yl)-9-oxopyrido[3,2-c][1,5]naphthyridin-10(9H)-yl)phenyl)-2-methylpropanenitrile (Compound 21)

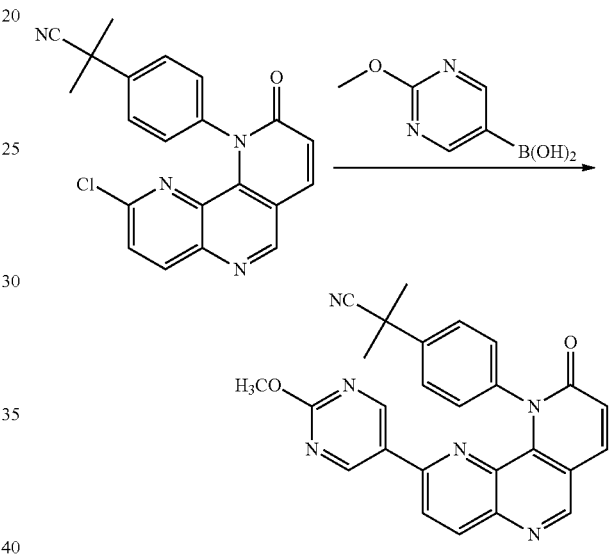

The specific procedure was the same as those in Example 1, Step 4, except for substituting 2-(4-(2-chloro-9-oxopyrido[3,2-c][1,5]naphthyridin-10(9H)-yl)phenyl)-2-methyl propanenitrile (166 mg, 0.443 mmol) and 2-methoxypyrimidin-5-yl boric acid respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 157 mg of the target compound in a yield of 79.0%.

Formula: $C_{26}H_{20}N_6O_2$ MW: 448.16 MS (M+H): 449.2
$^1$H-NMR ($d_6$-DMSO, 400 MHz): δ 9.19 (1H, s), 8.45 (1H, d), 8.37 (2H, s), 8.32 (1H, d), 8.27 (1H, d), 7.63 (2H, d), 7.37 (2H, d), 6.96 (1H, d), 3.96 (3H, s), 1.78 (6H, s).

Example 16

Preparation of 2-(6-(methylsulfonyl)pyridin-3-yl)-10-(3-(trifluoromethyl)phenyl)pyrido[3,2-c][1,5]naphthyridin-9(10H)-one (Compound 22)

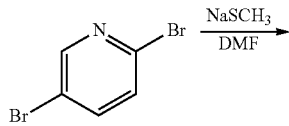

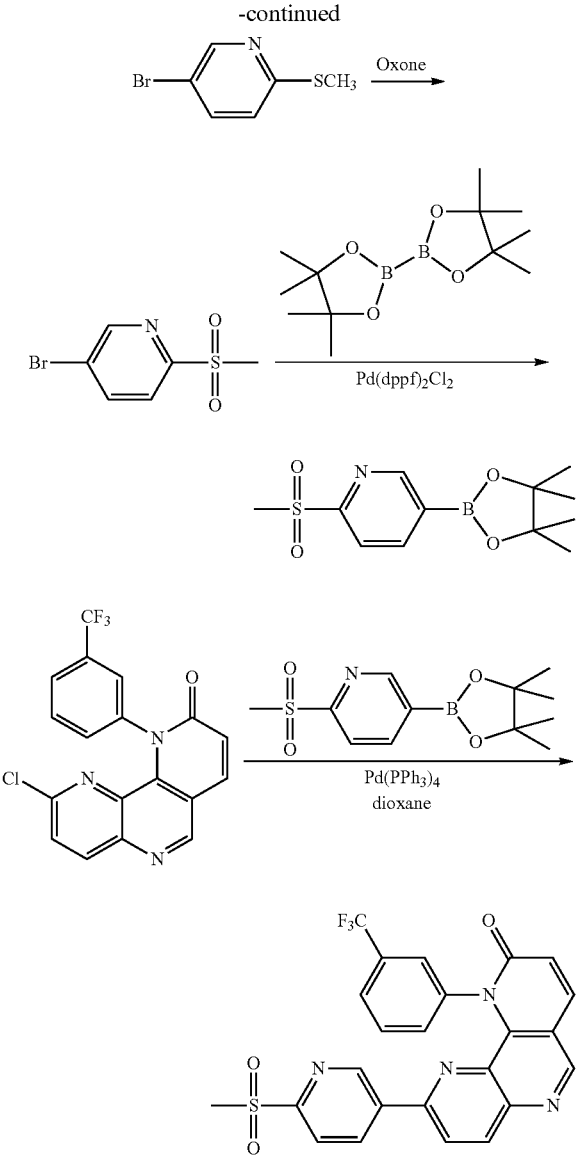

1. Preparation of 5-bromo-2-(methylthio)pyridine

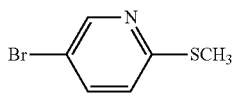

2,5-dibromopyridine (3.0 g, 12.66 mmol) was dissolved in N,N-dimethyl formamide (20 mL). To the resulting solution was added sodium methyl mercaptide (1.1 g, 15.69 mmol). The resulting mixture was placed in an ice-bath in the nitrogen protection to react with stirring for 16 hrs. The reaction mixture was poured into water (150 mL). The solid was separated out and filtered by suction. The resulting solid was dired to produce 2.5 g of the title compound as white solid crude, which was directly used in the next step.

2. Preparation of 5-bromo-2-(methylsulfonyl)pyridine

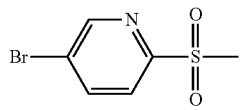

2.5 g of the crude 5-bromo-2-(methylthio)pyridine directly obtained in the above step was dissolved in a mixed solution of isopropanol (10 mL) and water (5 mL). To the resulting mixture was added a compound salt of potassium monopersulfate (15.7 g, 25.5 mmol). The resulting material was stirred overnight at room temperature and filtered. The filtrate was concentrated and then dissolved in ethyl acetate. The resulting material was successively washed with water and saturated brine, dried with anhydrous magnesium sulfate, and filtered. The filtrate was concentrated in a reduced pressure, and then purified with a silica-gel column chromatography (petroleum ether:ethyl acetate=5:1) to produce 0.43 g of the title compound as a white solid in a yield (two steps) of 14.4%.

3. Preparation of 2-(methylsulfonyl)-5-(4,4,5,5-tetramethyl-1,3,2-dioxaborolan-2-yl)pyridine

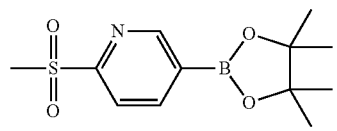

To 1,4-dioxane (20 mL) was successively added 5-bromo-2-(methylsulfonyl)pyridine (0.200 g, 0.847 mmol), bis(pinacolato)diboron (433 mg, 1.71 mmol), potassium acetate (167 m g, 1.70 mmol) and [1,1'-bis(diphenylphosphino)ferrocene]palladium(II) chloride dichlormethane complex (50 mg). The resulting mixture was reacted under stirring in a nitrogen-protecting atmosphere at 90° C. for 5 hrs. The reaction mixture was cooled and directly used in the next step without a further treatment.

4. Preparation of 2-(6-(methylsulfonyl)pyri din-3-yl)-10-(3-(trifluoromethyl)phenyl)pyrido[3,2-c][1,5]naphthyridin-9(10H)-one

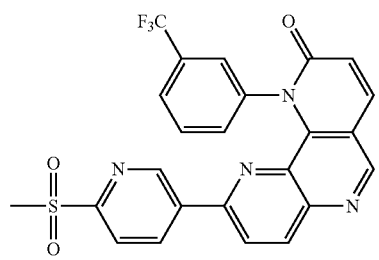 [SMILES: CS(=O)(=O)c1ccc(-c2ccc3ncc4ccc(=O)n(-c5cccc(C(F)(F)F)c5)c4c3n2)cn1]

To the cooled reaction liquor of 2-(methylsulfonyl)-5-(4, 4,5,5-tetramethyl-1,3,2-dioxaborolan-2-yl)pyridine obtained in the above step, were added 2-chloro-10-(3-(trifluoromethyl)phenyl)pyrido[3,2-c][1,5]naphthyridin-9

(10H)-one (319 mg, 0.85 mmol), palladium tetrakis(triphenylphosphine) (15 mg) and 2N sodium carbonate solution (1.3 mL). This system was reacted in a nitrogen-protecting atmosphere at 90° C. for 16 hrs. The reaction mixture was cooled to room temperature and filtered. The organic layer was separated out, concentrated in a reduced pressure, dissolved in dichlormethane, successively washed with water and saturated brine, dried over anhydrous sodium sulfate, concentrated, and purified with a silica-gel column chromatography (ethyl acetate) to produce 58 mg of the target compound in a yield of 13.7%.

Formula: $C_{24}H_{15}F_3N_4O_3S$ MW: 496.08 MS (M+H): 497.1

$^1$H-NMR ($d_6$-DMSO, 400 MHz): δ 9.35 (1H, s), 8.74 (1H, d), 8.63 (1H, d), 8.50 (1H, d), 8.44 (1H, d), 7.99-7.89 (3H, m), 7.82 (1H, t), 7.73 (1H, d), 7.68 (1H, dd), 7.07 (1H, d), 3.36 (3H, s).

Example 17

Preparation of 2-(6-methoxypyridin-3-yl)-10-(3-(trifluoromethyl)phenyl)pyrido[3,2-c][1,5]naphthyridin-9(10H)-one (Compound 23)

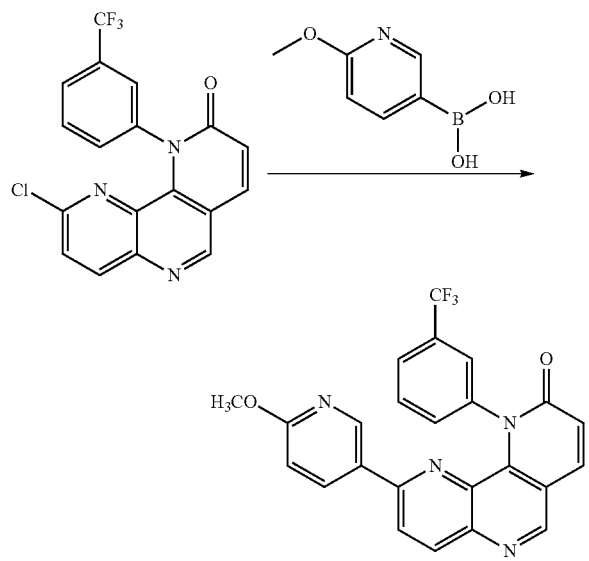

The specific processure was the same as those in Example 1, Step 4, except for substituting 2-chloro-10-(3-(trifluoromethyl)phenyl)pyrido[3,2-c][1,5]naphthyridin-9(10H)-one (100 mg, 0.266 mmol) and 6-methoxy-3-pyridine boric acid respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 82 mg of the target compound in a yield of 68.8%.

Formula: $C_{24}H_{15}F_3N_4O_2$ MW: 448.11 MS (M+H): 449.1

$^1$H-NMR ($d_6$-DMSO, 400 MHz): δ 9.22 (1H, s), 8.45 (1H, d), 8.39-8.34 (2H, m), 8.29 (1H, d), 7.92-7.84 (2H, m), 7.74 (1H, t), 7.63 (1H, d), 7.10 (1H, dd), 6.99 (1H, d), 6.66 (1H, d), 3.90 (3H, s).

Example 18

Preparation of 2-(6-morpholinopyridin-3-yl)-10-(3-(trifluoromethyl)phenyl)pyrido[3,2-c][1,5]naphthyridin-9(10H)-one (Compound 24)

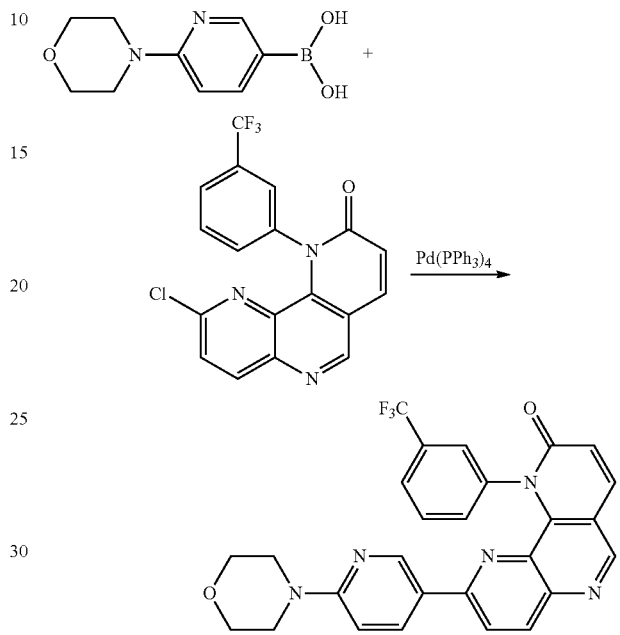

The specific processure was the same as those in Example 1, Step 4, except for substituting 2-chloro-10-(3-(trifluoromethyl)phenyl)pyrido[3,2-c][1,5]naphthyridin-9(10H)-one (150 mg, 0.399 mmol) and 6-morpholinopyridin-3-yl boric acid (100 mg, 0.481 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 78 mg of the target compound in a yield of 38.8%.

Formula: $C_{27}H_{20}F_3N_5O_2$ MW: 503.16 MS (M+H): 504.2

$^1$H-NMR ($d_6$-DMSO, 400 MHz): δ 9.16 (1H, s), 8.37 (1H, d), 8.34 (1H, d), 8.28 (1H, d), 8.22 (1H, d), 7.90 (1H, d), 7.84 (1H, s), 7.73 (1H, t), 7.62 (1H, d), 7.00 (1H, dd), 6.97 (1H, s), 6.62 (1H, d), 3.71 (4H, t), 3.53 (4H, t).

Example 19

Preparation of 2-(5-methoxypyridin-3-yl)-10-(3-(trifluoromethyl)phenyl)pyrido[3,2-c][1,5]naphthyridin-9(10H)-one (Compound 25)

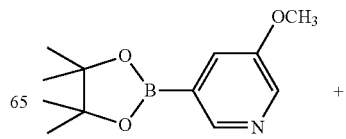

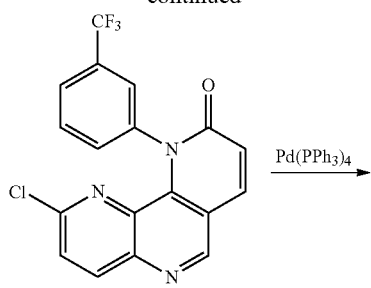

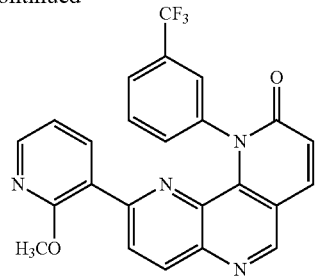

The specific processure was the same as those in Example 1, Step 4, except for substituting 2-chloro-10-(3-(trifluoromethyl)phenyl)pyrido[3,2-c][1,5]naphthyridin-9(10H)-one (150 mg, 0.399 mmol) and 2-methoxypyridin-3-yl boric acid (74 mg, 0.484 mmol) respectively for 2-chloro-10-(3-(trifluoromethyl)phenyl)pyrido[3,2-c][1,5]naphthyridin-9 (10H)-one and 5-(4,4,5,5-tetramethyl-1,3,2-dioxaborolan-2-yl)pyridin-2-amine to produce 107 mg of the target compound in a yield of 59.9%.

Formula: $C_{24}H_{15}F_3N_4O_2$ MW: 448.11 MS (M+H): 449.1

$^1$H-NMR ($d_6$-DMSO, 400 MHz): δ 9.25 (1H, s), 8.43 (1H, d), 8.37 (1H, d), 8.24 (1H, d), 8.20 (1H, dd), 7.82 (1H, s), 7.74 (1H, d), 7.65 (1H, t), 7.60 (1H, d), 6.98 (1H, d), 6.84 (1H, dd), 6.72 (1H, dd), 3.90 (3H, s).

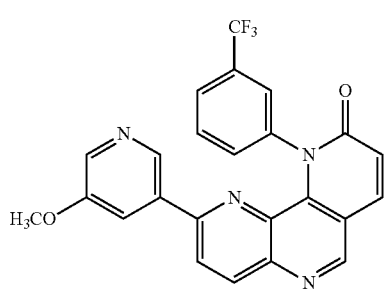

The specific processure was the same as those in Example 1, Step 4, except for substituting 2-chloro-10-(3-(trifluoromethyl)phenyl)pyrido[3,2-c][1,5]naphthyridin-9(10H)-one (150 mg, 0.399 mmol) and 3-methoxy-5-(4,4,5,5-tetramethyl-1,3,2-dioxaborolan-2-yl)-pyridine (113 mg, 0.48 mmol) respectively for 2-chloro-10-(3-(trifluoromethyl) phenyl)pyrido[3,2-c][1,5]naphthyridin-9(10H)-one and 5-(4,4,5,5-tetramethyl-1,3,2-dioxaborolan-2-yl)pyridin-2-amine to produce 87 mg of the target compound in a yield of 48.6%.

Formula: $C_{24}H_{15}F_3N_4O_2$ MW: 448.11 MS (M+H): 449.1

$^1$H-NMR ($d_6$-DMSO, 400 MHz): δ 9.26 (1H, s), 8.51 (1H, d), 8.37 (1H, d), 8.35 (1H, d), 8.31 (1H, d), 7.85-7.75 (3H, m), 7.74-7.63 (2H, m), 7.24 (1H, s), 6.99 (1H, d), 3.89 (3H, s).

Example 20

Preparation of 2-(2-methoxypyridin-3-yl)-10-(3-(trifluoromethyl)phenyl)pyrido[3,2-c][1,5]naphthyridin-9(10H)-one (Compound 26)

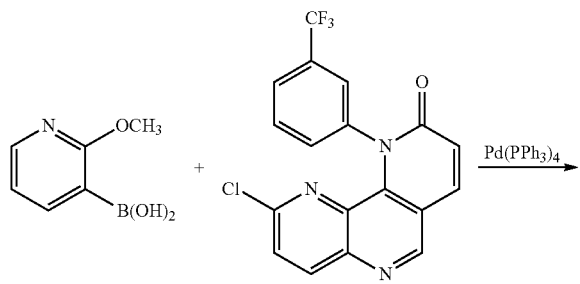

Example 21

Preparation of 10-(3-(trifluoromethyl)phenyl)-2-(6-(trifluoromethyl)pyridin-3-yl)pyrido[3,2-c][1,5] naphthyridin-9(10H)-one (Compound 27)

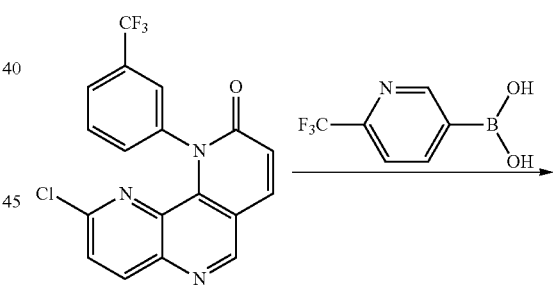

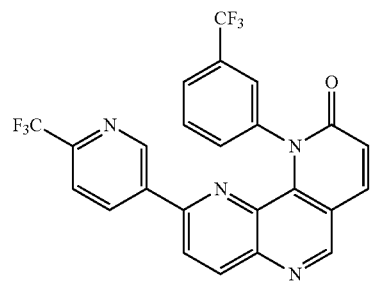

The specific processure was the same as those in Example 1, Step 4, except for substituting 2-chloro-10-(3-(trifluoromethyl)phenyl)pyrido[3,2-c][1,5]naphthyridin-9(10H)-one (150 mg, 0.399 mmol) and 6-(trifluoromethyl)pyridin-3-yl boric acid (92 mg, 0.482 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 102 mg of the target compound in a yield of 52.6%.

Formula: $C_{24}H_{12}F_6N_4O$ MW: 486.09 MS (M+H): 487.1

$^1$H-NMR (d$_6$-DMSO, 400 MHz): δ 9.29 (1H, s), 8.66 (1H, s), 8.57 (1H, d), 8.42 (1H, d), 8.38 (1H, d), 7.88 (1H, d), 7.85-7.75 (3H, m), 7.69 (1H, d), 7.59 (1H, d), 7.01 (1H, d).

Example 22

Preparation of 2-(6-methylpyridin-3-yl)-10-(3-(trifluoromethyl)phenyl)pyrido[3,2-c][1,5]naphthyridin-9(10H)-one (Compound 28)

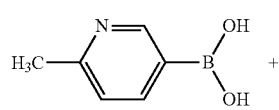

+

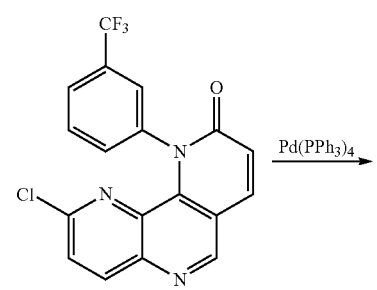

Pd(PPh$_3$)$_4$ →

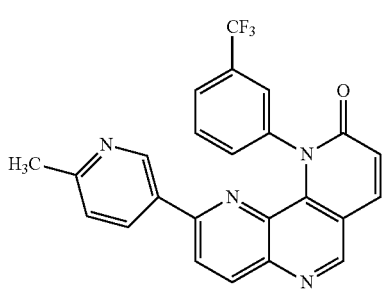

The specific processure was the same as those in Example 1, Step 4, except for substituting 2-chloro-10-(3-(trifluoromethyl)phenyl)pyrido[3,2-c][1,5]naphthyridin-9(10H)-one (225 mg, 0.599 mmol) and 6-methylpyridin-3-yl boric acid (99 mg, 0.723 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 160 mg of the target compound in a yield of 61.8%.

Formula: $C_{24}H_{15}F_3N_4O$ MW: 432.12 MS (M+H): 433.2

$^1$H-NMR (CDCl$_3$, 400 MHz): δ 9.06 (1H, s), 8.61 (1H, s), 8.46 (1H, d), 8.05 (1H, d), 8.03 (1H, d), 7.76 (1H, d), 7.66 (1H, d), 7.63 (1H, s), 7.47 (1H, d), 7.07-7.00 (3H, m), 2.60 (3H, s).

Example 23

Preparation of 2-(3,5-dimethylisoxazol-4-yl)-10-(3-(trifluoromethyl)phenyl)pyrido[3,2-c][1,5]naphthyridin-9(10H)-one (Compound 29)

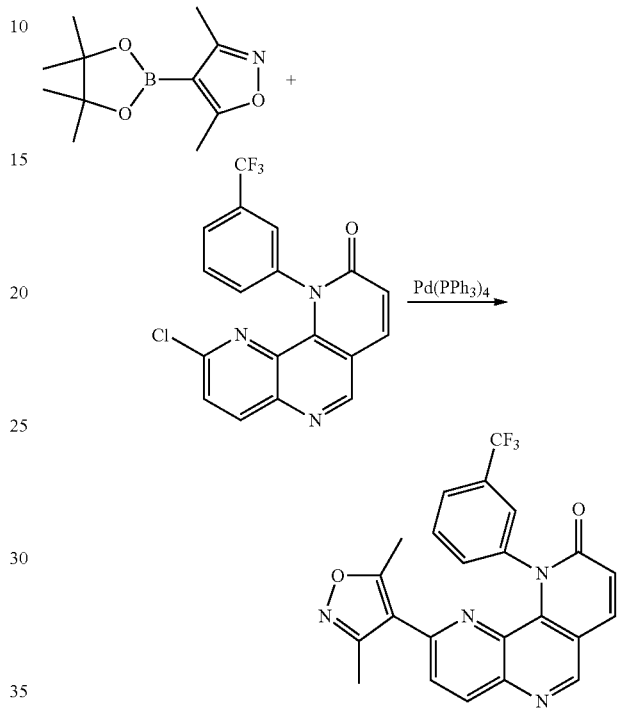

The specific processure was the same as those in Example 1, Step 4, except for substituting 2-chloro-10-(3-(trifluoromethyl)phenyl)pyrido[3,2-c][1,5]naphthyridin-9(10H)-one (188 mg, 0.50 mmol) and 3,5-dimethyl-4-(4,4,5,5-tetramethyl-1,3,2-dioxaborolan-2-yl)-isoxazole (134 mg, 0.575 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 112 mg of the target compound in a yield of 51.4%.

Formula: $C_{23}H_{15}F_3N_4O_2$ MW: 436.11 MS (M+H): 437.1

$^1$H-NMR (d$_6$-DMSO, 400 MHz): δ 9.26 (1H, s), 8.45 (1H, d), 8.37 (1H, d), 7.76 (1H, d), 7.65-7.55 (3H, m), 7.50 (1H, d), 7.00 (1H, d), 2.11 (3H, s), 1.89 (3H, s).

Example 24

Preparation of 2-(5-fluoropyridin-3-yl)-10-(3-(trifluoromethyl)phenyl)pyrido[3,2-c][1,5]naphthyridin-9(10H)-one (Compound 30)

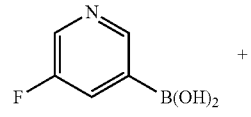 +

-continued

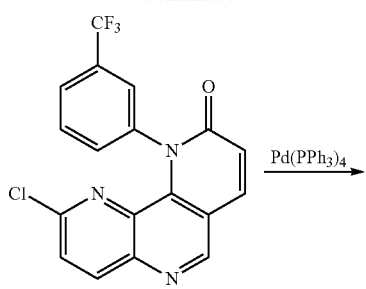

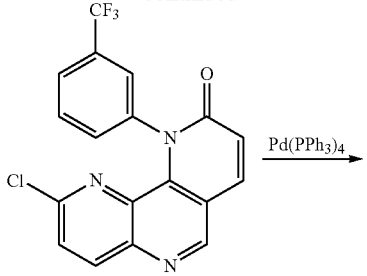

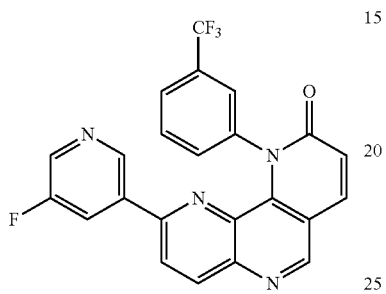

The specific processure was the same as those in Example 1, Step 4, except for substituting 2-chloro-10-(3-(trifluoromethyl)phenyl)pyrido[3,2-c][1,5]naphthyridin-9(10H)-one (200 mg, 0.53 mmol) and 5-fluoropyridin-3-yl boric acid (90 mg, 0.64 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 162 mg of the target compound in a yield of 69.8%.

Formula: $C_{23}H_{12}F_4N_4O$ MW: 436.09 MS (M+H): 437.1

$^1$H-NMR (d$_6$-DMSO, 400 MHz): δ 9.29 (1H, s), 8.61 (1H, d), 8.55 (1H, d), 8.50 (1H, t), 8.42 (1H, d), 8.39 (1H, d), 7.87 (1H, s), 7.81 (1H, d), 7.75 (1H, t), 7.69 (1H, d), 7.14 (1H, dt), 7.01 (1H, d).

Example 25

Preparation of 10-(3-(trifluoromethyl)phenyl-2-(5-(trifluoromethyl)pyridin-3-yl)pyrido[3,2-c][1,5]naphthyridin-9(10H)-one (Compound 31)

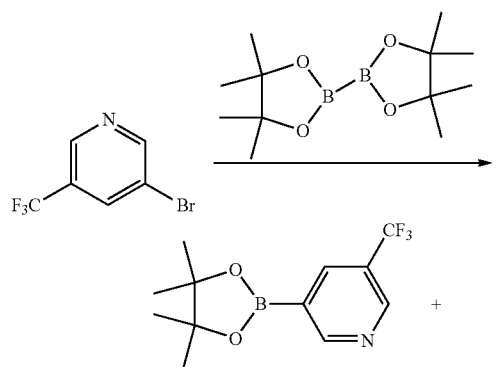

1. Preparation of 3-(4,4,5,5-tetramethyl-1,3,2-dioxaborolan-2-yl)-5-(trifluoromethyl)pyridine

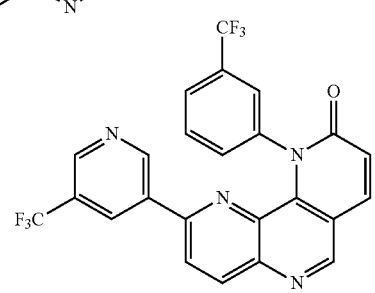

To 1,4-dioxane (20 mL) was successively added 3-bromo-5-trifluoromethylpyridine (273 mg, 1.21 mmol), bis(pinacolato)diboron (460 mg, 1.81 mmol), potassium acetate (300 mg, 3.06 mmol) and [1,1'-bis(diphenylphosphino)ferrocene]palladium(II) chloride dichlormethane complex (15 mg). The resulting mixture was reacted under stirring in a nitrogen-protecting atmosphere at 90° C. for 12 hrs. The reaction mixture was cooled and directly used in the next step without a further treatment.

2. Preparation of 10-(3-(trifluoromethyl)phenyl-2-(5-(trifluoromethyl)pyridin-3-yl)pyrido[3,2-c][1,5]naphthyridin-9(10H)-one

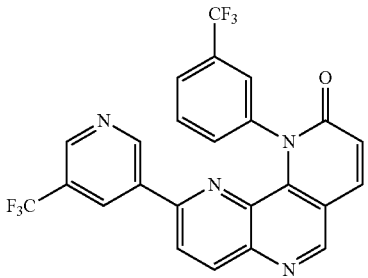 [SMILES: O=c1ccc2cnc3ccc(-c4cncc(C(F)(F)F)c4)nc3c2n1-c1cccc(C(F)(F)F)c1]

To the cooled reaction liquor of 3-(4,4,5,5-tetramethyl-1,3,2-dioxaborolan-2-yl)-5-(trifluoromethyl)pyridine obtained in the above step, were added 2-chloro-10-(3-(trifluoromethyl)phenyl)pyrido[3,2-c][1,5]naphthyridin-9(10H)-one (300 mg, 0.799 mmol), palladium tetrakis(triphenylphosphine) (15 mg) and 2N sodium carbonate solution (1.8 mL). This system was reacted in a nitrogen-protecting atmosphere at 90° C. for 16 hrs. The reaction mixture was cooled to room temperature and filtered. The organic layer was separated out, concentrated in a reduced pressure, dissolved in dichlormethane, successively washed with water and saturated brine, dried over anhydrous sodium sulfate, concentrated, and purified with a silica-gel column chromatography (ethyl acetate) to produce 72 mg of the target compound in a yield of 18.5%.

Formula: $C_{24}H_{12}F_6N_4O$ MW: 486.09 MS (M+H): 487.1

$^1$H-NMR (d$_6$-DMSO, 400 MHz): δ 9.29 (1H, s), 9.00 (1H, s), 8.55 (1H, d), 8.44 (1H, d), 8.41-8.36 (2H, m), 8.12 (1H, s), 7.78 (1H, s), 7.76-7.71 (3H, m), 7.01 (1H, d).

Example 26

Preparation of 2-(1-methyl-1H-pyrazol-5-yl)-10-(3-(trifluoromethyl)phenyl)pyrido[3,2-c][1,5]naphthyridin-9(10H)-one (Compound 32)

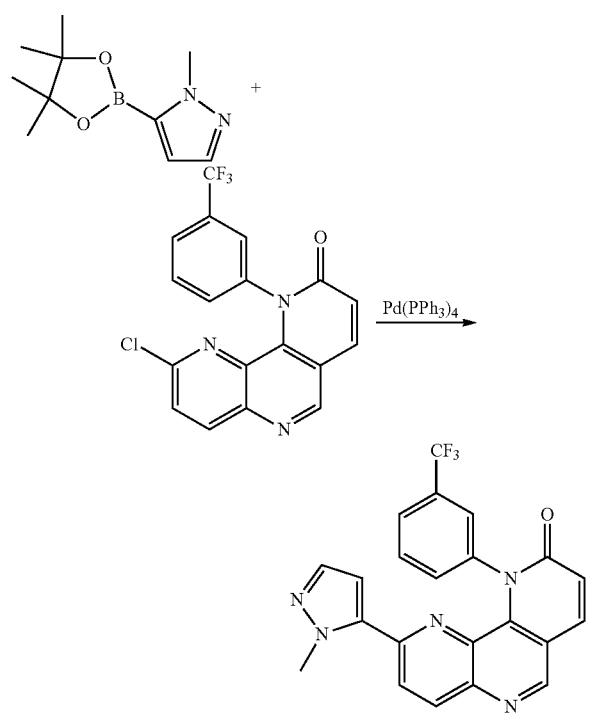

The specific processure was the same as those in Example 1, Step 4, except for substituting 2-chloro-10-(3-(trifluoromethyl)phenyl)pyrido[3,2-c][1,5]naphthyridin-9(10H)-one (188 mg, 0.50 mmol) and 1-methyl-5-(4,4,5,5-tetramethyl-1,3,2-dioxaborolan-2-yl)-1H-pyrazole (127 mg, 0.61 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 105 mg of the target compound in a yield of 49.8%.

Formula: $C_{22}H_{14}F_3N_5O$ MW: 421.12 MS (M+H): 422.1

$^1$H-NMR (d$_6$-DMSO, 400 MHz): δ 9.27 (1H, s), 8.48 (1H, d), 8.38 (1H, d), 7.95 (1H, d), 7.74 (1H, s), 7.64-7.55 (3H, m), 7.35 (1H, d), 7.00 (1H, d), 6.05 (1H, d), 3.58 (3H, s).

Example 27

Preparation of 2-(thiazol-5-yl)-10-(3-(trifluoromethyl)phenyl)pyrido[3,2-c][1,5]naphthyridin-9(10H)-one (Compound 33)

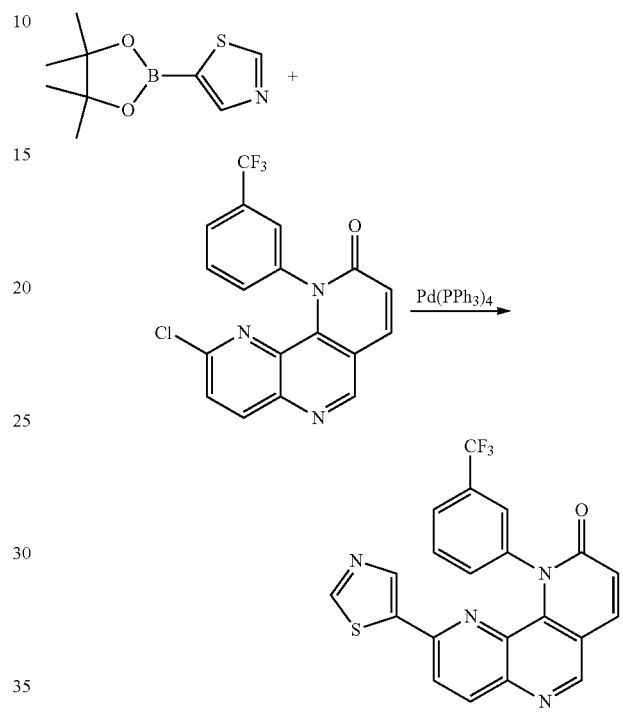

The specific processure was the same as those in Example 1, Step 4, except for substituting 2-chloro-10-(3-(trifluoromethyl)phenyl)pyrido[3,2-c][1,5]naphthyridin-9(10H)-one (188 mg, 0.50 mmol) and 5-(4,4,5,5-tetramethyl-1,3,2-dioxaborolan-2-yl)-thiazole (125 mg, 0.59 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 71 mg of the target compound in a yield of 33.6%.

Formula: $C_{21}H_{11}F_3N_4OS$ MW: 424.06 MS (M+H): 425.1

$^1$H-NMR (d$_6$-DMSO, 400 MHz): δ 9.22 (1H, s), 9.10 (1H, s), 8.46 (1H, d), 8.37 (1H, s), 8.35 (1H, d), 8.28 (1H, d), 7.85-7.80 (2H, m), 7.75 (1H, t), 7.59 (1H, d), 6.97 (1H, d).

Example 28

Preparation of 3-methyl-5-(9-oxo-10-(3-(trifluoromethyl)phenyl)-9,10-dihydropyrido[3,2-c][1,5]naphthyridin-2-yl)-2-cyanopyridine (Compound 34)

87
-continued

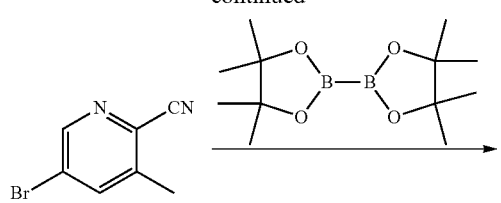

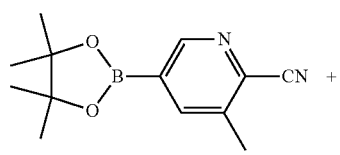

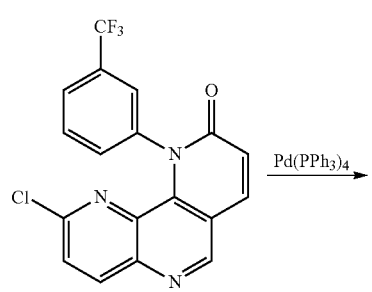

1. Preparation of 5-bromo-3-methyl-2-cyanopyridine

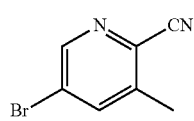

To a solution of 2,5-dibromo-3-methylpyridine (5.0 g, 19.9 mmol) in N,N-dimethyl formamide (20 mL) was added cuprous cyanide (1.8 g, 20.0 mmol). The resulting mixture was reacted at 120° C. under stirring for 12 hrs. The reaction mixture was cooled, to which water was added. The resulting mixture was extracted with ethyl acetate. The organic phase was washed with saturated brine, dried with anhydrous sodium sulfate, and filtered. The filtrate was concentrated and purified with a silica-gel column chromatography (petroleum ether:ethyl acetate=5:1) to produce 2.4 g of the title compound as a white solid in a yield of 61.3%.

88

2. Preparation of 3-methyl-5-(4,4,5,5-tetramethyl-1,3,2-dioxaborolan-2-yl)-2-cyanopyridine

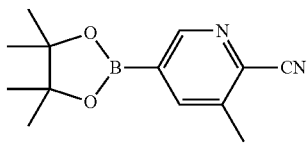 [SMILES: Cc1cc(B2OC(C)(C)C(C)(C)O2)cnc1C#N]

To 1,4-dioxane (20 mL) was successively added 5-bromo-3-methyl-2-cyanopyridine (390 mg, 1.98 mmol), bis(pinacolato)diboron (754 mg, 2.97 mmol), potassium acetate (493 mg, 5.03 mmol) and [1,1'-bis(diphenylphosphino)ferrocene] palladium(II) chloride dichlormethane complex (20 mg). The resulting mixture was reacted under stirring in a nitrogen-protecting atmosphere at 90° C. for 12 hrs. The reaction mixture was cooled and directly used in the next step without a further treatment.

3. Preparation of 3-methyl-5-(9-oxo-10-(3-(trifluoromethyl)phenyl)-9,10-dihydropyrido[3,2-c][1,5]naphthyridin-2-yl)-2-cyanopyridine

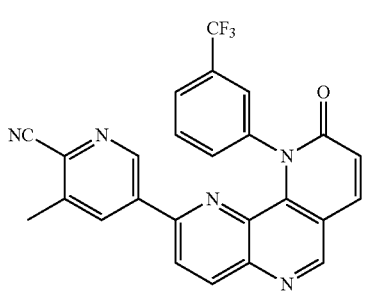 [SMILES: Cc1cc(-c2ccc3ncc4ccc(=O)n(-c5cccc(C(F)(F)F)c5)c4c3n2)cnc1C#N]

To the cooled reaction liquor of 3-methyl-5-(4,4,5,5-tetramethyl-1,3,2-dioxaborolan-2-yl)-2-cyanopyridine obtained in the above step, was added 2-chloro-10-(3-(trifluoromethyl)phenyl)pyrido[3,2-c][1,5]naphthyridin-9 (10H)-one (500 mg, 1.33 mmol), palladium tetrakis(triphenylphosphine) (15 mg) and 2N sodium carbonate solution (3.0 mL). This system was reacted in a nitrogen-protecting atmosphere at 90° C. for 16 hrs. The reaction mixture was cooled to room temperature and filtered. The organic layer was separated out, concentrated in a reduced pressure, dissolved in dichlormethane, successively washed with water and saturated brine, dried over anhydrous sodium sulfate, concentrated, and purified with a silica-gel column chromatography (ethyl acetate) to produce 192 mg of the target compound in a yield of 31.6%.

Formula: $C_{25}H_{14}F_3N_5O$ MW: 457.12 MS (M+H): 458.1

$^1$H-NMR (d$_6$-DMSO, 400 MHz): δ 9.30 (1H, s), 8.58 (1H, d), 8.40 (1H, d), 8.38 (1H, d), 8.20 (1H, d), 7.87 (1H, d), 7.82-7.72 (4H, m), 7.02 (1H, d), 2.52 (3H, s).

Example 29

Preparation of 5-(9-oxo-10-(3-(trifluoromethyl)phenyl)-9,10-dihydropyrido[3,2-c][1,5]naphthyridin-2-yl)-3-cyanopyridine (Compound 35)

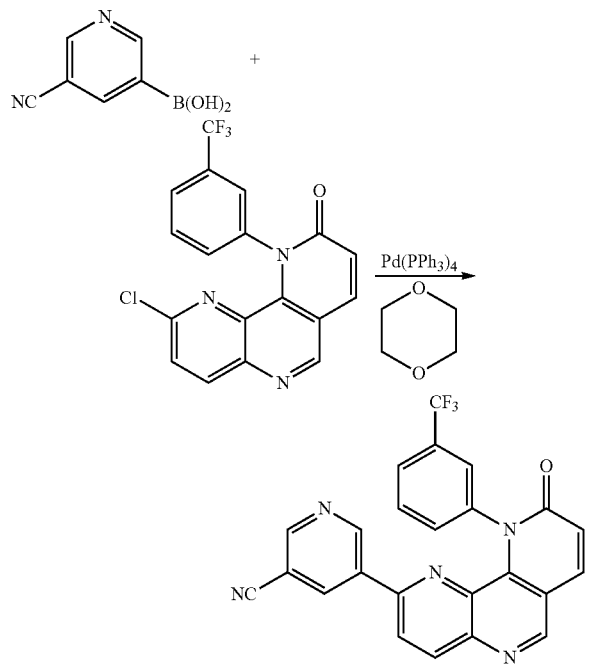

2-chloro-10-(3-(trifluoromethyl)phenyl)pyrido[3,2-c][1,5]naphthyridin-9(10H)-one (200 mg, 0.532 mmol) and 5-cyanopyridin-3-yl boric acid (95 mg, 0.642 mmol) were dissolved in 1,4-dioxane (12 mL). To this system were added palladium tetrakis(triphenylphosphine) (10 mg), and 2N sodium carbonate solution (0.9 mL). The resulting mixture was reacted under reflux in a nitrogen-protecting atmosphere for 6 hr. The reaction mixture was cooled to room temperature and filtered. The organic layer was separated out, concentrated in a reduced pressure, dissolved in dichlormethane, successively washed with water and saturated brine, dried over anhydrous sodium sulfate, concentrated, and purified with a silica-gel column chromatography (ethyl acetate) to produce 186 mg of the target compound in a yield of 78.8%.

Formula: $C_{24}H_{12}F_3N_5O$ MW: 443.10 MS (M+H): 444.10

$^1$H-NMR (d$_6$-DMSO, 400 MHz): δ 9.29 (1H, s), 9.05 (1H, d), 8.70 (1H, d), 8.57 (1H, d), 8.44 (1H, d), 8.39 (1H, d), 7.89-7.74 (5H, m), 7.02 (1H, d).

Example 30

Preparation of 2-(6-(pyrrolidin-1-yl)pyridin-3-yl)-10-(3-(trifluoromethyl)phenyl)pyrido[3,2-c][1,5]naphthyridin-9(10H)-one (Compound 36)

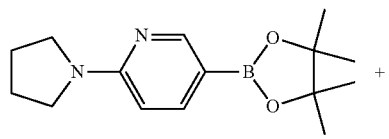

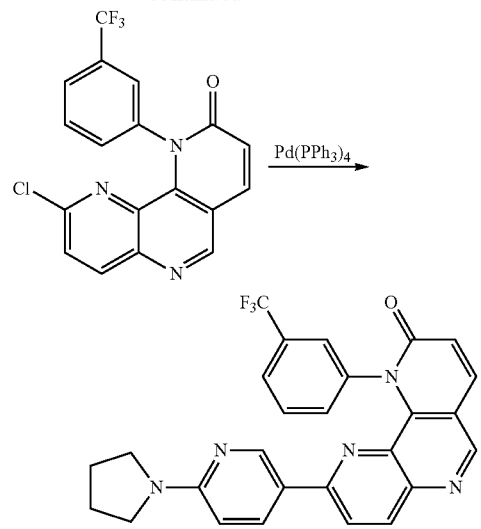

The specific processure was the same as those in Example 1, Step 4, except for substituting 2-chloro-10-(3-(trifluoromethyl)phenyl)pyrido[3,2-c][1,5]naphthyridin-9(10H)-one (188 mg, 0.50 mmol) and 2-(pyrrolidin-yl)-5-(4,4,5,5-tetramethyl-1,3,2-dioxaborolan-2-yl)-pyridine (165 mg, 0.602 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 198 mg of the target compound in a yield of 81.2%.

Formula: $C_{27}H_{20}F_3N_5O$ MW: 487.16 MS (M+H): 488.2

$^1$H-NMR (d$_6$-DMSO, 400 MHz): δ 9.13 (1H, s), 8.36-8.33 (2H, m), 8.32 (1H, s), 8.19 (1H, d), 7.90-7.83 (2H, m), 7.71 (1H, t), 7.59 (1H, d), 6.95 (1H, d), 6.85 (1H, dd), 6.21 (1H, d), 3.46-3.38 (4H, m), 1.99-1.93 (4H, m).

Example 31

Preparation of 2-(1-methyl-1H-pyrazol-4-yl)-10-(3-(trifluoromethyl)phenyl)pyrido[3,2-c][1,5]naphthyridin-9(10H)-one (Compound 37)

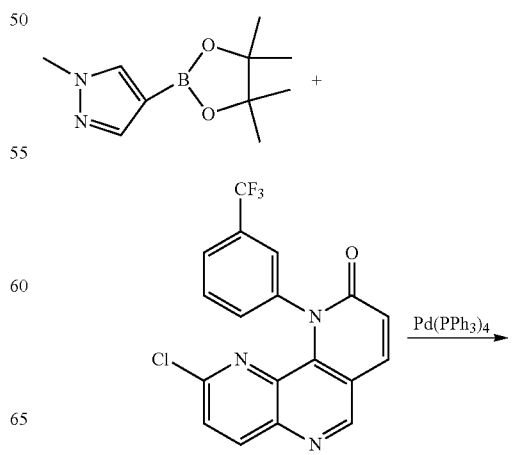

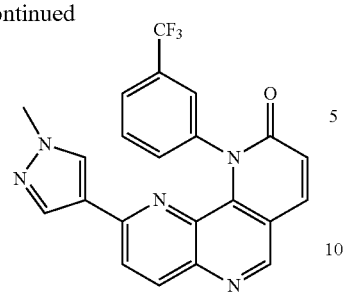

The specific processrss was the same as those in Example 1, Step 4, except for substituting 2-chloro-10-(3-(trifluoromethyl)phenyl)pyrido[3,2-c][1,5]naphthyridin-9(10H)-one (188 mg, 0.50 mmol) and 1-methyl-4-(4,4,5,5-tetramethyl-1,3,2-dioxaborolan-2-yl)-1H-pyrazole (125 mg, 0.60 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 163 mg of the target compound in a yield of 77.4%.

Formula: $C_{22}H_{14}F_3N_5O$ MW: 421.12 MS (M+H): 422.2

$^1$H-NMR ($d_6$-DMSO, 400 MHz): δ 9.12 (1H, s), 8.36-8.28 (2H, m), 7.97-7.89 (2H, m), 7.84 (1H, s), 7.76 (1H, t), 7.60 (1H, d), 7.43 (1H, s), 7.25 (1H, s), 6.94 (1H, d), 3.79 (3H, s).

Example 32

Preparation of 2-(6-(methylthio)pyridin-3-yl)-10-(3-(trifluoromethyl)phenyl)pyrido[3,2-c][1,5]naphthyridin-9(10H)-one (Compound 38)

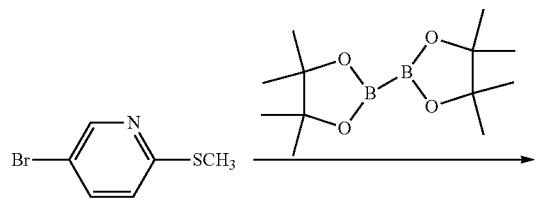

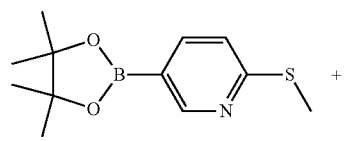

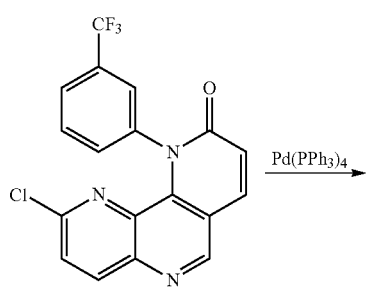

1. Preparation of 2-(methylthio)-5-(4,4,5,5-tetramethyl-1,3,2-dioxaborolan-2-yl)pyridine

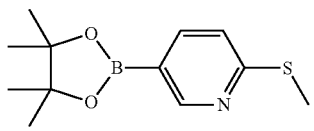

To 1,4-dioxane (20 mL) was successively added 5-bromo-2-(methylthio)pyridine (326 mg, 1.60 mmol), bis(pinacolato)diboron (608 mg, 2.39 mmol), potassium acetate (402 mg, 4.08 mmol) and [1,1'-bis(diphenylphosphino)ferrocene]palladium(II) chloride dichlormethane complex (35 mg), The resulting mixture was reacted under stirring in a nitrogen-protecting atmosphere at 90° C. for 12 hrs. The reaction mixture was cooled and directly used in the next step without a further treatment.

2. Preparation of 2-(6-(methylthio)pyridin-3-yl)-10-(3-(trifluoromethyl)phenyl)pyrido[3,2-c][1,5]naphthyridin-9(10H)-one

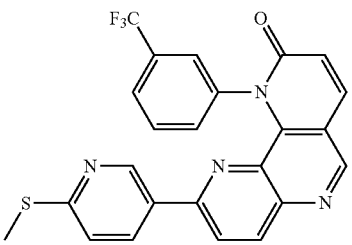 [SMILES: CSc1ccc(-c2ccc3ncc4ccc(=O)n(-c5cccc(C(F)(F)F)c5)c4c3n2)cn1]

To the cooled reaction liquor of 2-(methylthio)-5-(4,4,5,5-tetramethyl-1,3,2-dioxaborolan-2-yl)pyridine obtained in the above step, were added 2-chloro-10-(3-(trifluoromethyl)phenyl)pyrido[3,2-c][1,5]naphthyridin-9(10H)-one (300 mg, 0.799 mmol), palladium tetrakis(triphenylphosphine) (15 mg) and 2N sodium carbonate solution (2.4 mL). This system was reacted in a nitrogen-protecting atmosphere at 90° C. for 16 h, cooled to room temperature and filtered. The organic layer was separated out, concentrated in a reduced pressure, dissolved in dichlormethane, successively washed with water and saturated brine, dried over anhydrous sodium sulfate, concentrated, and purified with a silica-gel column chromatography (ethyl acetate) to produce 153 mg of the target compound in a yield of 41.3%.

Formula: $C_{24}H_{15}F_3N_4OS$ MW: 464.09 MS (M+H): 465.1

$^1$H-NMR (d$_6$-DMSO, 400 MHz): δ 9.24 (1H, s), 8.50 (1H, d), 8.48 (1H, d), 8.37 (1H, d), 8.34 (1H, d), 7.90 (1H, d), 7.87 (1H, s), 7.74 (1H, t), 7.64 (1H, d), 7.18-7.09 (2H, m), 6.99 (1H, d), 2.56 (3H, s).

Example 33

Preparation of 2-(1H-pyrrolo[2,3-b]pyridin-5-yl)-10-(3-(trifluoromethyl)phenyl)pyrido[3,2-c][1,5]naphthyridin-9(10H)-one (Compound 39)

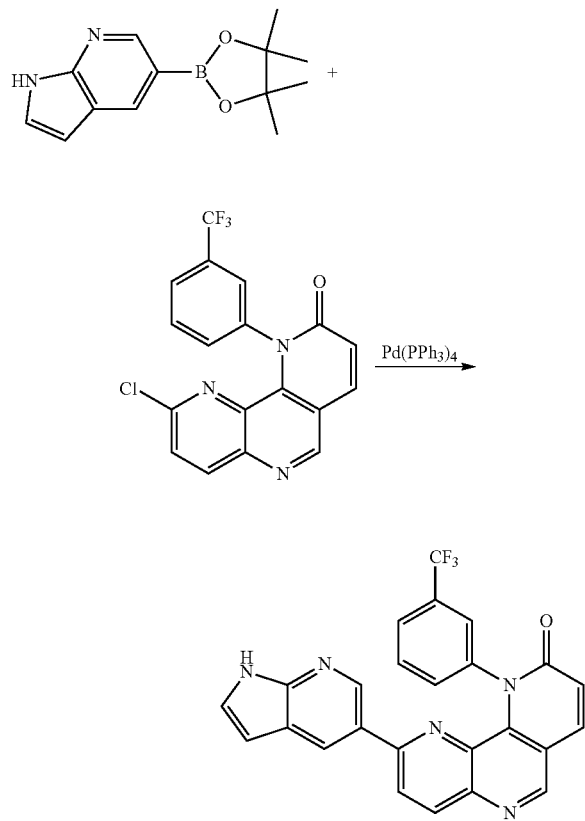

The specific processure was the same as those in Example 1, Step 4, except for substituting 2-chloro-10-(3-(tri fluoromethyl)phenyl)pyrido[3,2-c][1,5]naphthyridin-9 (10H)-one (150 mg, 0.399 mmol) and 5-(4,4,5,5-tetramethyl-1,3,2-dioxaborolan-2-yl)-1H-pyrrolo[2,3-b]pyridine (117 mg, 0.479 mmol) respectively for 2-chloro-10-(3-(trifluoromethyl)phenyl)pyrido[3,2-c][1,5]naphthyridin-9(10H)-one and 5-(4,4,5,5-tetramethyl-1,3,2-dioxaborolan-2-yl)pyridin-2-amine to produce 94 mg of the target compound in a yield of 51.6%.

Formula: $C_{25}H_{14}F_3N_5O$ MW: 457.12 MS (M+H): 458.1

$^1$H-NMR (d$_6$-DMSO, 400 MHz): δ 11.83 (1H, s), 9.21 (1H, s), 8.45 (1H, d), 8.38 (1H, d), 8.36 (1H, d), 8.26 (1H, d), 7.90 (1H, d), 7.87 (1H, s), 7.78 (1H, t), 7.70 (1H, d), 7.53 (1H, d), 7.52 (1H, t), 6.98 (1H, d), 6.51 (1H, dd).

II. In Vitro Enzymology and Antineoplastic Activity Assays of the Present Compounds Hereinafter, the beneficial effects of the present compounds will be illustrated by in vitro enzymology and antineoplastic assay of the present compounds. However, it should be noted that the beneficial effects of the present compounds are not limited to the effects as illustrated below.

Assay 1

In Vitro Enzymology Inhibitory Activity of the Present Compounds

Samples:

The present compounds: lab-made, their chemical names and structural formulae are shown in the preparation examples.

mTOR Enzymology Assay Procedures

1. The agent's final concentrations and the compound solution preparation 1.1 mTOR (2.5 nM) kinase solution, substrate ULight-4E-BP1 peptide 50 nM, ATP 10.8 uM;

1.2 4 folds kinase solution, 2 folds substrate and ATP solution;

1.3 test compound 1 mM stock solution (final concentration 100 folds of DMSO solution).

2. Assay process 2.1 test compound 1 mM, diluted with DMSO 4 folds gradient, and then diluted with kinase buffer 25 folds;

2.2 To each well in a 384-well plate was added 2.5 μL series diluted compounds;

2.3 To each well was added 2.5 μL 4 fold kinase solution;

2.4 To each well was added 2.5 μL substrate/ATP solution;

2.5 incubated for 60 mins;

2.6 Envision data reading Lance signal (665 nM).

3. Data processing

The inhibition ratio %=(Lance signal−min)/(max−min)×100 wherein "max" is the DMSO control containing the enzyme but not containing the compound; "min" is the control without the kinase.

Input the data into GraphPad Prism5.0 to plot a curve and obtain IC$_{50}$.

PI3Kα Enzymology Assay Procedures

1. The agent's final concentrations and the compound formulation 1.1 PI3Kα (1.65 nM) kinase solution, substrate PIP2 50 μM, ATP 25 μM;

1.2 4 folds kinase solution, 2 folds substrate and ATP solution;

1.3 test compound 1 mM stock solution (final concentration 100 folds of DMSO solution).

2. Assay process 2.1 test compound 1 mM, diluted with DMSO 4 folds gradient, and then diluted with kinase buffer 25 folds;

2.2 To each well in a 384-well plate was added 2.5 μL series diluted compounds;

2.3 To each well was added 2.5 μL 4 folds kinase solution;

2.4 To each well was added 2.5 μL substrate/ATP solution;

2.5 incubated for 60 mins;

2.6 Envision data reading: Lance signal (665 nM).

3. Data processing

The inhibition ratio %=(sample RLU−min)/(max−min)×100 wherein "max" is the control without the kinase; "min" is the DMSO control containing the enzyme but not containing the compound.

Data were input into GraphPad Prism 5.0 to plot a curve and obtain IC$_{50}$.

Results

See the Table 1 below.

TABLE 1 the activities of the present compounds in vitro enzymology ($IC_{50}$)

| Tested substance | PI3Kα (nM) | mTOR (nM) |
| --- | --- | --- |
| Compound 1 | 3.2 | 0.87 |
| Compound 13 | 2.4 | 0.47 |
| Compound 14 | 8.8 | 4.4 |
| Compound 15 | 6.1 | 3 |
| Compound 16 | 58 | 8.7 |
| Compound 17 | 45 | 5.3 |
| Compound 18 | 3.6 | 2.6 |
| Compound 19 | 158 | 2.3 |
| Compound 20 | 104 | 6 |
| Compound 38 | 17 | 5 |
| Compound 39 | 2.5 | 0.89 |

Conclusion

It could be seen from Table 1 that the present compounds had a good in vitro inhibitory activity for both of the enzymes PI3Kα and mTOR.

Assay 2

In Vitro Cellular Inhibitory Activity of the Present Compounds

Samples:

Controls: Torin-2, its structure is shown in the section "Background" hereinbefore and synthesized according to the method in the following literature: Journal of Medicinal Chemistry (2011), 54(5), 1473-1480, "Discovery of 9-(6-Aminopyridin-3-yl)-1-(3-(trifluoromethyl)phenyl)benzo[h][1,6]naphthyridin-2(1H)-one (Torin2) as a potent, selective, and orally available mammalian target of rapamycin (mTOR) inhibitor for treatment of cancer"; and the present compounds: lab-made, their chemical names and structural formulae are shown in the preparation examples.

Positive control: paclitaxel

Assay Procedures:

1. Formulating the agents and the compounds: Formulating the PBS, the XTT working liquor, the paclitaxel stock solution and gradient dilute solutions thereof, and the stock solution of test compound and gradient dilute solutions of test compounds.
2. Culturing cells: Thawing cells, Passing cells, Freezing and preserving cells.
3. Plating Cells:

Preparing the cell suspension;

The cell suspension was added to a 96-well plate, 100 μL per well;

The plate was placed in the incubator and incubated at 37° C. under 5% $CO_2$ overnight.

4. Treating with drugs

Drugs were added to the cell culture plate. The plate was placed in the $CO_2$ incubator and incubated for 72 hours.

5. Testing the cell viability with the XTT method

The XTT working solution was added to the plate. The plate was placed in the $CO_2$ incubator for 2 hours. Then the plate was placed in a microplate reader to read the absorbance at 450 nm.

6. Data processing

1) % inhibition=(Absorbance (Vehicle)−Absorbance(Compound))/(Absorbance(Vehicle)−Absorbance(positive control))×100%;

2) Data were input into GraphPad Prism 5.0 to plot a curve and obtain $IC_{50}$.

Result:

See the Table 2 below.

TABLE 2

In vitro cytological activities of the present compounds ($IC_{50}$)

| Tested substance | U87MG cells (nM) | A549 cells (nM) |
| --- | --- | --- |
| Torin-2 | 12.4 | 14.7 |
| Compound 1 | 8.9 | 11.9 |
| Compound 7 | 29.3 | — |
| Compound 13 | 26.4 | — |
| Compound 15 | 12.7 | 20.2 |
| Compound 39 | 8.4 | 6.8 |

Conclusion:

It could be seen from Table 2 that the present compounds could effectively inhibit the proliferations of U87MG and A549 cells, and had a comparable activity over the control drug Torin-2.

Assay 3:

Pharmacokinetic Assay of the Present Compounds in Rat In Vivo

Tested Animals

Male SD rats, each test substance, each administration, three rats were used, having a body weight of 200-250 g.

Test Substances:

Control drug: Torin-2, dissolved with 5% NMP+40% PEG400+55% sterile water for injection;

the present compounds: Compound 16, dissolved with 5% NMP+60% PEG400+35% sterile water for injection, other compounds, dissolved with 5% NMP+40% PEG400+55% sterile water for injection.

Assay Procedures:

Administration: The administration manner and dosage of the test substance are shown in the following Table 3

TABLE 3

Administration manner and dosage of Test substances

| Tested substance | Intervenous push injection (IV) | | intragastric administration (PO) | |
| --- | --- | --- | --- | --- |
| | Dosage (mg/kg) | Volume (mL/kg) | Dosage (mg/kg) | Volume (mL/kg) |
| Torin-2 | 2 | 4 | 4 | 8 |
| Compound 1 | 2 | 2 | 4 | 4 |
| Compound 13 | 2 | 2 | 4 | 4 |
| Compound 14 | — | — | 4 | 4 |
| Compound 15 | 2 | 2 | 4 | 4 |
| Compound 16 | 0.45 | 2 | 4 | 4 |
| Compound 17 | 2 | 2 | 4 | 4 |

Blood collection: each of about 100 μL whole blood were collected at 0 h before administration (pre-administration), and at 0.083 h, 0.25 h, 0.5 h, 1 h, 2 h, 4 h, 6 h, 8 h and 24 h after administration. The collected blood samples were centrifuged at 8000 rpm in a high-speed centrifuge for 6 mins to separate the blood plasma. The separated plasm was freezing-preserved at −80° C. in a refrigerator.

Plasm sample analysis: The plasm sample was treated by a liquid-liquid extraction. 20 μL of the plasma was taken, subjected to a vortex at 1500 rpm for 10 mins, and then centrifuged at 12000 rpm for 5 mins. 400 μL of the supernatant was taken and blowed to dryness in the nitrogen gas. The resulting substance is re-dissolved in 200 μL methanol:water (1:1, V/V), and the solution was analyzed with LC-MS/MS.

Result:
See the Table 4 below.

TABLE 4

Rat PK evaluation result of the present compounds (Dosage in Table 3)

| Tested substance | IV(2 mg/kg) | | PO(4 mg/kg) | | |
|---|---|---|---|---|---|
| | $T_{1/2}$ (h) | $AUC_{last}$ (h · ng/ml) | $T_{1/2}$ (h) | $AUC_{last}$ (h · ng/ml) | F(%) |
| Torin-2 | 0.86 | 259.24 | 2.55 | 104.32 | 22.64 |
| Compound 1 | 1.79 | 1306 | 2.78 | 1029 | 43.7 |
| Compound 13 | 0.62 | 710.62 | 1.44 | 706.62 | 48.96 |
| Compound 14 | — | — | 3.49 | 445.1 | 42.26 |
| Compound 15 | 0.71 | 440.83 | 2.36 | 549.8 | 64.96 |
| Compound 16 | 1.52 | 194.82 | 1.67 | 409.84 | 23.04 |
| Compound 17 | 0.61 | 723.12 | 5.68 | 212.35 | 20.82 |

$T_{1/2}$ represents the half-life
$AUC_{last}$ represents the area under curve on administration from time = 0→t)
F % represents the absolute bioavailability

CONCLUSION

It could be seen from Table 4 that, whether with the intravenous injection administration or with the oral administration, the present compounds had a remarkably higher $AUC_{last}$ than that of the control drug, which demonstrated that the present compounds had a good pharmacokinetic characteristic and an excellent potential of being developed into drug.

The invention claimed is:

1. A compound represented by general formula (I), or a pharmaceutically acceptable salt, stereoisomer or deuteride thereof:

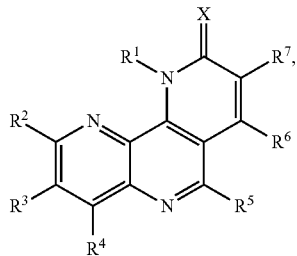

(I)

wherein:
X is O;
$R^1$ is 6-10-membered aryl, 3-8-membered saturated monocyclic heterocyclyl or 5-6-membered aromatic monocyclic heterocyclyl, all of which are unsubstituted or substituted by 1-3 $R^8$;
$R^2$ is 6-10-membered aryl or 5-10-membered heterocyclyl, which is unsubstituted or substituted by 1-3 $R^{8'}$;
each of $R^3$, $R^4$ and $R^5$ is hydrogen;
each of $R^6$ and $R^7$ is independently hydrogen or $C_{1-4}$alkyl;
$R^8$ is
(1) hydroxy, halogen, cyano, amino or —C(O)$R^c$,
(2) $C_{1-4}$alkyl or $C_{1-4}$alkoxyl, both of which are unsubstituted or substituted by 1-3 substitutents selected from cyano, halogen and/or hydroxy, or
(3) 5-6-membered saturated monocyclic heterocyclyl, which is unsubstituted or substituted by 1-3 substitutents selected from cyano, trifluoromethyl, halogen, —C(O)$R^{c'}$, —C(O)(CH$_2$)$_n$NR$^a$R$^b$ and/or —S(O)$_2$R$^{c'}$;
$R^{8'}$ is
(1) hydroxy, halogen, cyano, amino, —(CH$_2$)$_n$NR$^a$C(O)R$^c$ or —(CH$_2$)$_n$S(O)$_m$R$^c$,
(2) $C_{1-4}$alkyl or $C_{1-4}$alkoxyl, both of which are unsubstituted or substituted by 1-3 substitutents selected from cyano, halogen and/or hydroxy, or
each of $R^a$ and $R^b$ is independently hydrogen, or $C_{1-4}$alkyl that is unsubstituted or substituted by 1-3 substitutents selected from hydroxy and/or halogen;
$R^c$ is $C_{1-4}$alkyl or $C_{1-4}$alkoxyl, both of which are unsubstituted or substituted by 1-3 substitutents selected from hydroxy, halogen and/or cyano;
$R^{c'}$ is $C_{1-4}$alkyl or $C_{1-4}$alkoxyl, both of which are unsubstituted or substituted by 1-3 substitutents selected from hydroxy and/or halogen;
m is 0, 1 or 2; and
n is 0, 1, 2 or 3.

2. The compound of claim 1 or a pharmaceutically acceptable salt, stereoisomer or deuteride thereof, wherein
$R^1$ is phenyl, naphthyl or 5-6-membered saturated monocyclic heterocyclyl, all of which are unsubstituted or substituted by 1-3 $R^8$;
$R^2$ is phenyl, pyridinyl, pyrimidinyl, pyridazinyl, pyrazinyl, pyrazolyl, imidazolyl, pyrrolyl, oxazolyl, isoxazolyl, thiazolyl, isothiazolyl, indazolyl, quinolinyl, isoquinolinyl, indolyl, pyrrolopyridine, dihydropyrrolopyridine or pyrazolopyridinyl, all of which are unsubstituted or substituted by 1-3 $R^{8'}$;
each of $R^6$ and $R^7$ is independently hydrogen or methyl;
$R^8$ is
(1) amino or —C(O)$R^c$, $R^c$ is $C_{1-4}$alkyl that is unsubstituted or substituted by hydroxy or halogen,
(2) $C_{1-4}$alkyl or $C_{1-4}$alkoxyl, both of which are unsubstituted or substituted by cyano or 1-3 fluoro, or
(3) piperazinyl or piperidinyl, both of which are unsubstituted or substituted by cyano or trifluoromethyl;
$R^{8'}$ is
(1) hydroxy, halogen, amino, cyano, —NHC(O)$R^c$ or —S(O)$_m$R$^c$, wherein m is 0 or 2, $R^c$ is $C_{1-4}$alkyl,
(2) $C_{1-4}$alkyl or $C_{1-4}$alkoxyl, both of which are unsubstituted or substituted by hydroxy or 1-3 fluoro.

3. The compound of claim 1, or a pharmaceutically acceptable salt, stereoisomer or deuteride thereof, wherein
$R^1$ is 6-10-membered aryl or 5-6-membered saturated monocyclic heterocyclyl, both of which are unsubstituted or substituted by 1-3 $R^8$, wherein $R^8$ is (1) amino or —C(O)$R^c$, $R^c$ is $C_{1-4}$alkyl that is unsubstituted or substituted by hydroxy or halogen, (2) $C_{1-4}$alkyl or $C_{1-4}$alkoxyl, both of which are unsubstituted or substituted by cyano or 1-3 halogens, or (3) 5-6-membered saturated monocyclic heterocyclyl that is unsubstituted or substituted by cyano or trifluoromethyl; and/or
$R^2$ is 6-10-membered aryl, 5-6-membered partially saturated monocyclic heterocyclyl, 5-6-membered aromatic monocyclic heterocyclyl or 9-10-membered fused heterocyclyl, all of which are unsubstituted or substituted by 1-3 $R^{8'}$, wherein $R^{8'}$ is (1) hydroxy, halogen, amino, cyano, —NHC(O)$R^c$ or —S(O)$_m$R$^c$, wherein m is 0, 1 or 2, $R^c$ is $C_{1-4}$alkyl, (2) $C_{1-4}$alkyl or $C_{1-4}$alkoxyl, both of which are unsubstituted or substituted by hydroxy or 1-3 halogens.

4. The compound of claim 2, or a pharmaceutically acceptable salt, stereoisomer or deuteride thereof, wherein
$R^1$ is phenyl, piperidinyl or piperazinyl, all of which are unsubstituted or substituted by 1-2 $R^8$;

R² is phenyl, pyridinyl, pyrimidinyl, pyridazinyl, pyrazinyl, pyrazolyl, imidazolyl, pyrrolyl, oxazolyl, isoxazolyl, thiazolyl, isothiazolyl, quinolinyl, isoquinolinyl, pyrrolopyridine, dihydropyrrolopyridine or indolyl, all of which are unsubstituted or substituted by 1-2 R⁸';

R⁸ is
(1) amino or —C(O)Rᶜ, Rᶜ is C₁₋₄alkyl that is unsubstituted or substituted by hydroxy,
(2) C₁₋₄alkyl that is unsubstituted or substituted by cyano or three fluoro, or
(3) piperazinyl or piperidinyl, both of which are unsubstituted or substituted by cyano or trifluoromethyl;

R⁸' is
(1) halogen, amino, cyano, —NHC(O)Rᶜ or —S(O)ₘRᶜ, wherein m is 0 or 2, Rᶜ is C₁₋₄alkyl,
(2) C₁₋₄alkyl or C₁₋₄alkoxyl, both of which are unsubstituted or substituted by hydroxy or three fluoro.

5. The compound of claim 1, or a pharmaceutically acceptable salt, stereoisomer or deuteride thereof, wherein said compound is selected from:
2-(6-aminopyridin-3-yl)-10-(3-(trifluoromethyl)phenyl)pyrido[3,2-c][1,5]naphthyridin-9(10H)-one,
2-(6-methoxypyridin-3-yl)-10-(4-(piperazin-1-yl)-3-(trifluoromethyl)phenyl)pyrido[3,2-c][1,5]naphthyridin-9(10H)-one,
(R)-2-(6-aminopyridin-3-yl)-10-(1-(2-hydroxypropanoyl)piperidin-4-yl)pyrido[3,2-c][1,5]naphthyridin-9(10H)-one,
(R)-10-(1-(2-hydroxypropanoyl)piperidin-4-yl)-2-(6-methoxypyridin-3-yl)pyrido[3,2-c][1,5]naphthyridin-9(10H)-one,
2-methyl-2-(4-(9-oxo-2-(quinolin-3-yl)pyrido[3,2-c][1,5]naphthyridin-10(9H)-yl)phenyl)propanenitrile,
2-(6-aminopyridin-3-yl)-10-(4-(piperazin-1-yl)-3-(trifluoromethyl)phenyl)pyrido[3,2-c][1,5]naphthyridin-9(10H)-one,
2-(4-(2-(6-aminopyridin-3-yl)-9-oxopyrido[3,2-c][1,5]naphthyridin-10(9H)-yl)phenyl)-2-methylpropanenitrile,
2-(6-methoxypyridin-3-yl)-10-(3-(trifluoromethyl)phenyl)pyrido[3,2-c][1,5]naphthyridin-9(10H)-one,
2-(quinolin-3-yl)-10-(3-(trifluoromethyl)phenyl)pyrido[3,2-c][1,5]naphthyridin-9(10H)-one,
10-(4-(piperazin-1-yl)-3-(trifluoromethyl)phenyl)-2-(quinolin-3-yl)pyrido[3,2-c][1,5]naphthyridin-9(10H)-one,
(R)-10-(1-(2-hydroxypropanoyl)piperidin-4-yl)-2-(quinolin-3-yl)pyrido[3,2-c][1,5]naphthyridin-9(10H)-one,
2-(4-(2-(6-methoxypyridin-3-yl)-9-oxopyrido[3,2-c][1,5]naphthyridin-10(9H)-yl)phenyl)-2-methylpropanenitrile,
2-(2-aminopyrimidin-5-yl)-10-(3-(trifluoromethyl)phenyl)pyrido[3,2-c][1,5]naphthyridin-9(10H)-one,
2-(2-methoxypyrimidin-5-yl)-10-(3-(trifluoromethyl)phenyl)pyrido[3,2-c][1,5]naphthyridin-9(10H)-one,
N-(5-(9-oxo-10-(3-(trifluoromethyl)phenyl)-9,10-dihydropyrido[3,2-c][1,5]naphthyridin-2-yl)pyridin-2-yl)acetamide,
5-(9-oxo-10-(3-(trifluoromethyl)phenyl)-9,10-dihydropyrido[3,2-c][1,5]naphthyridin-2-yl)-2-cyanopyridine,
2-(1H-pyrrolo[2,3-b]pyridin-3-yl)-10-(3-(trifluoromethyl)phenyl)pyrido[3,2-c][1,5]naphthyridin-9(10H)-one,
2-(6-(hydroxymethyl)pyridin-3-yl)-10-(3-(trifluoromethyl)phenyl)pyrido[3,2-c][1,5]naphthyridin-9(10H)-one,
2-(4-(2-(2-methoxypyrimidin-5-yl)-9-oxopyrido[3,2-c][1,5]naphthyridin-10(9H)-yl)phenyl)-2-methylpropanenitrile,
2-(6-(methylsulfonyl)pyridin-3-yl)-10-(3-(trifluoromethyl)phenyl)pyrido[3,2-c][1,5]naphthyridin-9(10H)-one,
2-(6-methoxypyridin-3-yl)-10-(3-(trifluoromethyl)phenyl)pyrido[3,2-c][1,5]naphthyridin-9(10H)-one,
2-(5-methoxypyridin-3-yl)-10-(3-(trifluoromethyl)phenyl)pyrido[3,2-c][1,5]naphthyridin-9(10H)-one,
2-(2-methoxypyridin-3-yl)-10-(3-(trifluoromethyl)phenyl)pyrido[3,2-c][1,5]naphthyridin-9(10H)-one,
10-(3-(trifluoromethyl)phenyl)-2-(6-(trifluoromethyl)pyridin-3-yl)pyrido[3,2-c][1,5]naphthyridin-9(10H)-one,
2-(6-methylpyridin-3-yl)-10-(3-(trifluoromethyl)phenyl)pyrido[3,2-c][1,5]naphthyridin-9(10H)-one,
2-(3,5-dimethylisoxazol-4-yl)-10-(3-(trifluoromethyl)phenyl)pyrido[3,2-c][1,5]naphthyridin-9(10H)-one,
2-(5-fluoropyridin-3-yl)-10-(3-(trifluoromethyl)phenyl)pyrido[3,2-c][1,5]naphthyridin-9(10H)-one,
10-(3-(trifluoromethyl)phenyl)-2-(5-(trifluoromethyl)pyridin-3-yl)pyrido[3,2-c][1,5]naphthyridin-9(10H)-one,
2-(1-methyl-1H-pyrazol-5-yl)-10-(3-(trifluoromethyl)phenyl)pyrido[3,2-c][1,5]naphthyridin-9(10H)-one,
2-(thiazol-5-yl)-10-(3-(trifluoromethyl)phenyl)pyrido[3,2-c][1,5]naphthyridin-9(10H)-one,
3-methyl-5-(9-oxo-10-(3-(trifluoromethyl)phenyl)-9,10-dihydropyrido[3,2-c][1,5]naphthyridin-2-yl)-2-cyanopyridine,
5-(9-oxo-10-(3-(trifluoromethyl)phenyl)-9,10-dihydropyrido[3,2-c][1,5]naphthyridin-2-yl)-3-cyanopyridine,
2-(1-methyl-1H-pyrazol-4-yl)-10-(3-(trifluoromethyl)phenyl)pyrido[3,2-c][1,5]naphthyridin-9(10H)-one,
2-(6-(methylthio)pyridin-3-yl)-10-(3-(trifluoromethyl)phenyl)pyrido[3,2-c][1,5]naphthyridin-9(10H)-one,
2-(1H-pyrrolo[2,3-b]pyridin-5-yl)-10-(3-(trifluoromethyl)phenyl)pyrido[3,2-c][1,5]naphthyridin-9(10H)-one,
2-(6-(methylsulfonyl)pyridin-3-yl)-10-(4-(piperazin-1-yl)-3-(trifluoromethyl)phenyl)pyrido[3,2-c][1,5]naphthyridin-9(10H)-one,
(R)-10-(1-(2-hydroxypropanoyl)piperidin-4-yl)-2-(6-(methylsulfonyl)pyridin-3-yl)pyrido[3,2-c][1,5]naphthyridin-9(10H)-one,
2-methyl-2-(4-(2-(6-(methylsulfonyl)pyridin-3-yl)-9-oxopyrido[3,2-c][1,5]naphthyridin-10(9H)-yl)phenyl)propanenitrile,
N-(5-(9-oxo-10-(4-(piperazin-1-yl)-3-(trifluoromethyl)phenyl)-9,10-dihydropyrido[3,2-c][1,5]naphthyridin-2-yl)pyridin-2-yl)acetamide,
(R)—N-(5-(10-(1-(2-hydroxypropanoyl)piperidin-4-yl)-9-oxo-9,10-dihydropyrido[3,2-c][1,5]naphthyridin-2-yl)pyridin-2-yl)acetamide,
N-(5-(10-(4-(2-cyanopropan-2-yl)phenyl)-9-oxo-9,10-dihydropyrido[3,2-c][1,5]naphthyridin-2-yl)pyridin-2-yl)acetamide,
5-(9-oxo-10-(4-(piperazin-1-yl)-3-(trifluoromethyl)phenyl)-9,10-dihydropyrido[3,2-c][1,5]naphthyridin-2-yl)-2-cyanopyridine,
(R)-5-(10-(1-(2-hydroxypropanoyl)piperidin-4-yl)-9-oxo-9,10-dihydropyrido[3,2-c][1,5]naphthyridin-2-yl)-2-cyanopyridine,
5-(10-(4-(2-cyanopropan-2-yl)phenyl)-9-oxo-9,10-dihydropyrido[3,2-c][1,5]naphthyridin-2-yl)-2-cyanopyridine, 2-(6-(methylthio)pyridin-3-yl)-10-(4-(piperazin-1-yl)-3-(trifluoromethyl)phenyl)pyrido[3,2-c][1,5]naphthyridin-9(10H)-one, (R)-1-(1-(2-hydroxypropanoyl)piperidin-4-yl)-2-(6-(methylthio)pyridin-3-yl)pyrido[3,2-c][1,5]naphthyridin-9(10H)-one, and 2-methyl-2-(4-(2-(6-(methylthio)pyridin-3-yl)-9-oxopyrido[3,2-c][1,5]naphthyridin-10(9H)-yl)phenyl)propanenitrile.

6. A pharmaceutical composition, comprising the compound of claim 1, or a pharmaceutically acceptable salt, stereoisomer or deuteride thereof.

7. The pharmaceutical composition of claim 6, which further comprises one or more antineoplastic agent(s) and/or immunosuppressive agent(s), said antineoplastic agent and said immunosuppressive agent are antimetabolite selected from capecitabine, gemcitabine, pemetrexed disodium; growth factor inhibitor selected from pazopanib, imatinib, erlotinib, lapatinib, gefitinib, vandetanib; antibody selected from herceptin, bevacizumab; mitotic inhibitor selected from paclitaxel, vinorelbine, docetaxel, doxorubicin; antineoplastic hormone selected from letrozole, tamoxifen, fulvestrant, flutamide, triptorelin; alkylating agent selected from cyclophosphamide, chlormethine, mnelphalan, chlorambucil, carmustine; metallic platinum selected from carboplatin, cisplatin, oxaliplatin; topoismerase inhibitor selected from topotecan camptothecin, topotecan, irinotecanpto; immunosuppressive agent selected from everolimus, sirolimus, torisel; purine analogues selected from 6-mercaptopurine, 6-thioguanine, azathioprine; antibiotics selected from actinomycin D, daunorubicin, adriamycin, mitoxantrone, bleomycin, plicamycin; platinum complex selected from cisplatin, carboplatin; adrenal cortex inhibitors selected from aminoglutethimide.

8. A pharmaceutical formulation comprising the compound of claim 1 or a pharmaceutically acceptable salt, stereoisomer or deuteride thereof, and one or more pharmaceutically acceptable carriers, which is in any dosage form that is clinically or pharmaceutically acceptable.

9. A method for treating a proliferative disease, selected from lung cancer, non-small cell lung cancer, small cell lung cancer, glioma, glioma sarcomatosum, mammary cancer, prostrate tumor, renal cancer, ovarian cancer and colon cancer which comprises a step of administering an effective amount of the compound of claim 1, or a pharmaceutically acceptable salt, stereoisomer or deuteride thereof to a subject in need thereof.

10. A method for preparing the compound of general formula (I) of claim 1, i.e., the following formula

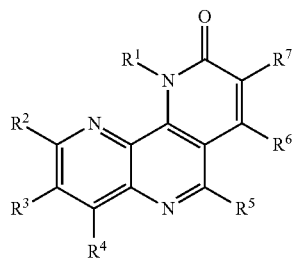

which method comprises the following steps:

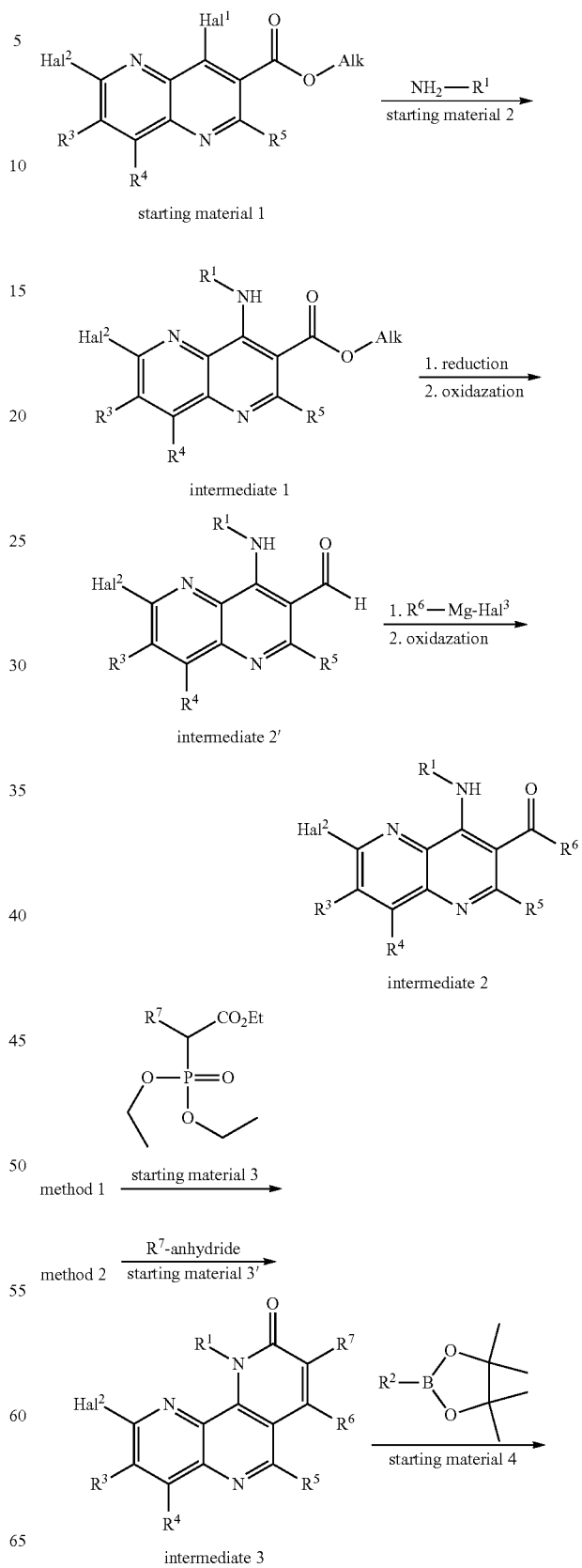

-continued

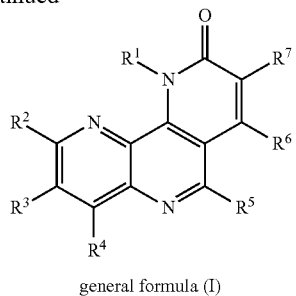

general formula (I)

wherein $R^1$, $R^2$, $R^3$, $R^4$, $R^5$, $R^6$ and $R^7$ are defined as hereinbefore, $Hal^1$, $Hal^2$ and $Hal^3$ represent halogen, which is each independently selected from the group consisting of F, Cl, Br and I, and Hal, $Hal^2$ and $Hal^3$ can be identical or different; Alk represents a lower alkyl; "anhydride" is an organic acid anhydride;

(1) preparation of intermediate 1 starting material 1 and starting material 2 are reacted under heating to reflux in an alcohol organic solvent in presence of a base until the starting material disappears to produce intermediate 1;

(2) preparation of intermediate 2' intermediate 1 is reacted with a reductant in an alcohol organic solvent; the solvent is removed under a reduced pressure; water is added to the reaction mixture; the resulting mixture is extracted with a halogenated hydrocarbon organic solvent; the organic phase is concentrated, to which is added an oxidant; the resulting mixture is reacted under stirring to produce intermediate 2';

(3) preparation of intermediate 2 in the nitrogen protection, intermediate 2' and a Grignard reagent $R^6$—Mg-$Hal^3$ are reacted and then oxidized to produce Intermediate 2;

(4) preparation of intermediate 3 method 1: in a sealed vessel, intermediate 2 and starting material 3 are reacted in an alcohol organic solvent in the presence of an inorganic base at 110-180° C. to produce intermediate 3; or method 2: intermediate 2 is dissolved in a non-protonic polar organic solvent and starting material 3'; the reaction is conducted in a microwave reactor until the starting material disappears to produce intermediate 3; and (5) preparation of compound of formula (I)

intermediate 3 and starting material 4 are dissolved in an organic solvent; the resulting mixture was reacted in the presence of a catalyst and a base under reflux in a nitrogen-protecting atmosphere to produce the compound of formula (I);

if necessary, a functional group that needs to be protected can be protected; and afterwards can be deprotected according to the conventional method.

11. The pharmaceutical formulation of claim 8, comprising a dosage of the compound of claim 1, or the pharmaceutically acceptable salt, stereoisomer or deuteride thereof, that inhibits both PI3Kα and mTOR.

\* \* \* \* \*